US012098363B2

(12) United States Patent
Bauer et al.

(10) Patent No.: US 12,098,363 B2
(45) Date of Patent: Sep. 24, 2024

(54) TARGETING BCL11A DISTAL REGULATORY ELEMENTS WITH A CAS9-CAS9 FUSION FOR FETAL HEMOGLOBIN REINDUCTION

(71) Applicants: THE CHILDREN'S MEDICAL CENTER CORPORATION, Boston, MA (US); UNIVERSITY OF MASSACHUSETTS, Boston, MA (US)

(72) Inventors: Daniel E. Bauer, Cambridge, MA (US); Scot Wolfe, Boston, MA (US); Mehmet Fatih Bolukbasi, Brighton, MA (US); Benjamin Roscoe, Worcester, MA (US); Pengpeng Liu, Worcester, MA (US); Kevin Luk, Worcester, MA (US); Yuxuan Wu, Boston, MA (US); Jing Zeng, Boston, MA (US)

(73) Assignees: THE CHILDREN'S MEDICAL CENTER CORPORATION, Boston, MA (US); UNIVERSITY OF MASSACHUSETTS, Boston, MA (US)

( * ) Notice: Subject to any disclaimer, the term of this patent is extended or adjusted under 35 U.S.C. 154(b) by 1029 days.

(21) Appl. No.: 16/964,461

(22) PCT Filed: Jul. 20, 2018

(86) PCT No.: PCT/US2018/043073
§ 371 (c)(1),
(2) Date: Jul. 23, 2020

(87) PCT Pub. No.: WO2019/147302
PCT Pub. Date: Aug. 1, 2019

(65) Prior Publication Data
US 2021/0047632 A1     Feb. 18, 2021

Related U.S. Application Data

(60) Provisional application No. 62/622,599, filed on Jan. 26, 2018.

(51) Int. Cl.
*C12N 15/01* (2006.01)
*A61K 38/46* (2006.01)
(Continued)

(52) U.S. Cl.
CPC ............ *C12N 15/01* (2013.01); *A61K 38/465* (2013.01); *C12N 9/22* (2013.01); *C12N 15/113* (2013.01);
(Continued)

(58) Field of Classification Search
CPC ........ C12N 15/01; C12N 9/22; C12N 15/113; C12N 2310/20; C12N 2510/00;
(Continued)

(56) References Cited

U.S. PATENT DOCUMENTS

| 2015/0307867 A1 | 10/2015 | Orkin et al. |
| 2016/0017366 A1* | 1/2016 | Chen ............... C12N 15/907 |

(Continued)

FOREIGN PATENT DOCUMENTS

| WO | WO-2013176772 A1 * | 11/2013 | ........... A01H 6/4684 |
| WO | 2016182917 A1 | 11/2016 | |

(Continued)

OTHER PUBLICATIONS

Swarts et al., Nature 507(7491): 258-261 (Year: 2014).*
(Continued)

*Primary Examiner* — Robert T. Crow
*Assistant Examiner* — Shabana S Meyering
(74) *Attorney, Agent, or Firm* — Nixon Peabody LLP; David S. Resnick; Jeanne Jodoin

(57) ABSTRACT

Provided herein are methods and compositions for increasing fetal hemoglobin levels in a cell by disrupting BCL11A
(Continued)

expression at the genomic level. Also provided herein are methods and compositions relating to the treatment of hemoglobinopathies by reinduction of fetal hemoglobin levels.

9 Claims, 19 Drawing Sheets

Specification includes a Sequence Listing.

(51) Int. Cl.
*C12N 9/22* (2006.01)
*C12N 15/113* (2010.01)
(52) U.S. Cl.
CPC ...... *C12N 2310/20* (2017.05); *C12N 2510/00* (2013.01); *C12N 2800/80* (2013.01)
(58) Field of Classification Search
CPC .............. C12N 2800/80; A61K 38/465; A61K 2035/124; A61K 35/18; A61K 35/545; A61K 35/28; C07K 14/4702; C07K 14/805

USPC ........... 435/320.1, 455; 424/93.21; 514/44 R
See application file for complete search history.

(56) References Cited

U.S. PATENT DOCUMENTS

2016/0177278 A1    6/2016   Wolfe et al.
2016/0369262 A1* 12/2016   Reik et al.

FOREIGN PATENT DOCUMENTS

WO    WO-2017115268 A1 *   7/2017  ............. A61K 35/12
WO    WO-2017182881 A2 * 10/2017  ........... A61K 31/395

OTHER PUBLICATIONS

Garcia-Doval & Jinek (Current Opinion in Structural Biology, 2017, 47:157-166) (Year: 2017).*
Bolukbasi et al. "37: Development of Orthogonal Cas9-Cas9 Fusion Preteins and Their Potential Application as [beta]-Hemoglobinopathy Therapeutics." Molecular Therapy 26(5): Supplement 1, p. 20 (May 2018).

* cited by examiner

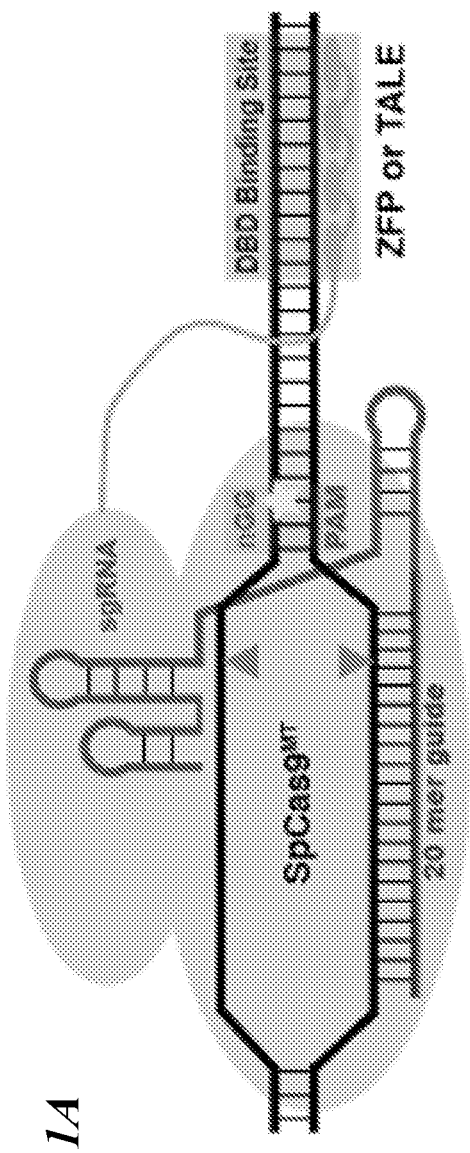
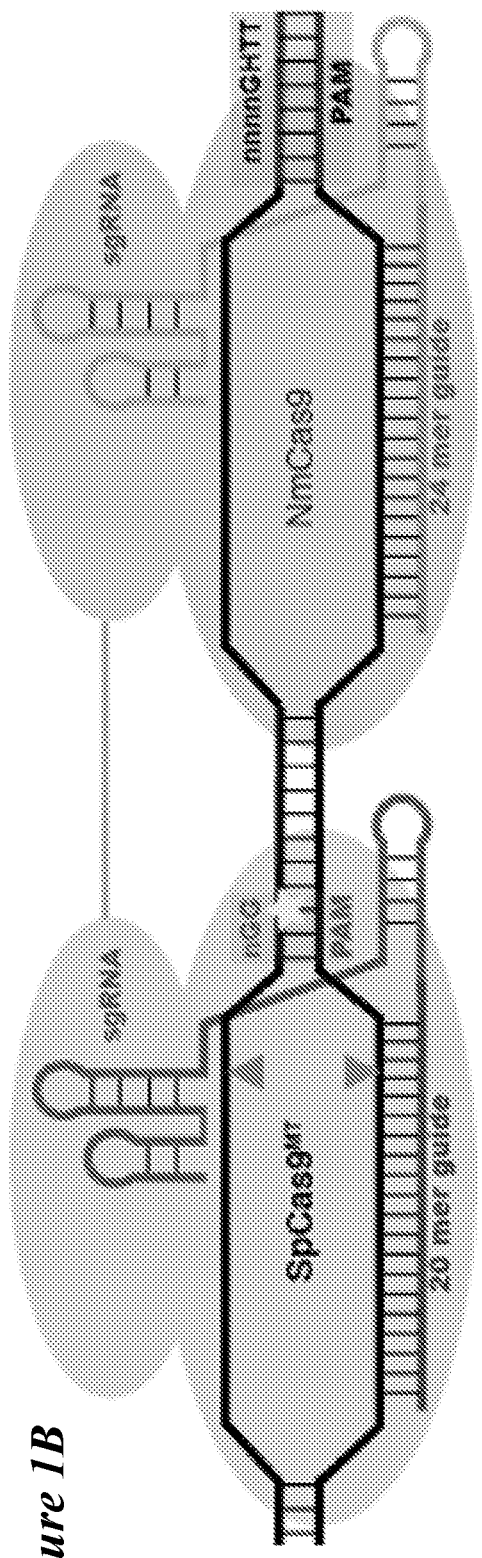
Figure 1A
Figure 1B

*Figure 2F*

```
>BCL11A_enhancer+58
GATA1_TS1:   CACCCCCCACCCTAATCAGAGGCCAAACCCTTCCTGCAGCCTTGTGATAAAGCAACTGTTAGCTT
GATA1_TS2:   CACCCCCCACCCTAATCAGAGGCCAAACCCTTCCTGCAGCCTTGTGATAAAGCAACTGTTAGCTTGCACTAGACTAGCTT
GATA1_TS3:   ATCAGAGGCCAAACCCTTCCTGCAATAAAGCAACTGTTAGCTTAGCTTGCACTAGACTAGCTT
GATA1_TS4:   ATCAGAGGCCAAACCCTTCCTGCAGCCTTGTGATAAAGCAACTGTTAGCTTGCACTAGACTAGCTTC
GATA1_TS5:   CCAGGGGTGAATTACAACTTTGCAAGCTAGTGCAAGCTAACAGTTGTTTATCAGGTCAGGTAGC
GATA1_TS6:   CACCCCCCACCCTAATCAGAGGCCAAACCCTTCCTGCAGCCTTGTGATAAAGCAACTGTTAGCTTGCACTACACT
GATA1_TS7:   GCTAGTCTAGTGCAAGCTAACAGTTGTTTATCAGAGCCTCAGGTCAGGTGGCTCTGATT
GATA1_TS8:   GCTAGTCTAGTGCAAGCTAACAGTTGTTTATCAGAGCTCAGGTCAGGTGGCCTCTGATTAGGGT
GATA1_TS9:   CCAGGTCTAGTGCAAGCTAACAGTTGTTTATCAGAGCTCAGGTCAGGTTGCAAGCTT
GATA1_TS10:  GCTAGTCTAGTGCAAGCTAACAGTTGTTTATCAGAGCTCAGGTCAGGTGGCCTCTGATTAGGGTGGGGC
GATA1_TS11:  GCTAGTCTAGTGCAAGCTAACAGTTGTTTATCAGAGCTCAGGTCAGGTGGCCTCTGATTAGGGTGGGGTGGGGT
GATA1_TS12:  GCTAGTCTAGTGCAAGCTAACAGTTGTTTATCAGAGCTCAGGTCAGGTGGCCTCTGATTAGGGTGGGGTGGGGT
```

*Figure 3*

| Number | Name | Cas9 | Guide-1 | Guide-2 | RNP | Volume | Glycerol buffer | EP buffer |
|---|---|---|---|---|---|---|---|---|
| | Master mix (1.1x) | 9.3775 | 4.2625 | 4.2625 | / | 17.9025 | / | / |
| 1 | Sp-Sa Cas9 | 4.4 | 2 | 2 | 80 pmol | 8.4 | 1.7 | / |
| 2 | Sp-Sa Cas9 | 2.2 | 1 | 1 | 40 pmol | 4.2 | 1.7 | / |
| 3 | Sp-Sa Cas9 | 1.1 | 0.5 | 0.5 | 20 pmol | 2.1 | 1.7 | / |
| 4 | Sp-Sa Cas9 | 0.55 | 0.25 | 0.25 | 10 pmol | 1.05 | 1.7 | / |
| 5 | Sp-Sa Cas9 | 0.275 | 0.125 | 0.125 | 5 pmol | 0.525 | 1.7 | / |
| 6 | Mock | / | / | / | / | / | 1.7 | / |
| | Master mix | 9.4 | 4 | 4 | / | 30 | / | 12.6 |
| 7 | Sp-Sa Cas9 | | | | 80 pmol | 15 | 1.7 | 0 |
| 8 | Sp-Sa Cas9 | | | | 40 pmol | 7.5 | 1.7 | 7.5 |
| 9 | Sp-Sa Cas9 | | | | 20 pmol | 3.75 | 1.7 | 11.25 |
| 10 | Sp-Sa Cas9 | | | | 10 pmol | 1.88 | 1.7 | 13.12 |
| 11 | Sp-Sa Cas9 | | | | 5 pmol | 0.94 | 1.7 | 14.06 |
| 12 | Mock | | | | / | / | 1.7 | 15 |

Erythroid differentiation, D18

Figure 8

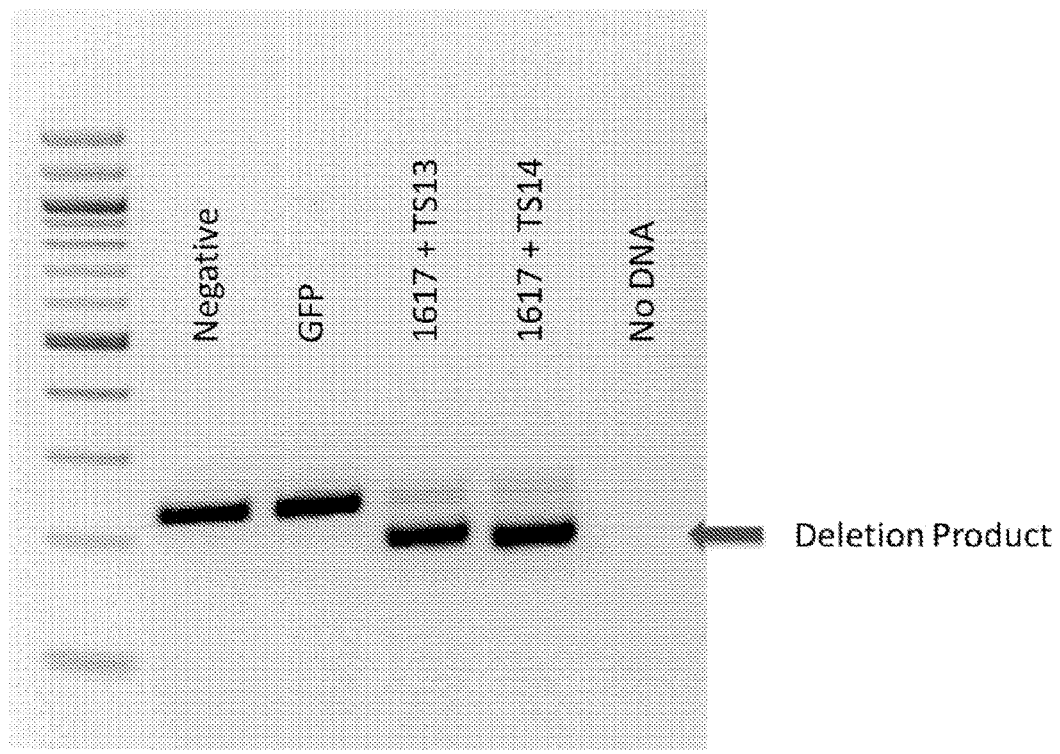

Figure 9

BCL11A Target Site PCR amplicon

GCCAGAAAAGAGATATGGCATCTACTCTTAGACATAACACACCAGGGTCAAT
ACAACTTTGAAGCTAGTCTAGTGCAAG<u>CTAACAGTTGCTTTTATCACA</u>GGCTC
CAGGAAGGGTTTG*GCCTCTGATTAGGGTGGGGGC*GTGGGTG*GGGT*AGAAGA
GGACTGGCAGACCTCTCCATCGGTGGCCGTTTGCCCAGGGGGGCCTCTTTCG
GAAGGCTCTCTTGGTGATGGAG

SpCas9 1617 target site underlined: PAM bold
    SaCas9 TS13 target site italics: PAM bold
    SaCas9 TS14 target site squiggle underline: PAM bold, italicized, and underlined
    TS13 and TS14 overlap

Figure 10

1617 Target:

CTAACAGTTGCTTTTATCAC

1617 sgRNA:
CUAACAGUUGCUUUUAUCACGUUUUAGAGCUAGAAAUAGCAAGUUAAAAUAAGGCUAGUCCGUUAUCAACUUGAAAAAGUGGCACCGAGUCGGUGCUUUU

TS13 Target:

GCCTCTGATTAGGGTGGGGGC

TS13 sgRNA:
GCCUCUGAUUAGGGUGGGGGCGUUUUAGUACUCUGGAAACAGAAUCUACUAAAACAAGGCAAAAUGCCGUGUUUAUCUCGUCAACUUGUUGGCGAGAUUU

TS14 Target:

TGATTAGGGTGGGGGCGTGGG

TS14 sgRNA:
UGAUUAGGGUGGGGGCGUGGGGUUUUAGUACUCUGGAAACAGAAUCUACUAAAACAAGGCAAAAUGCCGUGUUUAUCUCGUCAACUUGUUGGCGAGAUUU

*Figure 13*

Direction-1 Sp → PAM XXX PAM ↓ Nm
TCCCCGGCATCCTAGCGCGCTGGGCTAGCAATCGGCCTTCCGCGTCCCTTCCAACAGTACC Direction-2 Sp → PAM XXX Nm ↑ PAM
TCCCCGGCATCCTAGCGCGCTGGGCTAGCCGGTACTGTTGGAAGGACGCGGAAGGCGATT Direction-3 Nm → PAM XXX Sp ↑ PAM
GGTACTGTTGGAAGGACGCGGAGGCCGATTGCTAGCTCCCGGCATCCTAGCGCGCTGG Direction-4 PAM ↓ Nm XXX Sp ↑ PAM
AATCGCCTTCCCGCGTCCCTTCCAACAGTACCGCTAGCTCCCGGCATCCTAGCGCGCTGG

TARGETING BCL11A DISTAL REGULATORY ELEMENTS WITH A CAS9-CAS9 FUSION FOR FETAL HEMOGLOBIN REINDUCTION

CROSS REFERENCE TO RELATED APPLICATIONS

This application is a 35 U.S.C. § 371 National Phase Entry Application of International Application No. PCT/US2018/043073 filed Jul. 20, 2018, which designates the U.S. and claims benefit under 35 U.S.C. § 119(e) of U.S. Provisional Application No. 62/622,599 filed Jan. 26, 2018, the contents of which is incorporated herein by reference their entireties.

GOVERNMENT SUPPORT

This invention was made with Government support under Grant Nos R01GM115911 and R01AI117839 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Aug. 20, 2018, is named 701039-091500WOPT_SL.txt and is 54,211 bytes in size.

BACKGROUND

Normal adult hemoglobin comprises four globin proteins, two of which are alpha (a) proteins and two of which are beta (β) proteins. During mammalian fetal development, particularly in humans, the fetus produces fetal hemoglobin, which comprises two gamma (γ)-globin proteins instead of the two β-globin proteins. During the neonatal period, a globin switch occurs, referred to as the "fetal switch", at which point, erythroid precursors switch from making predominantly γ-globin to making predominantly β-globin. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth until HbA becomes predominant. This switch results primarily from decreased transcription of the gamma-globin genes and increased transcription of beta-globin genes. On average, the blood of a normal adult contains less than 1% HbF, though residual HbF levels have a variance of over 20 fold in healthy adults and are genetically controlled.

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickle) hemoglobin (HbS). HbS is prone to polymerization, particularly under deoxygenated conditions. HbS RBCs are more fragile than normal RBCs and undergo hemolysis more readily, leading eventually to anemia.

Recently, the search for treatment aimed at reduction of globin chain imbalance or predisposition to hemoglobin polymerization in patients with β-hemoglobinopathies has focused on the pharmacologic manipulation of fetal hemoglobin ($\alpha_2\gamma_2$; HbF). The therapeutic potential of such approaches is suggested by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease. It is now accepted that hemoglobin disorders, such as sickle cell anemia and the β-thalassemias, are ameliorated by increased HbF production.

As mentioned earlier, the switch from fetal hemoglobin to adult hemoglobin ($\alpha_2\gamma_2$; HbA) usually proceeds within six months after parturition. However, in the majority of patients with β-hemoglobinopathies, the upstream γ globin genes are intact and fully functional, so that if these genes become reactivated, functional hemoglobin synthesis could be maintained during adulthood, and thus ameliorate disease severity. Unfortunately, the in vivo molecular mechanisms underlying the globin switch are not well understood.

Evidence supporting the feasibility of reactivation of fetal hemoglobin production comes from experiments in which it was shown that peripheral blood, containing clonogenic cells, when given the appropriate combination of growth factors, produce erythroid colonies and bursts in semisolid culture. Individual cells in such colonies can accumulate fetal hemoglobin (HbF), adult hemoglobin (HbA) or a combination of both. In cultures from adult blood, nucleated red cells accumulate either HbA (F−A+) only, or a combination of HbF and HbA (F+A+). Importantly, individual colonies contain both F+ and F− cells, indicating that both types are progeny from the same circulating stem cells. Thus, during the early stages of development in culture, cells execute an option, through currently unknown mechanisms, whether or not to express HbF. The proportion of adult F+ cells developing in culture does not appear to be preprogrammed in vivo, but appears to depend on culture conditions: A shift into the combined HbF and HbA expression pathway can, for example, be achieved in vitro by high serum concentrations, due to the activity of an unidentified compound that can be absorbed on activated charcoal.

Overall, identification of molecules that play a role in the globin switch is important for the development of novel therapeutic strategies that interfere with adult hemoglobin and induce fetal hemoglobin synthesis. Such molecules would provide new targets for the development of therapeutic interventions for a variety of hemoglobinopathies in which reactivation of fetal hemoglobin synthesis would significantly ameliorate disease severity and morbidity.

SUMMARY

Provided herein are methods and compositions for increasing fetal β-globin levels in a cell by disrupting BCL11A expression at the genomic level. Also provided herein are methods and compositions relating to the treatment of hemoglobinopathies by reinduction of fetal β-globin levels.

One aspect of the invention described herein provides a method for producing a progenitor cell having decreased BCL11A mRNA or protein expression comprising contacting an isolated progenitor cell with an agent that deletes the GATA1 binding element in the functional core of the BCL11A enhancer +58 kb, wherein the agent is a composition comprising a fusion protein comprising at least two DNA-targeting endonucleases, or the agent is a composition comprising a vector carrying the coding sequence of a fusion protein comprising at least two DNA-targeting endonucleases whereby the DNA-targeting endonuclease fusion protein makes precise cleavages near the targeted GATA1 binding element to delete it, thereby reducing the mRNA or protein expression of BCL11A.

In one embodiment of this aspect, and all other aspects, the agent disrupts the GATA1 binding element in the functional core of the BCL11A enhancer +58 kb. As used herein, "disrupts" refers to the disruption of its expression, e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity, decrease, prevent, delay activation, inactivate, desensitize, or down regulate the activity of a polypeptide or polynucleotide encoding the GATA1 binding element. Disruption can be direct or indirect.

Another aspect of the invention described herein provides a method for producing an isolated genetic engineered human cell having at least one genetic modification comprising; contacting an isolated cell with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element to delete it, thereby causing at least one genetic modification therein.

Another aspect of the invention described herein provides a method of increasing fetal hemoglobin levels in a cell, the method comprising; contacting an isolated cell with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element to delete it, thereby causing at least one genetic modification therein, whereby fetal hemoglobin expression is increased in said cell, or its progeny, relative to said cell prior to said contacting.

Another aspect of the invention described herein provides a method for increasing fetal hemoglobin levels in a mammal in need thereof, the method comprising; contacting an isolated hematopoietic progenitor cell in said mammal with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element, thereby causing at least one genetic modification therein, whereby fetal hemoglobin expression is increased in said mammal, relative to expression prior to said contacting.

In one embodiment of any aspect, the isolated progenitor cell or isolated cell is a hematopoietic progenitor cell.

In one embodiment of any aspect, the hematopoietic progenitor is a cell of the erythroid lineage.

In one embodiment of any aspect, the isolated progenitor cell or isolated cell is a human cell.

In one embodiment of any aspect, the isolated progenitor cell or isolated cell is a CD34+ cell.

In one embodiment of any aspect, the isolated progenitor cell or isolated cell is an induced pluripotent stem cell.

In one embodiment of any aspect, the hematopoietic progenitor cell is contacted ex vivo or in vitro.

In one embodiment of any aspect, the at least one genetic modification is a deletion. In one embodiment of any aspect, the deletion removes the entire region or a portion of the targeted GATA1 binding element. In one embodiment, the GATA1 binding element comprises, consists of, or consists essentially of SEQ ID NO: 1.

In one embodiment of any aspect, the agent composition further comprises guideRNA. In one embodiment of any aspect, the guideRNA comprises, consists of, or consists essentially of a sequence selected from SEQ ID NOs 2-9.

Another aspect of the invention described herein provides an isolated genetic engineered human cell having at least one genetic modification on chromosome 2 location 60,716, 189-60,728,612, near the GATA1 binding element in the functional core of the BCL11A enhancer +58 kb generated by any of the methods described herein.

Another aspect of the invention described herein provides a composition comprising isolated genetic engineered human cells described herein.

Another aspect of the invention described herein provides a method for increasing fetal hemoglobin levels in a mammal in need thereof, the method comprising transplanting an isolated genetic engineered human cell or a composition described herein into the mammal.

In one embodiment of any aspect, the mammal has been diagnosed with a hemoglobinopathy.

In one embodiment of any aspect, the hemoglobinopathy is a β-hemoglobinopathy.

In one embodiment of any aspect, the hemoglobinopathy is sickle cell disease.

In one embodiment of any aspect, the hemoglobinopathy is β-thalassemia.

Another aspect of the invention described herein provides a method of treatment of a hemoglobinopathy in a subject comprising; administering an effective amount of a composition comprising isolated genetic engineered human cells described herein, and whereby fetal hemoglobin expression is increased in the subject relative to prior treatment.

In one embodiment of any aspect, the subject has been diagnosed with a hemoglobinopathy.

In one embodiment of any aspect, the method further comprises selecting a subject who has been diagnosed with a hemoglobinopathy.

Another aspect of the invention described herein provides a method of treatment of a hemoglobinopathy in a subject comprising; administering an effective amount of a composition comprising hematopoietic progenitor cells to the subject, wherein the hematopoietic progenitor cells have been contacted ex vivo or in vitro with an effective amount of a composition comprising a fusion protein comprising at least two DNA-targeting endonucleases, or a composition comprising a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, and whereby fetal hemoglobin expression is increased in the subject relative to prior treatment.

In one embodiment of any aspect, the composition further comprises a pharmaceutically acceptable carrier or diluent.

In one embodiment of any aspect, the composition is administered by injection, infusion, instillation, or ingestion.

In one embodiment of any aspect, the mammal or subject is further administered an epigenetic modifier.

In one embodiment of any aspect, the mammal or subject or isolated cells are human or derived from a human.

In one embodiment of any aspect, the isolated progenitor cell or isolated cell is a hematopoietic progenitor cell.

In one embodiment of any aspect, the isolated progenitor cell or isolated cell is a human cell.

In one embodiment of any aspect, the isolated progenitor cell is a CD34+ cell.

Another aspect of the invention described herein provides a composition comprising a CD34+ hematopoietic progenitor cell that comprises a fusion protein comprising at least two DNA-targeting endonucleases, or the CD34+ hematopoietic progenitor cell comprises a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, and thereby reduces the mRNA or protein expression of BCL11A in the cell. In one embodiment of any aspect, the composition further comprises a pharmaceutically acceptable carrier or diluent, and/or an epigenetic modifier.

In one embodiment of any aspect, the CD 34+ hematopoietic progenitor cell is expanded ex vivo.

In one embodiment of any aspect, the CD 34+ hematopoietic progenitor cell is formulated for injection or infusion.

Another aspect of the invention described herein provides a population of CD34+ hematopoietic progenitor cells, wherein the CD34+ hematopoietic progenitor cells comprise a fusion protein comprising at least two DNA-targeting endonucleases, or the CD34+ hematopoietic progenitor cells comprise a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, thereby reducing the mRNA or protein expression of BCL11A in the cells.

In one embodiment of any aspect, the population of CD34+ hematopoietic progenitor cells further comprise a pharmaceutically acceptable carrier or diluent.

In one embodiment of any aspect, the population of CD34+ hematopoietic progenitor cells further comprise an epigenetic modifier.

In one embodiment of any aspect, the CD 34+ hematopoietic progenitor cell is expanded ex vivo.

In one embodiment of any aspect, the CD 34+ hematopoietic progenitor cell is formulated for injection or infusion.

In one embodiment of any aspect, the compositions or methods described herein further comprise an epigenetic modifier.

In one embodiment of any aspect, the fusion protein comprising at least two DNA-targeting endonucleases comprising a first Cas9 or Cas12a nuclease, said nuclease comprising a protospacer adjacent motif recognition domain and a peptide linker, wherein said peptide linker is attached to a second Cas9 or Cas12a nuclease.

In one embodiment of any aspect, the Cas9 nuclease of the fusion protein is selected from the group consisting of SpCas9, SaCas9, NmCas9, CjCas9, and AnCas9.

In one embodiment of any aspect, the Cas9 nuclease of the fusion protein is selected from the group consisting of FnCas12a, LbCas12a, and AsCas12a.

In one embodiment of any aspect, the protospacer adjacent motif recognition domain of fusion protein is selected from the group consisting of SpCas9, SpCas9$^{MT1}$ SpCas9$^{MT2}$, SpCas9$^{MT3}$, NmCas9$^{SM}$ and NmCas9$^{DM}$.

In one embodiment of any aspect, the protospacer adjacent motif recognition domain of fusion protein is mutated or non-mutated.

In one embodiment of any aspect, the peptide linker of fusion protein is a peptide linker. In one embodiment of any aspect, the peptide linker is between twenty-five and eighty amino acids.

In one embodiment of any aspect, the fusion protein further comprises a guide RNA which is attached to a guide sequence element.

In one embodiment of any aspect, the mutated protospacer adjacent motif recognition domain of the fusion protein comprises mutated DNA phosphodiester recognition amino acid residues.

In one embodiment of any aspect, the guide RNA of said fusion protein is selected from the group consisting of an sgRNA sequence, a crRNA sequence and a tracrRNA sequence. In one embodiment of any aspect, the guide sequence element of said guide RNA of said fusion protein is truncated. In one embodiment of any aspect, the truncated guide sequence element is less than twenty nucleotides

BRIEF DESCRIPTION OF DRAWINGS

FIGS. 1A-1B show comparison of the different Cas9-DTU frameworks. FIG. 1A shows the original Cas9MT-DTU system where the pDBD is either a zinc finger protein or a TALE array. FIG. 1B describes the Cas9-Cas9 fusion where DNA binding and cleavage by SpCas9MT is facilitated by direct linkage to NmCas9. The NmCas9 module can be nuclease-dead (dNmCas9) or active. If active, it can create precise deletions between the Cas9 cleavage sites with high efficiency.

FIGS. 2A-2F show the assessment of the activity profiles of nucleases that are targeting the GATA1 binding element in BCL11A enhancer +58 kb. FIG. 2A shows the lesion rates and types are determined by deep sequencing. Single nucleases generate small indels at their corresponding cleavage sites, whereas dual nucleases (independent, fusionWT, or fusionMT) may generate six types of lesion products. FIG. 2B shows the ratios of precise deletions relative to other types of lesions for each nuclease and target site. FIG. 2C-2E shows an overview of the nuclease activities at 12 GATA1 target sites: FIG. 2C shows the total lesion rates, FIG. 2D shows the precise deletion rates, and FIG. 2E shows the fraction of precise deletions among all lesions. Each Box plot is drawn by GraphPad Prism, where the box represents 25th and 75th percentile and the middle line is the median. Whiskers and outliers are defined by the Tukey method. Statistical significance is determined by one-way analysis of variance (ANOVA), "*", "*" and "**" denote P<0.05, P<0.001 and P<0.0001 respectively. Deep sequencing data are from three independent biological replicates performed on different days in HEK293T cells. Error bars indicate ±s.e.m. (FIG. 2F) Target site information of Cas9-Cas9 fusions for deletion of GATA1 binding element in the functional core of the BCL11A enhancer +58 kb (highlighted in gray). The SpCas9 protospacer is bold underlined with its PAM element, the SaCas9 protospacer is double underlined with its PAM element, and the NmCas9 protospacer is wavy underlined with its PAM element. FIG. 2F discloses SEQ ID NOS 201-208, 205, 209-210 and 210, respectively, in order of appearance.

FIG. 3 shows a table of SpCas9-SaCas9 RNP complex mixing parameters and titrations for BCL11A TS9 editing in CD34+ HSCs.

FIG. 8 shows 40 pmol SpCas9-SaCas9+100 pmol sgRNA. The arrow indicates the deletion product at TS13 and TS14 target sites.

FIG. 9 shows BCL11A Target Site PCR amplicon. The SpCas9 1617 target site underlined. The SaCas9 TS13 target site is show in italics and the TS14 target site is squiggle underlined. FIG. 9 discloses SEQ ID NO: 211.

FIG. 10 shows 1617 target and sgRNA sequences, the TS13 target and sgRNA sequences, and the TS14 target and sgRNA sequences. FIG. 10 discloses SEQ ID NOS 212-217, respectively, in order of appearance.

FIG. 13 shows sequence of four different configurations with various spacing. FIG. 13 discloses SEQ ID NOS 218-221, respectively, in order of appearance.

FIG. 15 discloses SEQ ID NOS 222-223, respectively, in order of appearance.

FIG. 16 discloses SEQ ID NOS 223-225, respectively, in order of appearance.

FIG. 18 discloses SEQ ID NOS 226, 226, 226, 226 and 226, respectively, in order of appearance.

FIG. 19 discloses SEQ ID NOS 207, 205, 209 and 210, respectively, in order of appearance.

DETAILED DESCRIPTION

Figure 2A:
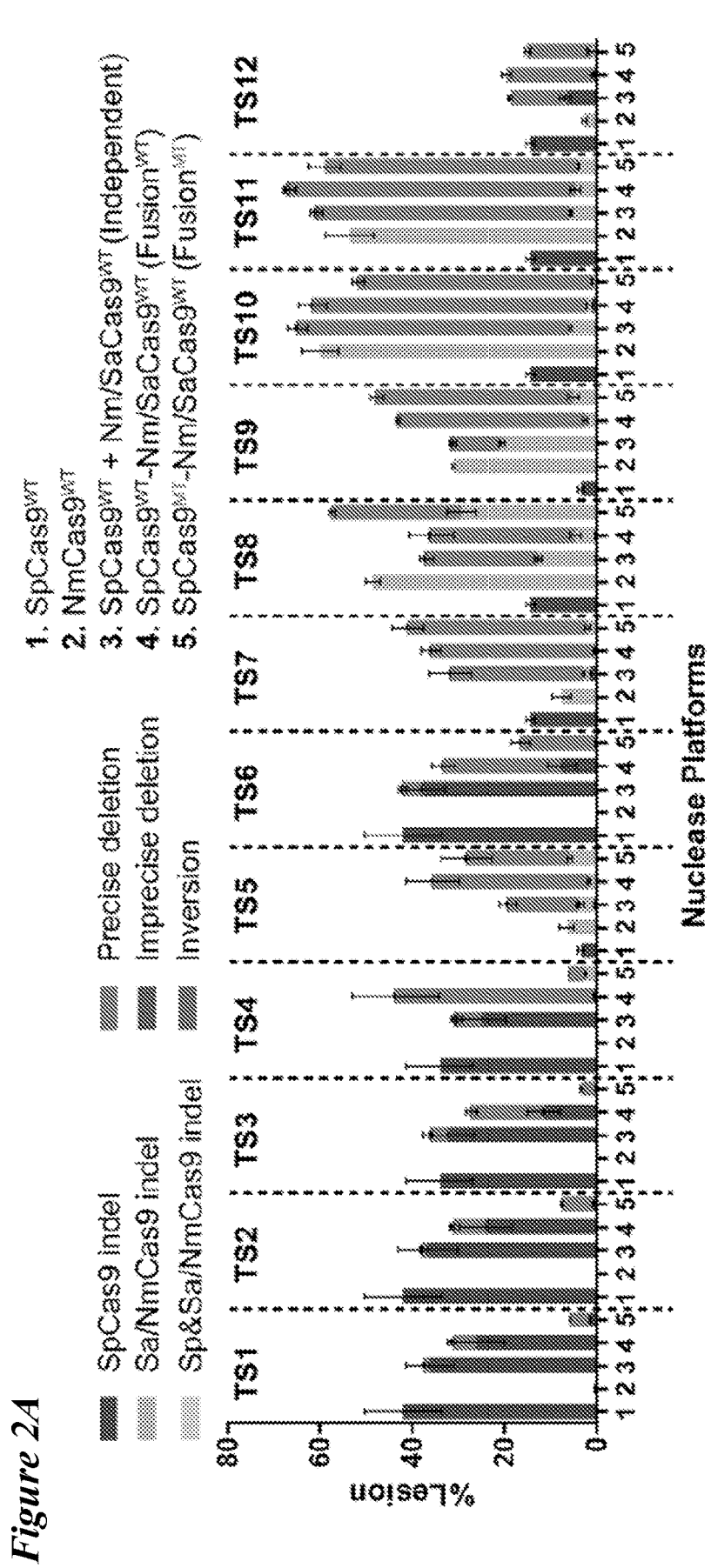
Figure 2B:
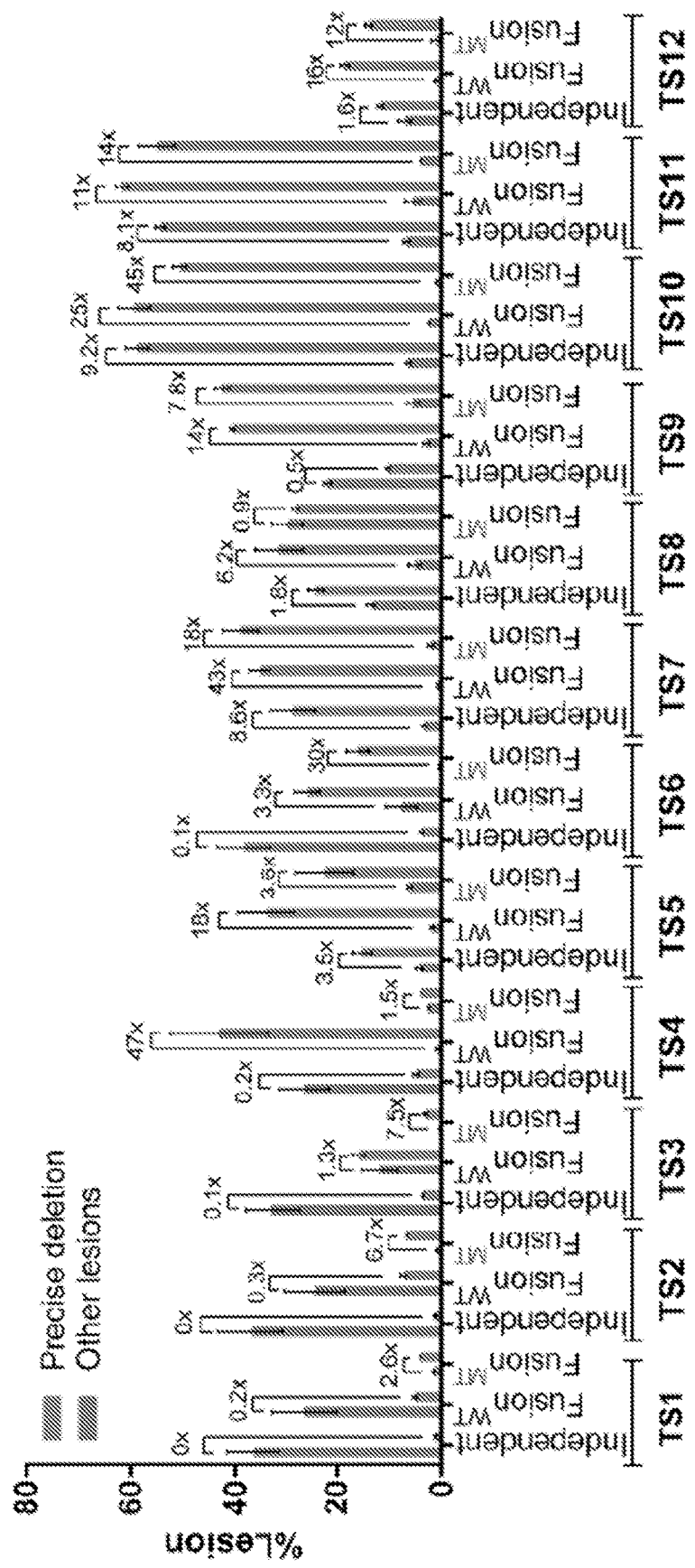
Figure 2C:
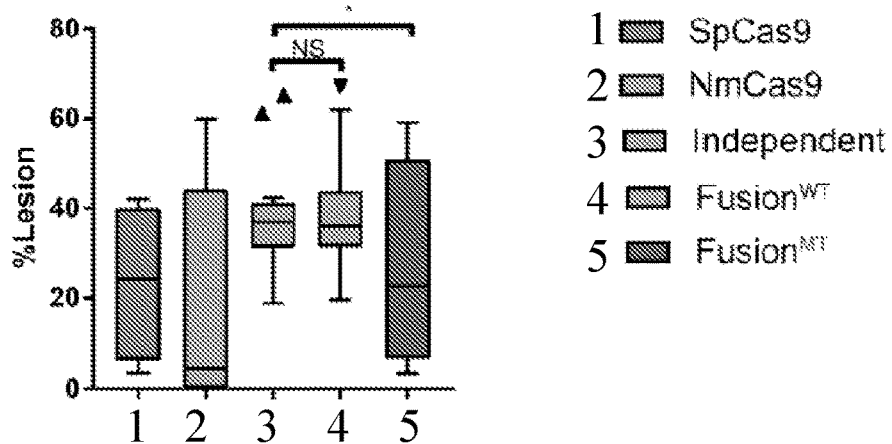
Figure 2D:
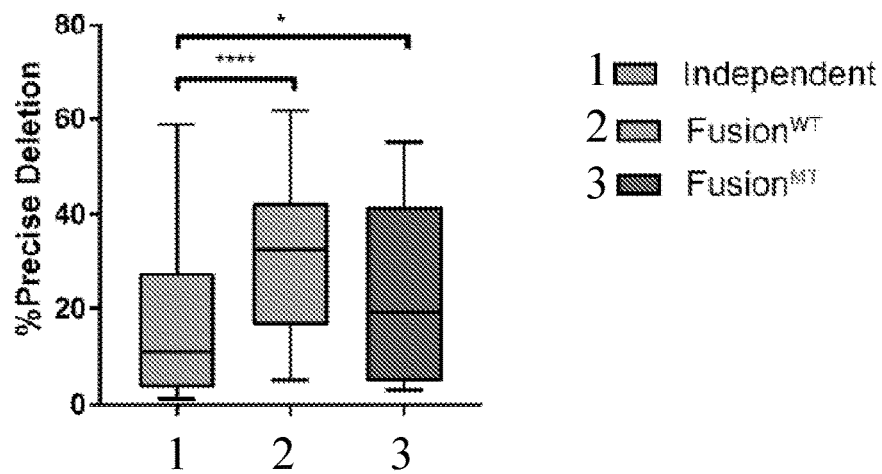
Figure 2E:
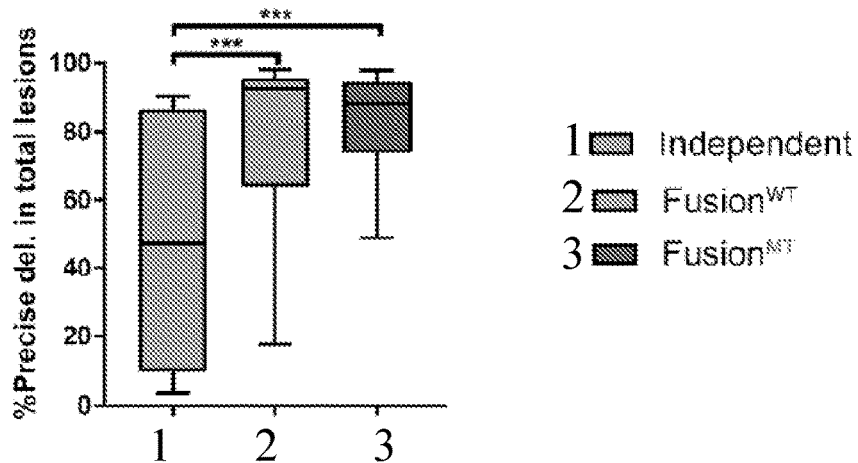

The methods and compositions described herein relate, in part, to the discovery of a distal regulatory region upstream of the BCL11A gene that can regulate expression of the BCL11A protein. The BCL11A protein acts as a stage specific regulator of fetal hemoglobin expression by repressing γ-globin induction. Accordingly, the methods and compositions provided herein are novel methods for the regulation of γ-globin expression in erythroid cells. More specifically, these activities can be harnessed in methods for the treatment of β-hemoglobinopathies by induction of γ-globin via inhibition of the BCL11A gene product.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

One aspect provided herein relates to a method for producing a progenitor cell having decreased BCL11A mRNA or protein expression comprising contacting an isolated progenitor cell with an agent that deletes the GATA1 binding element in the functional core of the BCL11A enhancer +58 kb, wherein the agent is a composition comprising a fusion protein comprising at least two DNA-targeting endonucleases, or the agent is a composition comprising a vector carrying the coding sequence of a fusion protein comprising at least two DNA-targeting endonucleases whereby the DNA-targeting endonuclease fusion protein makes precise cleavages near the targeted GATA1 binding element to delete it, thereby reducing the mRNA or protein expression of BCL11A.

In one embodiment, a composition consists of a fusion protein comprising at least two DNA-targeting endonucleases, or a composition consists of a vector carrying the coding sequence of a fusion protein comprising at least two DNA-targeting endonucleases.

In one embodiment, the composition consists essentially of a fusion protein comprising at least two DNA-targeting endonucleases, or a composition consists essentially of a vector carrying the coding sequence of a fusion protein comprising at least two DNA-targeting endonucleases.

As used herein, "precise cleavages near the targeted GATA1 binding element" refers to precise cleavages within at least 100 base pairs of the start of the GATA1 binding element. The precise cleavages can be with 100 base pairs upstream or downstream of the start or end of the GATA1 binding element, respectively. The precise cleavages can be within at least 95, at least 90, at least 85, at least 80, at least 75, at least 70, at least 65, at least 60, at least 55, at least 50, at least 45, at least 40, at least 35, at least 30, at least 25, at least 20, at least 15, at least 10, at least 5, at least 4, at least 3, at least 2, at least 1, or less base pairs of the start or end of the GATA1 binding element. If at least two precise cleavages are made, the at least two precise cleavages can all be present upstream of the GATA1 binding element, downstream of the GATA1 binding element, or can be present both upstream and downstream of the GATA1 binding element.

Another aspect provided herein relates to a method for producing an isolated genetic engineered human cell having at least one genetic modification comprising contacting an isolated cell with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element to delete it, thereby causing at least one genetic modification therein.

Another aspect provided herein relates to a method of increasing fetal hemoglobin levels in a cell comprising contacting an isolated cell with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element to delete it, thereby causing at least one genetic modification therein, whereby fetal hemoglobin expression is increased in said cell, or its progeny, relative to said cell prior to said contacting.

Another aspect provided herein relates to a method for increasing fetal hemoglobin levels in a mammal in need thereof comprising contacting an isolated hematopoietic progenitor cell in said mammal with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element, thereby causing at least one genetic modification therein, whereby fetal hemoglobin expression is increased in said mammal, relative to expression prior to said contacting.

Another aspect provided herein relates to an isolated genetic engineered human cell having at least one genetic modification on chromosome 2 location 60,716,189-60,728, 612, (according to UCSC Genome Browser hg 19 human genome assembly) near the GATA1 binding element in the functional core of the BCL11A enhancer +58 kb generated by any method described herein. In one embodiment, the decrease of BCL11A mRNA or protein expression is achieved by causing at least one genetic modification at the genomic DNA of the cell on chromosome 2 location 60,716, 189-60,728,612 that results in epigenetic modification of the genetic function at chromosome 2 location 60,716,189-60, 728,612. In this embodiment, the BCL11A enhancer activity located within this chromosome 2 location 60,716,189-60, 728,612 is reduced. By decrease in this aspect, the enhancer activity in enhancing BCL11A mRNA or protein expression in the cell is at least 5% lower, at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein. By decrease of the BCL11A mRNA or protein expression in the cell means that protein expression is at least 5% lower, at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

Another aspect provided herein relates to a composition comprising isolated genetic engineered human cells described herein.

Another aspect provided herein relates to a method for increasing fetal hemoglobin levels in a mammal in need thereof, the method comprising transplanting an isolated genetic engineered human cell or a composition described herein into the mammal.

Another aspect provided herein relates to a method of treatment of a hemoglobinopathy in a subject comprising; administering an effective amount of a composition comprising isolated genetic engineered human cells described herein, and whereby fetal hemoglobin expression is increased in the subject relative to prior treatment.

Another aspect provided herein relates to a method of treatment of a hemoglobinopathy in a subject comprising administering an effective amount of a composition comprising hematopoietic progenitor cells to the subject, wherein the hematopoietic progenitor cells have been contacted ex vivo or in vitro with an effective amount of a composition comprising a fusion protein comprising at least two DNA-targeting endonucleases, or a composition comprising a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, and whereby fetal hemoglobin expression is increased in the subject relative to prior treatment.

Another aspect provided herein relates to a composition comprising a CD34+ hematopoietic progenitor cell that comprises a fusion protein comprising at least two DNA-targeting endonucleases, or the CD34+ hematopoietic progenitor cell comprises a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, and thereby reduces the mRNA or protein expression of BCL11A in the cell.

Another aspect provided herein relates to a population of CD34+ hematopoietic progenitor cells, wherein the CD34+ hematopoietic progenitor cells comprise a fusion protein comprising at least two DNA-targeting endonucleases, or the CD34+ hematopoietic progenitor cells comprise a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, thereby reducing the mRNA or protein expression of BCL11A in the cells.

In one embodiment of this aspect, and all other aspects, the isolated progenitor cell or isolated cell is a hematopoietic progenitor cell, a human cell, a CD34+, or an induced pluripotent stem cell.

In one embodiment of this aspect, and all other aspects, the hematopoietic progenitor is a cell of the erythroid lineage. Methods of isolating hematopoietic progenitor cell are well known in the art, e.g., by flow cytometric purification of CD34+ or CD133+ cells, microbeads conjugated with antibodies against CD34 or CD133, markers of hematopoietic progenitor cell. Commercial kits are also available, e.g., MACS® Technology CD34 MicroBead Kit, human, and CD34 MultiSort Kit, human, and STEMCELL™ Technology EasySep™ Mouse Hematopoietic Progenitor Cell Enrichment Kit.

In another embodiment of this aspect and all other aspects described herein, the hematopoietic progenitor cell, the isolated human cell, or isolated cell is contacted ex vivo or in vitro.

In one embodiment of this aspect, and all other aspects, the at least one genetic modification is a deletion. An epigenetic modification can indirectly or directly affect the location on the chromosome which it resides. "Indirect affect" refers to long distance effects of epigenetic modification in the genomic DNA of the cell on chromosome. In one embodiment of this aspect, and all other aspects, the deletion removes the entire region or a portion of the targeted GATA1 binding element.

In one embodiment of this and all other aspects described herein, the GATA1 binding element site is at chr2:60,495,264-60,495,271 in genome version hg38. In one embodiment, the GATA1 binding element comprises, consists of, or consists essentially of SEQ ID NO: 1. The GATA1 binding motif is further described in, e.g., Canver, M. C. et al. BCL11A enhancer dissection by Cas9-mediated in situ saturating mutagenesis. *Nature* 527, 192-197 (2015), which is incorporated herein by reference in its entirety.

SEQ ID NO: 1 is a nucleic acid sequence that encodes the GATA1 binding element. Within SEQ ID NO: 1, W=A or T and R=G or A

WGATAAR, (SEQ ID NO: 1)

In one embodiment of this and all other aspects described herein, the deletion is of other functional sequences with the +58 BCL11A enhancer genomic region.

In another embodiment of this aspect and all other aspects described herein, the deletion comprises one or more of the DNAse 1-hypersensitive sites (DHS) +62, +58, and +55 as described herein in the Examples section, in Table 1, and further in, e.g., Canver, M. C. et al. BCL11A enhancer dissection by Cas9-mediated in situ saturating mutagenesis. *Nature* 527, 192-197 (2015), which is incorporated herein by reference in its entirety. In another embodiment of this aspect and all other aspects described herein, the deletion consists essentially of one or more of the DNAse 1-hypersensitive sites (DHS) +62, +58, and +55 as described herein in the Examples section. In another embodiment, the deletion consists of one or more of the DNAse 1-hypersensitive sites (DHS) +62, +58, and +55 as described herein in the Examples section.

In another embodiment of this aspect and all other aspects described herein, the epigenetic modification comprises or affects one or more of the DNAse 1-hypersensitive sites (DHS) +62, +58, and +55 as described herein in the Examples section. As used herein, the phrase "affects one or more of the DNAse 1-hypersensitive sites" means natural function of these DNAse 1-hypersensitive sites (DHS) +62, +58, and +55 are reduce, for example, access to transcription factors or DNA degradation enzymes such as DNase I. In general, DNase I hypersensitive sites (DHSs) are regions of chromatin which are sensitive to cleavage by the DNase I enzyme. In these specific regions of the genome, chromatin has lost its condensed structure, exposing the DNA, and making it accessible. This raises the availability of DNA to degradation by enzymes, like DNase I. These accessible chromatin zones are functionally related to transcriptional activity, since this remodeled state is necessary for the binding of proteins such as transcription factors. Accordingly, the epigenetic modification contemplated herein results in reduced access to DNA degradation enzymes that is at least 5% lower, at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

In another embodiment of this aspect and all other aspects described herein, the deletion comprises one or more of the SNP markers described in Table 2. In another embodiment of this aspect and all other aspects described herein, the deletion consists essentially of one or more of the SNP markers described in Table 2. In another embodiment of this aspect and all other aspects described herein, the deletion consists of one or more of the SNP markers described in Table 2.

In another embodiment of this aspect and all other aspects described herein, the epigenetic modification comprises or affects one or more of the SNP markers described in Table 2. As used herein, the phrase "affects one or more of the SNP markers" means natural function(s) of these SNPs are to reduce, for example, access to transcription factors. For example, methylation of these SNPs would reduce the binding of transcription factors, leading to reduced mRNA or protein expression of BCL11A.

In another embodiment of this aspect and all other aspects described herein, the deletion comprises one or more of the fragments listed in Table 7. In another embodiment of this aspect and all other aspects described herein, the deletion consists essentially of one or more of the fragments listed in Table 7. In another embodiment of this aspect and all other aspects described herein, the deletion consists of one or more of the fragments listed in Table 7. In another embodiment of this aspect and all other aspects described herein, the deletion is from 60,716,189 to 60,728,612, from 60,716,189 to 60,723,870, from 60,722,992 to 60,728,612, from 60,717,236 to 60,719,036, from 60,722,006 to 60,723,058, from 60,724,917 to 60,726,282, from 60,616,396 to 60,618,032, from 60,623,536 to 60,624,989, from 60,626,565 to 60,628,177, from 60,717,236 to 60,719,036, from 60,721,212 to 60,722,958, from 60,724,780 to 60,726,471, from 60,739,075 to 60,740,154, from 60,748,003 to 60,749,009, from 60,826,438 to 60,827,601, or from 60,831,589 to 60,833,556.

In another embodiment of this aspect and all other aspects described herein, the epigenetic modification comprises or affects one or more of the fragments listed in Table 7. As used herein, the phrase "affects one or more of the fragments listed in Table 7" means natural function(s) of these fragments are reduce, for example, access to transcription factors. For example, methylation of these fragments would reduce the binding of transcription factors, leading to reduced mRNA or protein expression of BCL11A.

In another embodiment of this aspect and all other aspects described herein, the epigenetic modification is from 60,716,189 to 60,728,612, from 60,716,189 to 60,723,870, from 60,722,992 to 60,728,612, from 60,717,236 to 60,719,036, from 60,722,006 to 60,723,058, from 60,724,917 to 60,726,282, from 60,616,396 to 60,618,032, from 60,623,536 to 60,624,989, from 60,626,565 to 60,628,177, from 60,717,236 to 60,719,036, from 60,721,212 to 60,722,958, from 60,724,780 to 60,726,471, from 60,739,075 to 60,740,154, from 60,748,003 to 60,749,009, from 60,826,438 to 60,827,601, or from 60,831,589 to 60,833,556.

In another embodiment of this aspect and all other aspects described herein, the deletion removes the entire region between chromosome 2 location 60,716,189-60,728,612 or removes a portion of the region resulting in disruption of one of more DNAse 1-hypersensitive sites (DHS). As used herein, the term "disruption" refers to a decrease in erythroid transcription of BCL11A in a cell comprising a disruption of one or more DNAse-1 hypersensitive sites by at least 10% (e.g., at least 20%, at least 30%, at least 40%, at least 50%, at least 60%, at least 70%, at least 80%, at least 90%, at least 95%, at least 99% or even 100% (i.e., no detectable erythroid transcription)) compared to a cell not having such a disruption. In one embodiment, the disruption comprises an inability of a modified DNAse-1hypersensitive site to bind to its native transcription factors (e.g., GATA1 and TAL1).

In another embodiment of this aspect and all other aspects described herein, the epigenetic modification that interferes with the establishment and/or maintenance of the epigenetic signature at the enhancer region on chromosome 2 location 60,716,189-60,728,612 (according to UCSC Genome Browser hg 19 human genome assembly) thereby leading to reduced mRNA or protein expression of BCL11A, and increasing fetal hemoglobin expression in the mammal.

In one embodiment of this aspect and all other aspects described herein, the epigenetic modification that interferes with the establishment and/or maintenance of the epigenetic signature at the enhancer region on chromosome 2 location 60,716,189-60,728,612 (according to UCSC Genome Browser hg 19 human genome assembly) includes but is not limited to epigenetic modifications that affects DNase I sensitivity, epigenetic modifications that affects histone modifications, epigenetic modifications that affects GATA1/TAL1 binding, and epigenetic modifications that affects long-range promoter interaction of the promoter of BCL11A.

For example, an epigenetic modification that interferes with the establishment and/or maintenance of the epigenetic signature at the enhancer region on chromosome 2 location 60,716,189-60,728,612 include but is not limited to at least one deletion within chromosome 2 location 60,716,189-60,728,612 such that the overall function of this region is affected whereby the mRNA and expression of BCL11A is reduced or decreased. For example, the deletion is at the DNaseI sensitivity regions chromosome 2 location 60,716,189-60,728,612, e.g., +62, +58, and +55. The deletion could be at +62 or +58 or +55 or combination thereof. For examples, at +62 and +58, +58 and +55, +62 and +55, or at all three +62, +58, and +55.

As another example, an epigenetic modification that interferes with the establishment and/or maintenance of the epigenetic signature at the enhancer region on chromosome 2 location 60,716,189-60,728,612 include but is not limited to changes in the histone modifications on chromosome 2 that is not at location 60,716,189-60,728,612, or changes in the histone modifications on chromosome 2 at location 60,716,189-60,728,612, or both histone modifications on chromosome 2 not at location 60,716,189-60,728,612 as well as at at location 60,716,189-60,728,612 such that the overall function of this region is affected whereby the mRNA and expression of BCL11A is reduced or decreased.

In another embodiment, an epigenetic modification that interferes with the establishment and/or maintenance of the epigenetic signature at the enhancer region on chromosome 2 location 60,716,189-60,728,612 include but is not limited to an insertion of at least one engineered specific-repressor sequence that change the epigenetic features of noncoding elements at chromosome 2 location 60,716,189-60,728,612 and thus result in repression of target gene expression. The first is specifically focused on epigenetically repressing individual enhancers. In other words, insertion of engineered specific-repressor sequences into chromosome 2 would prospectively interfering with epigenetic modification at the BCL11A erythroid enhancer which eventually leads to reduced BCL11A gene expression.

Any methods known in the art can be used to produce the epigenetic modification contemplated. For example, as described in Mendenhall E. M. et al., Nat. Biotechnol. 8 Sep. 2013, and Maeder M L et al., Nat Biotechnol. 9 Oct. 2013 2013.

In one embodiment of this aspect and all other aspects described herein, the insertion of at least one engineered specific-repressor sequence on any location chromosome 2 results in but is not limited to reduced DNaseI sensitivity regions at chromosome 2 location 60,716,189-60,728,612, e.g., +62, +58, and +55; increased histone modifications on chromosome 2 location 60,716,189-60,728,612; reduced transcription factors binding to the GATA1/TAL1 of the enhancer region on chromosome 2 location 60,716,189-60,728,612; and reduced or weakened interaction between the chromosome 2 location 60,716,189-60,728,612 with the BCL11A promoter.

In one embodiment of this aspect and all other aspects described herein, the overall effects of the insertion of at least one engineered specific-repressor sequence on any location chromosome 2 is reduced or decreased mRNA and expression of BCL11A.

In some embodiments, as used in the context of mRNA and expression of BCL11A, interaction between the chromosome 2 location 60,716,189-60,728,612 or BCL11A enhancer with the BCL11A promoter, and transcription factors binding to the GATA1/TAL1 of the enhancer region, the term "reduced" or "decreased" refers to at least 5% lower, at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to the control situation that is in the absence of the epigenetic modification or insertion of engineered sequences disclosed herein. By decrease of the BCL11A mRNA or protein expression in the cell means that protein expression is at least 5% lower, at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that does not have the epigenetic modification or insertion of engineered sequences disclosed herein.

In one embodiment of this aspect and all other aspects described herein, the insertion of at least one engineered specific-repressor sequence occurs within the DNaseI sensitivity regions of chromosome 2 location 60,716,189-60,728,612, e.g., +62, +58, and +55. The insertion could be at the 5'end of +62 or +58 or +55 or at the 3'end of +62 or +58 or +55, or between +62 and +58, or between +58 and +55, or between +55 and +62.

In one embodiment of this aspect and all other aspects described herein, the insertion of at least one engineered specific-repressor sequence changes the DNaseI sensitivity regions of chromosome 2 location 60,716,189-60,728,612.

In one embodiment of this aspect and all other aspects described herein, the epigenetic modification changes the DNaseI sensitivity regions of chromosome 2 location 60,716,189-60,728,612.

In one embodiment of this aspect and all other aspects described herein, the epigenetic modification changes the histone modifications on chromosome 2 location 60,716,189-60,728,612.

In one embodiment of this aspect and all other aspects described herein, the insertion of at least one engineered specific-repressor sequence changes the histone modifications on chromosome 2 location 60,716,189-60,728,612.

In one embodiment of this aspect and all other aspects described herein, the epigenetic modifications changes the GATA1/TAL1 binding of the enhancer region on chromosome 2 location 60,716,189-60,728,612 such that the overall function of this region is affected whereby the mRNA and expression of BCL11A is reduced or decreased. For example, the binding of transcription factors to the GATA1/TAL1.

In one embodiment of this aspect and all other aspects described herein, the insertion of at least one engineered specific-repressor sequence occurs within the GATA1/TAL1 as described herein. The insertion can be at the 5' end or 3'end of GATA1 or TAL1. The insertion can be between GATA1 and TAL1. The insertion changes the GATA1/TAL1 binding of the enhancer region on chromosome 2 location 60,716,189-60,728,612 such that the overall function of this region is affected whereby the mRNA and expression of BCL11A is reduced or decreased. For example, the binding of transcription factors to the GATA1/TAL1.

In one embodiment of this aspect and all other aspects described herein, the epigenetic modification changes the interaction between the BCL11A enhancer and the BCL11A promoter. In one embodiment, the interaction is reduced or weakened such that the overall function of this region is affected whereby the mRNA and expression of BCL11A is reduced or decreased.

In one embodiment of this aspect and all other aspects described herein, the epigenetic modifications changes the interaction between the chromosome 2 location 60,716,189-60,728,612 with the BCL11A promoter. In one embodiment, the interaction is reduced or weakened such that the overall function of this region is affected whereby the mRNA and expression of BCL11A is reduced or decreased.

In one embodiment of this aspect and all other aspects described herein, the isolated genetic engineered human cell having at least one epigenetic modification at the genomic DNA of the cell on chromosome 2. In another of this aspect and all other aspects described herein, the isolated genetic engineered human cell having at least one epigenetic modification at the genomic DNA of the cell on chromosome 2 location 60,716,189-60,728,612.

In some aspects of any of these isolated genetic engineered human cells having at least one epigenetic modification, the cells are transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60,716,189-60,728,612 is transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60,716,189-60,728,612 is stored for later use by cryopreservation.

In some aspects of any of those isolated genetic engineered human cells having at least one epigenetic modification, the cells are stored for later use by cryopreservation.

In one embodiment of this aspect and all other aspects described herein, the isolated genetic engineered human cell having at least one genetic modification at the genomic DNA of the cell on chromosome 2 location 60,716,189-60,728,612 is cryopreserved, thawed and transplanted into mammal for use in increasing the fetal hemoglobin in the mammal.

In some aspects of any of those isolated genetic engineered human cells having at least one epigenetic modification, cryopreserved, thawed and transplanted into mammal for use in increasing the fetal hemoglobin in the mammal.

In one embodiment of this aspect, and all other aspects, the agent composition further comprises guideRNA. In one embodiment of this aspect, and all other aspects, the guideRNA comprising a sequence selected from SEQ ID NOs 2-9. GuideRNAs are known in the art. One of skill in the can determine an appropriate guideRNA for use in this disclosed invention.

In one embodiment of this aspect, and all other aspects, the method further comprises selecting a subject who has been diagnosed with a hemoglobinopathy. In one embodiment of this aspect, and all other aspects, the mammal has been diagnosed with a hemoglobinopathy. Non-limiting examples of hemoglobinopathies include β-hemoglobinopathy, sickle cell disease, and β-thalassemia.

In one embodiment of this aspect, and all other aspects, the composition is administered by injection, infusion, instillation, or ingestion.

In one embodiment of this aspect, and all other aspects, the mammal or subject is further administered an epigenetic modifier.

In one embodiment of this aspect, and all other aspects, the mammal or subject or isolated cells are human or derived from a human.

In one embodiment of this aspect, and all other aspects, the isolated progenitor cell or isolated cell is a hematopoietic progenitor cell. In one embodiment of this aspect, and all other aspects, the isolated progenitor cell or isolated cell is a human cell. In one embodiment of this aspect, and all other aspects, the isolated progenitor cell is a CD34+ cell.

In one embodiment of this aspect, and all other aspects, the composition further comprises a pharmaceutically acceptable carrier or diluent, and/or an epigenetic modifier.

In one embodiment of this aspect, and all other aspects, the CD 34+ hematopoietic progenitor cell is expanded ex vivo.

In one embodiment of this aspect, and all other aspects, the CD 34+ hematopoietic progenitor cell is formulated for injection or infusion.

In one embodiment of this aspect, and all other aspects, the fusion protein comprises at least two DNA-targeting endonucleases comprising a first Cas9 or Cas12a nuclease, wherein said nuclease comprises a protospacer adjacent motif recognition domain and a peptide linker, and wherein said peptide linker is attached to a second Cas9 or Cas12a nuclease.

In one embodiment of this aspect, and all other aspects, the Cas9 nuclease of the fusion protein is SpCas9, SaCas9, NmCas9, CjCas9 and AnCas9. In one embodiment of this aspect, and all other aspects, the Cas12a nuclease of the fusion protein is FnCas12a, LbCas12a and AsCas12a. Cas proteins exemplified herein are merely examples, and are not to be construed as limiting. A vast number of Cas proteins derived from various species are known in the art, and one skilled in the art would be able to select and utilize at least one Cas protein in the present invention.

In one embodiment of this aspect, and all other aspects, the protospacer adjacent motif recognition domain of fusion protein is SpCas9, SpCas9$^{MT1}$, SpCas9$^{MT2}$, SpCas9$^{MT3}$, NmCas9$^{SM}$ and NmCas9$^{DM}$.

In one embodiment of this aspect, and all other aspects, the protospacer adjacent motif recognition domain of fusion protein is mutated or non-mutated. In one embodiment of this aspect, and all other aspects, the mutated protospacer adjacent motif recognition domain of the fusion protein comprises mutated DNA phosphodiester recognition amino acid residues.

In one embodiment of this aspect, and all other aspects, the peptide linker of fusion protein is a peptide linker between twenty-five and eighty amino acids. In one embodiment, the peptide linker is less than twenty-five, or more than 80 amino acids.

In one embodiment of this aspect, and all other aspects, the fusion protein further comprises a guide RNA which is attached to a guide sequence element. In one embodiment of this aspect, and all other aspects, the guide RNA of said fusion protein is an sgRNA sequence, a crRNA sequence, or a tracrRNA sequence. In one embodiment of this aspect, and all other aspects, the guide sequence element of said guide RNA of said fusion protein is truncated. In one embodiment of this aspect, and all other aspects, the truncated guide sequence element is less than twenty nucleotides.

It is known that there are HbF-associated variations at BCL11A. Six GWAS of HbF level (or the highly correlated trait F-cell number) have been conducted in individuals of European, African and Asian descent, each identifying trait-associated variants within BCL11A (7-12). The same variants are associated with the clinical severity of SCD and β-thalassemia (9, 10, 50), consistent with HbF as a major modifier of these disorders. Variation at BCL11A is estimated to explain ~15% of the trait variance in HbF level (7, 12, 43). Four different SNPs have been identified as most highly associated with the trait (rs1427407 (7), rs11886868 (8), rs4671393 (9) and rs766432 (10-12)); these sentinel SNPs cluster within 3 kb of each other in BCL11A intron-2 (data not show). Haplotypes including the sentinel SNPs appear to better explain the HbF association than any individual SNP (12, 43). Fifty SNPs at the BCL11A locus and twenty-seven SNPs within intron-2 have been associated with HbF level with genome-wide significance (P<5× 10-8). Despite large-scale resequencing efforts, coding variants of BCL11A have not been described (43).

Previously, work has used the CSSCD to fine-map the association signal with HbF at the BCL11A locus and reported a strong association with rs4671393 (43). In that study, rs1427407 was imputed. Two additional SNPs, rs766432 and rs11886868 have also been identified in prior studies as sentinel SNPs most highly trait-associated (8, 10, 11, 51). In a subset of individuals (n=728) for which genotypes at all four sentinel SNPs were available, the association result was not significant at rs4671393, rs766432 or rs11886868 following conditioning on genotypes at rs1427407; conversely, the association remained highly significant for rs1427407 upon conditioning on rs4671393, rs766432 or rs11886868 (Table 4). Therefore, rs1427407 is the SNP most strongly associated with HbF level within the erythroid DHSs and better accounts for the trait association than other previously described sentinel SNPs.

Conditional analysis demonstrated associations that remained significant after conditioning on rs1427407. The most significant residual association was for rs7606173 in DHS+55 (P=9.66×10-11); rs7599488 in DHS+62, which we had previously reported (43), was only slightly less significant (P=2.43×10-10) (Table 1). Analysis of rare DNA sequence variants within the three DHSs did not yield additional independent HbF-associated signals (Table 5).

It was previously found that allele-specific transcription factor (TF) binding are involved with BCL11A expression. Allele-specific biochemical studies were performed using informative heterozygotes to control for trans-acting differences between samples and to ensure equal abundance of both alleles, substantiated by equal representation of alleles in paired gDNA. rs1427407 is found directly at the center of a GATA1 and TAL1 binding peak at DHS+62. In the ChIP assays performed, chromatin was sonicated to approximately 500-bp fragments. The five primary human erythroid precursor samples heterozygous for rs1427407 used for ChIP-qPCR were Sanger sequenced at the erythroid DHSs. The only other heterozygous SNP within 500-bp of rs1427407 in any of these samples was rs7599488 (304-bp 3' of rs1427407) which was heterozygous in just two of the five samples. This SNP does not fall within GATA1 or TAL1 binding motifs. It therefore appears unlikely that another SNP within DHS+62 could account for the observed allele-specific TF binding.

In addition, the inventors have found that there is an association between BCL11A expression and HbF level. The inventors' studies provide an estimate of the change in BCL11A expression that may result in a clinically meaningful increase in HbF level. Among a limited set of human lymphoblastoid cell lines were previously reported correlation of the high HbF-associated A-allele of rs4671393 with reduced BCL11A expression (13). Extension of these experiments to a larger collection of genotyped lines failed to confirm this observation. Hence, it was found that the HbF-associated rs1427407-rs7606173 haplotype influence BCL11A expression in an erythroid-specific context, a possibility consistent with the DNase I sensitivity findings. BCL11A mRNA expression in primary erythroid precursors differed by 1.7-fold between the high-HbF rs1427407-rs7606173 T-G and low-HbF G-C haplotypes (data not show); correspondingly, median HbF levels were 10.6% and 3.1% in T-G and G-C homozygotes, respectively. Of note, the results demonstrating allele-specific expression of BCL11A in primary human erythroid cells were observed in cells heterozygous for the rs1427407-rs7606173 haplotype, and thus the modest effects on BCL11A expression reflect the combined effects of all functional SNPs within the haplotype. While inheritance of a protective BCL11A haplotype is clinically beneficial on a population basis (9, 10, 50), the average level of HbF in T-G homozygotes remains below that required to prevent morbidity from SCD. The sensitivity of HbF level to BCL11A expression, however, predicts that relief of disease severity might require only a modest further reduction in BCL11A expression.

It was further investigated the developmental regulation of globin genes and BCL11A. During human development, yolk sac-derived s-globin is superseded in the first trimester by fetal liver-derived γ-globin. Following birth, as erythropoiesis shifts from the liver to the bone marrow, γ-globin is gradually silenced and β-globin predominates. Only a single switch in globin gene expression occurs in mouse ontogeny. During this transition, which occurs at mid-gestation, the circulating yolk sac-derived primitive erythrocytes express embryonic-stage globins sy and PH1, whereas the fetal liver definitive erythroblasts express adult-stage globins β1 and β2. Concordant with this developmental switch, BCL11A is expressed in the definitive but not primitive-stage erythroid lineage and required for the change in globin gene expression (16, 52).

In the stable transgenic BCL11A+52.0-64.4 reporter lines at 10.5 dpc, lacZ expression was observed only in the fetal liver primordium and not in the circulating blood within the embryo, placenta or yolk sac (data not shown). These results, coupled with the finding of lacZ expression in the 12.5 dpc definitive fetal liver erythroblasts but not yolk sac-derived primitive circulating erythrocytes (data not shown), demonstrate that the BCL11A composite enhancer sequences drive expression in a developmentally-specific pattern concordant with endogenous globin gene switching.

A series of deletion mutants were generated to refine the minimal elements required for erythroid enhancer activity. Sequences containing the central +58 DHS were sufficient for erythroid enhancer activity. Those sequences containing only the flanking +62 or +55 elements were unable to direct erythroid gene expression. To test the ability of the DHSs to enhance gene expression in primary human erythroid precursors, lentiviral delivery of a GFP reporter system was used as previously described (39). Similarly, the +58 DHS enhanced gene expression in this reporter assay.

It was decided to generate cell lines with a Bcl11a enhancer deletion to investigate the requirement of the enhancer for BCL11A expression. Stable erythroid cells with disruption of the enhancer were generated. Since there are no suitable adult-stage human erythroid cell lines, and as proof of principle, the inventors turned to the murine system. Mouse erythroleukemia (MEL) cells depend on BCL11A for an adult-stage pattern of globin gene expression (14). An orthologous erythroid composite enhancer at mouse Bcl11a intron-2 was identified. Like the human GWAS-marked intron-2 BCL11A enhancer, these sequences possessed a series of erythroid-specific DHSs. In addition, these sequences were decorated by H3K4me1 and H3K27ac, lacked H3K4me3 and H3K27me3, and occupied by both GATA1 and TAL1 in mouse erythroid chromatin. Composite regulatory elements including a series of adjacent DHSs have been shown to be critical for gene expression at numerous loci, including among others the β-globin locus control region, α-globin multispecies conserved sequences, and IgH regulatory region (53-55). Species-specific unique features of the composite enhancer was observed. For example, the conserved mouse sequences to each of the three human DHSs +62, +58 and +55 was identified, and found erythroid DNase I hypersensitivity at the +62 and +55 conserved sequences, however the +58 conserved sequences lacked DNase I hypersensitivity.

PCR and Southern blotting verified excision of the +50.4-60.4 kb intronic segment of Bcl11a in three unique MEL clones and two unique pre-B lymphocyte clones. Sanger-sequenced breakpoints were characteristic of TALEN-mediated cleavage with subsequent NHEJ repair. Upon deletion of the intronic segment, dramatic reduction in BCL11A transcript was observed in the MEL cell clones by RT-qPCR, using primer pairs detecting exon junctions upstream, spanning or downstream of the deletion.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

By "interferes with BCL11A interactions with BCL11A binding partners" is meant that the amount of interaction of BCL11A with the BCL11A binding partner is at least 5% lower in populations treated with a BCL11A inhibitor, than a comparable, control population, wherein no BCL11A inhibitor is present. It is preferred that the amount of interaction of BCL11A with the BCL11A binding partner in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added. At a minimum, BCL11A interaction can be assayed by determining the amount of BCL11A binding to the BCL11A binding partner using techniques standard in the art, including, but not limited to, mass spectrometry, immunoprecipitation, or gel filtration assays. Alternatively, or in addition, BCL11A activity can be assayed by measuring fetal hemoglobin expression at the mRNA or protein level following treatment with a candidate BCL11A inhibitor.

In one embodiment, BCL11A activity is the interaction of BCL11A with its binding partners: GATA-1, FOG-1, components of the NuRD complex, matrin-3, MTA2 and RBBP7. Accordingly, any antibody or fragment thereof, small molecule, chemical or compound that can block this interaction is considered an inhibitor of BCL11A activity.

As used herein, the term "genetic engineered cell" refers to a cell that comprises at least one genetic modification, as that term is used herein.

As used herein, the term "genetic modification" refers to a disruption at the genomic level resulting in a decrease in BCL11A expression or activity in a cell. Exemplary genetic modifications can include deletions, frame shift mutations, point mutations, exon removal, removal of one or more DNAse 1-hypersensitive sites (DHS) (e.g., 2, 3, 4 or more DHS regions), etc.

By "decreased BCL11A expression" is meant that the amount of expression of BCL11A is at least 5% lower in a cell or cell population treated with a DNA-targeting endonuclease, than a comparable, control cell or cell population, wherein no agent that deletes the GATA1 binding element is present. It is preferred that the percentage of BCL11A expression in a treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no agent that deletes the GATA1 binding element is added.

By "decreases BCL11A activity" is meant that the amount of functional activity of BCL11A is at least 5% lower in a cell or cell population treated with the methods described herein, than a comparable, control cell or population, wherein no agent that deletes the GATA1 binding element is present. It is preferred that the percentage of BCL11A activity in a treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no agent that deletes the GATA1 binding element is added. At a minimum, BCL11A activity can be assayed by determining the amount of BCL11A expression at the protein or mRNA levels, using techniques standard in the art. Alternatively, or in addition, BCL11A activity can be determined using a reporter construct, wherein the reporter construct is sensitive to BCL11A activity. The γ-globin locus sequence is recognizable by the nucleic acid-binding motif of the BCL11A construct.

In one embodiment, as used herein, the term "DNA targeting endonuclease" refers to an endonuclease that generates a double-stranded break at a desired position in the genome (e.g., chromosome 2 location 60,716,189-60,728,612) without producing undesired off-target double-stranded breaks. The DNA targeting endonuclease can be a naturally occurring endonuclease (e.g., a bacterial meganuclease) or it can be artificially generated (e.g., engineered meganucleases, TALENs, or ZFNs, among others).

In another embodiment, as used herein, the term "DNA targeting endonuclease" refers to an endonuclease that generates a single-stranded break or a "nick" or break on one strand of the DNA phosphate sugar backbone at a desired position in the genome (e.g., chromosome 2 location 60,716, 189-60,728,612) without producing undesired off-target DNA stranded breaks.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the methods and compositions described herein can include such other forms of expression vectors, such as viral vectors (e.g., replication defective retroviruses, lentiviruses, adenoviruses and adeno-associated viruses), which serve equivalent functions.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the DNA-targeting endonuclease can be delivered by way of a vector comprising a regulatory sequence to direct synthesis of the DNA-targeting endonuclease at specific intervals, or over a specific time period. It will be appreciated by those skilled in the art that the design of the expression vector can depend on such factors as the choice of the target cell, the level of expression desired, and the like.

As used herein the term "cleaves" generally refers to the generation of a double-stranded break in the DNA genome at a desired location.

As used herein, the term "effective amount of a composition comprising at least two DNA-targeting endonuclease" refers to an amount of at least two DNA-targeting endonuclease that yields sufficient endonuclease activity to generate at least two double-stranded breaks in the desired location of the genome with the goal of creating a deletion between these breaks. In one embodiment, the effective amount of at least two DNA-targeting endonuclease generates at least two double-stranded break at the desired genetic locus in at least 20% of the cells in a population contacted with the composition (e.g., at least 30%, at least 40%, at least 50%, at least 60%, at least 70%, at least 80%, at least 90%, at least 95%, at least 99%, or even 100% of the cells in the population comprise a genetic modification produced by the DNA-targeting endonuclease composition).

As used herein the term "increasing the fetal hemoglobin levels" in a cell indicates that fetal hemoglobin is at least 5% higher in populations treated with an agent that disrupts BCL11A mRNA or protein expression (e.g., comprising at least two DNA-targeting endonuclease) by binding to genomic DNA at chromosome 2 location 60,716,189-60, 728,612, than in a comparable, control population, wherein no agent is present. It is preferred that the percentage of fetal hemoglobin expression in a population treated with such an agent that binds the genomic DNA at chromosome 2 location 60,716,189-60,728,612 is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the agent that binds genomic DNA at chromosome 2 location 60,716,189-60,728,612. In one embodiment, any method known in the art can be used to measure an increase in fetal hemoglobin expression, e. g. Western Blot analysis of fetal γ-globin protein and quantifying mRNA of fetal γ-globin.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of hematopoietic progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not hematopoietic progenitor cells as defined by the terms herein.

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of hematopoietic progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a hemoglobinopathy. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

In connection with contacting a cell with at least two DNA-targeting endonucleases to decrease BCL11A expression, the phrase "increasing fetal hemoglobin levels in a cell" indicates that fetal hemoglobin in a cell or population of cells is at least 5% higher in the cell or population of cells treated with the DNA-targeting endonuclease, than a comparable, control population, wherein no DNA-targeting endonuclease is present. It is preferred that the fetal hemoglobin expression in a DNA-targeting endonuclease treated cell is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated population. The term "control treated population" is used herein to describe a population of cells that has been treated with identical media, viral induction, nucleic acid sequences, temperature, confluency, flask size, pH, etc., with the exception of the addition of the BCL11A inhibitor.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

Accordingly, in one embodiment, the mammal has been diagnosed with a hemoglobinopathy. In a further embodiment, the hemoglobinopathy is a β-hemoglobinopathy. In one preferred embodiment, the hemoglobinopathy is a sickle cell disease. As used herein, "sickle cell disease" can be sickle cell anemia, sickle-hemoglobin C disease (HbSC), sickle beta-plus-thalassaemia (HbS/β+), or sickle beta-zero-thalassaemia (HbS/β0). In another preferred embodiment, the hemoglobinopathy is a β-thalassemia.

As used herein, the term "hemoglobinopathy" means any defect in the structure or function of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like.

In one embodiment, the term "effective amount", as used herein, refers to the amount of a cell composition that is safe and sufficient to treat, lessen the likelihood of, or delay the development of a hemoglobinopathy. The amount can thus cure or result in amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Hemoglobinopathies

Fetal hemoglobin (HbF) is a tetramer of two adult α-globin polypeptides and two fetal β-like γ-globin polypeptides. During gestation, the duplicated γ-globin genes constitute the predominant genes transcribed from the β-globin locus. Following birth, γ-globin becomes progressively replaced by adult β-globin, a process referred to as the "fetal switch" (3). The molecular mechanisms underlying this switch have remained largely undefined and have been a subject of intense research. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth at which point HbA becomes predominant. This switch results primarily from decreased transcription of the gamma-globin genes and increased transcription of beta-globin genes. On average, the blood of a normal adult contains only about 2% HbF, though residual HbF levels have a variance of over 20 fold in healthy adults (Atweh, Semin. Hematol. 38(4):367-73 (2001)).

Hemoglobinopathies encompass a number of anemias of genetic origin in which there is a decreased production and/or increased destruction (hemolysis) of red blood cells (RBCs). These disorders also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders specifically associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickled) hemoglobin (HbS). HbS RBCs are more fragile than normal RBCs and undergo hemolysis more readily, leading eventually to anemia (Atweh, Semin. Hematol. 38(4):367-73 (2001)). Moreover, the presence of a BCL11A genetic variant, HBS1L-MYB variation, ameliorates the clinical severity in beta-thalassemia. This variant has been shown to be associated with HbF levels. It has been shown that there is an odds ratio of 5 for having a less severe form of beta-thalassemia with the high-HbF variant (Galanello S. et al., 2009, Blood, in press).

The search for treatment aimed at reduction of globin chain imbalance in patients with β-hemoglobinopathies has focused on the pharmacologic manipulation of fetal hemoglobin ($\alpha 2\gamma 2$; HbF). The important therapeutic potential of such approaches is suggested by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease (Pembrey, et al., Br. J. Haematol. 40: 415-429 (1978)). It is now accepted that β-hemoglobinopathies, such as sickle cell anemia and the β-thalassemias, are ameliorated by increased HbF production. (Reviewed in Jane and Cunningham Br. J. Haematol. 102: 415-422 (1998) and Bunn, N. Engl. J. Med. 328: 129-131 (1993)).

While the molecular mechanisms controlling the in vivo developmental switch from γ- to β-globin gene expression are currently unknown, there is accumulating evidence that external factors can influence γ-globin gene expression. The first group of compounds discovered having HbF reactivation activity were cytotoxic drugs. The ability to cause de novo synthesis of HbF by pharmacological manipulation was first shown using 5-azacytidine in experimental animals (DeSimone, Proc Natl Acad Sci USA. 79(14):4428-31 (1982)). Subsequent studies confirmed the ability of 5-azacytidine to increase HbF in patients with β-thalassemia and sickle cell disease (Ley, et al., N. Engl. J. Medicine, 307: 1469-1475 (1982), and Ley, et al., Blood 62: 370-380 (1983)). Additional experiments demonstrated that baboons treated with cytotoxic doses of arabinosylcytosine (ara-C) responded with striking elevations of F-reticulocytes (Papayannopoulou et al., Science. 224(4649):617-9 (1984)), and that treatment with hydroxyurea led to induction of γ-globin in monkeys or baboons (Letvin et. al., N Engl J Med. 310(14):869-73 (1984)).

The second group of compounds investigated for the ability to cause HbF reactivation activity was short chain fatty acids. The initial observation in fetal cord blood progenitor cells led to the discovery that γ-aminobutyric acid can act as a fetal hemoglobin inducer (Perrine et al., Biochem Biophys Res Commun. 148(2):694-700 (1987)). Subsequent studies showed that butyrate stimulated globin production in adult baboons (Constantoulakis et al., Blood. December; 72(6):1961-7 (1988)), and it induced γ-globin in erythroid progenitors in adult animals or patients with sickle cell anemia (Perrine et al., Blood. 74(1):454-9 (1989)). Derivatives of short chain fatty acids such as phenylbutyrate (Dover et al., Br J Haematol. 88(3):555-61 (1994)) and valproic acid (Liakopoulou et al., 1: Blood. 186(8):3227-35 (1995)) also have been shown to induce HbF in vivo. Given the large number of short chain fatty acid analogs or derivatives of this family, there are a number of potential compounds of this family more potent than butyrate. Phenylacetic and phenylalkyl acids (Torkelson et al., Blood Cells Mol Dis. 22(2):150-8. (1996)), which were discovered during subsequent studies, were considered potential HbF inducers as they belonged to this family of compounds. Presently, however, the use of butyrate or its analogs in sickle cell anemia and β-thalassemia remains experimental and cannot be recommended for treatment outside of clinical trials.

Clinical trials aimed at reactivation of fetal hemoglobin synthesis in sickle cell anemia and β-thalassemia have included short term and long term administration of such compounds as 5-azacytidine, hydroxyurea, recombinant human erythropoietin, and butyric acid analogs, as well as combinations of these agents. Following these studies, hydroxyurea was used for induction of HbF in humans and later became the first and only drug approved by the Food and Drug Administration (FDA) for the treatment of hemoglobinopathies. However, varying drawbacks have contraindicated the long term use of such agents or therapies, including unwanted side effects and variability in patient responses. For example, while hydroxyurea stimulates HbF production and has been shown to clinically reduce sickling crisis, it is potentially limited by myelotoxicity and the risk of carcinogenesis. Potential long term carcinogenicity would also exist in 5-azacytidine-based therapies. Erythropoietin-based therapies have not proved consistent among a range of patient populations. The short half-lives of butyric acid in vivo have been viewed as a potential obstacle in adapting these compounds for use in therapeutic interventions. Furthermore, very high dosages of butyric acid are necessary for inducing γ-globin gene expression, requiring catheritization for continuous infusion of the compound. Moreover, these high dosages of butyric acid can be associated with neurotoxicity and multiorgan damage (Blau, et al., Blood 81: 529-537 (1993)). While even minimal increases in HbF levels are helpful in sickle cell disease, β-thalassemias require a much higher increase that is not reliably, or safely, achieved by any of the currently used agents (Olivieri, Seminars in Hematology 33: 24-42 (1996)).

Identifying natural regulators of HbF induction and production could provide a means to devise therapeutic interventions that overcome the various drawbacks of the compounds described above. Recent genome-wide association studies have yielded insights into the genetic basis of numerous complex diseases and traits (McCarthy et al., Nat Rev Genet 9, 356 (2008) and Manolio et. al. J Clin Invest 118, 1590 (2008)). However, in the vast majority of instances, the functional link between a genetic association and the underlying pathophysiology remains to be uncovered. The level of fetal hemoglobin (HbF) is inherited as a quantitative trait and clinically important, given its above-mentioned and well-characterized role in ameliorating the severity of the principal β-hemoglobinopathies, sickle cell disease and β-thalassemia (Nathan et. al., Nathan and Oski's hematology of infancy and childhood ed. 6th, pp. 2 v. (xiv, 1864, xli p.) 2003)). Two genome-wide association studies have identified three major loci containing a set of five common single nucleotide polymorphisms (SNPs) that account for ~20% of the variation in HbF levels (Lettre et al., Proc Natl Acad Sci USA (2008); Uda et al., Proc Natl Acad Sci USA 105, 1620 (2008); Menzel et al., Nat Genet 39, 1197 (2007)). Moreover, several of these variants appear to predict the clinical severity of sickle cell disease (Lettre et al., Proc Natl Acad Sci USA (2008)) and at least one of these SNPs may also affect clinical outcome in β-thalassemia (Uda et al., Proc Natl Acad Sci USA 105, 1620 (2008)). The SNP with the largest effect size, explaining over 10% of the variation in HbF, is located in the second intron of a gene on chromosome 2, BCL11A. Whereas BCL11A, a C2H2-type zinc finger transcription factor, has been investigated for its role in lymphocyte development (Liu et al., Nat Immunol 4, 525 (2003) and Liu et al., Mol Cancer 5, 18 (2006)), its role in red blood cell production or globin gene regulation has not been previously assessed.

At the onset of the recombinant DNA era, studies of globin gene structure provided a strong molecular foundation for interrogating the fetal globin switch. Considerable effort has focused on delineating the cis-elements within the β-globin locus necessary for proper regulation of the genes within the β-like globin cluster. These studies relied on naturally occurring mutations and deletions that dramatically influence HbF levels in adults, and have been complemented by generation of transgenic mice harboring portions of the cluster (Nathan et. al., Nathan and Oski's hematology of infancy and childhood ed. 6th, pp. 2 v. (xiv, 1864, xli p.) 2003) and G. Stamatoyannopoulos, Exp Hematol 33, 259 (2005)). Although the precise cis-elements required for globin switching remain ill-defined, findings in transgenic mice have strongly indicated that the γ-globin genes are autonomously silenced in the adult stage, a finding that is most compatible with the absence of fetal-stage specific activators or the presence of a stage-specific repressor. The results of recent genetic association studies provide candidate genes to interrogate for their involvement in control of the γ-globin genes, such as BCL11A.

Hematopoietic Progenitor Cells

In one embodiment, the hematopoietic progenitor cell is contacted ex vivo or in vitro. In a specific embodiment, the cell being contacted is a cell of the erythroid lineage. In one embodiment, the cell composition comprises cells having decreased BCL11A expression.

"Hematopoietic progenitor cell" as the term is used herein, refers to cells of a stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoeisis such that upon final differentiation it forms an erythrocyte or red blood cell (RBC). Such cells belong to one of three lineages, erythroid, lymphoid, and myeloid, originating from bone marrow haematopoietic progenitor cells. Upon exposure to specific growth factors and other components of the haematopoietic microenvironment, haematopoietic progenitor cells can mature through a series of intermediate differentiation cellular types, all intermediates of the erythroid lineage, into RBCs. Thus, cells of the "erythroid lineage", as the term is used herein, comprise hematopoietic progenitor cells, rubriblasts, prorubricytes, erythroblasts, metarubricytes, reticulocytes, and erythrocytes.

In some embodiment, the hematopoietic progenitor cell has at least one of the cell surface marker characteristic of hematopoietic progenitor cells: CD34+, CD59+, Thy1/CD90+, CD38lo/-, and C-kit/CD117+. Preferably, the hematopoietic progenitor cells have several of these markers.

In some embodiments, the hematopoietic progenitor cells of the erythroid lineage have the cell surface marker characteristic of the erythroid lineage: CD71 and Ter119.

Stem cells, such as hematopoietic progenitor cells, are capable of proliferation and giving rise to more progenitor cells having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a hematopoietic progenitor cell), which in turn can differentiate into other types of precursor cells further down the pathway (such as an erthyrocyte precursor), and then to an end-stage differentiated cell, such as an erthyrocyte, which plays a characteristic role in a certain tissue type, and may or may not retain the capacity to proliferate further.

Induced Pluripotent Stem Cells

In some embodiments, the genetic engineered human cells described herein are derived from isolated pluripotent stem cells. An advantage of using iPSCs is that the cells can be derived from the same subject to which the progenitor cells are to be administered. That is, a somatic cell can be obtained from a subject, reprogrammed to an induced pluripotent stem cell, and then re-differentiated into a hematopoietic progenitor cell to be administered to the subject (e.g., autologous cells). Since the progenitors are essentially derived from an autologous source, the risk of engraftment rejection or allergic responses is reduced compared to the use of cells from another subject or group of subjects. In some embodiments, the hematopoeitic progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc (Takahashi and Yamanaka, 2006). iPSCs resemble ES cells as they restore the pluripotency-associated transcriptional circuitry and muc of the epigenetic landscape. In addition, mouse iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) *Cell-Stem Cell* 2:525-528, Huangfu, D., et al (2008) *Nature Biotechnology* 26(7):795-797, and Marson, A., et al (2008) *Cell-Stem Cell* 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of hematopoietic progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Genome Editing and DNA-Targeting Endonucleases

As used herein, the term "genome editing" refers to a reverse genetics method using artificially engineered nucleases to cut and create specific double-stranded breaks at a desired location(s) in the genome, which are then repaired by cellular endogenous processes such as, homologous recombination (HR), homology directed repair (HDR) and non-homologous end-joining (NHEJ). NHEJ directly joins the DNA ends in a double-stranded break, while HDR utilizes a homologous sequence as a template for regenerating the missing DNA sequence at the break point.

Described herein are methods that utilize a composition comprising a fusion protein comprising at least two DNA-targeting endonucleases, or a composition comprising a vector carrying the coding sequence of a fusion protein comprising at least two DNA-targeting endonucleases. For example, a fusion protein having at least Cas9 proteins, or a Cas9 and a Cas12a protein.

Genome editing cannot be performed using traditional restriction endonucleases since most restriction enzymes recognize a few base pairs on the DNA as their target and the probability is very high that the recognized base pair combination will be found in many locations across the genome resulting in multiple cuts (i.e., not limited to a desired location). To overcome this challenge and create site-specific double-stranded breaks, several distinct classes of nucleases have been discovered and bioengineered to date. These are the meganucleases, Zinc finger nucleases (ZFNs), Cas9/CRISPR system, and transcription-activator like effector nucleases (TALENs).

Meganucleases are commonly grouped into four families: the LAGLIDADG family ("LAGLIDADG" disclosed as SEQ ID NO: 200), the GIY-YIG family, the His-Cys box family and the HNH family. These families are characterized by structural motifs, which affect catalytic activity and recognition sequence. For instance, members of the LAGLIDADG family ("LAGLIDADG" disclosed as SEQ ID NO: 200) are characterized by having either one or two copies of the conserved LAGLIDADG motif (SEQ ID NO: 200) (see Chevalier et al. (2001), Nucleic Acids Res. 29(18): 3757-3774). The LAGLIDADG meganucleases ("LAGLIDADG" disclosed as SEQ ID NO: 200) with a single copy of the LAGLIDADG motif (SEQ ID NO: 200) form homodimers, whereas members with two copies of the LAGLIDADG (SEQ ID NO: 200) are found as monomers. Similarly, the GIY-YIG family members have a GIY-YIG module, which is 70-100 residues long and includes four or five conserved sequence motifs with four invariant residues, two of which are required for activity (see Van Roey et al. (2002), Nature Struct. Biol. 9: 806-811). The His-Cys box meganucleases are characterized by a highly conserved series of histidines and cysteines over a region encompassing several hundred amino acid residues (see Chevalier et al. (2001), Nucleic Acids Res. 29(18): 3757-3774). In the case of the NHN family, the members are defined by motifs containing two pairs of conserved histidines surrounded by asparagine residues (see Chevalier et al. (2001), Nucleic Acids Res. 29(18): 3757-3774). The four families of meganucleases are widely separated from one another with respect to conserved structural elements and, consequently, DNA recognition sequence specificity and catalytic activity.

Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. *Nature Methods* (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision BioSciences' Directed Nuclease Editor™ genome editing technology.

ZFNs and TALENs restriction endonuclease technology utilizes a non-specific DNA cutting enzyme which is linked to a specific DNA sequence recognizing peptide(s) such as zinc fingers and transcription activator-like effectors (TALEs). Typically an endonuclease whose DNA recognition site and cleaving site are separate from each other is selected and the its cleaving portion is separated and then linked to a sequence recognizing peptide, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs for use with the methods and compositions described herein can be obtained commercially from e.g., Sangamo Biosciences™ (Richmond, CA).

It is contemplated herein that the Cas9/CRISPR system of genome editing be employed with the methods and compositions described herein. Clustered regularly interspaced short palindromic repeats (CRISPR)/CRISPR-associated (Cas) systems is useful for RNA-programmable genome editing (see e.g., Jinek, M. et al. *Science* (2012) 337(6096): 816-821).

Alternatively, genome editing can be performed using recombinant adeno-associated virus (rAAV) based genome engineering, which is a genome-editing platform centered around the use of rAAV vectors that enables insertion, deletion or substitution of DNA sequences into the genomes of live mammalian cells. The rAAV genome is a single-stranded deoxyribonucleic acid (ssDNA) molecule, either positive- or negative-sensed, which is about 4.7 kilobase long. These single-stranded DNA viral vectors have high transduction rates and have a unique property of stimulating endogenous homologous recombination in the absence of causing double strand DNA breaks in the genome. One of skill in the art can design a rAAV vector to target a desired genomic locus and perform both gross and/or subtle endogenous gene alterations in a cell, such as a deletion. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Pharmaceutically Acceptable Carriers

The methods of administering human hematopoietic progenitors to a subject as described herein involve the use of therapeutic compositions comprising hematopoietic progenitor cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired.

In general, the hematopoietic progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the hematopoietic progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Administration & Efficacy

As used herein, the terms "administering," "introducing" and "transplanting" are used interchangeably in the context of the placement of cells, e.g. hematopoietic progenitor cells, as described herein into a subject, by a method or route which results in at least partial localization of the introduced cells at a desired site, such as a site of injury or repair, such that a desired effect(s) is produced. The cells e.g. hematopoietic progenitor cells, or their differentiated progeny can be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of hematopoietic progenitor cells is administered via a systemic route of administration, such as an intraperitoneal or intravenous route.

When provided prophylactically, hematopoietic progenitor cells described herein can be administered to a subject in advance of any symptom of a hemoglobinopathy, e.g., prior to the switch from fetal γ-globin to predominantly β-globin. Accordingly, the prophylactic administration of a hematopoietic progenitor cell population serves to prevent a hemoglobinopathy, as disclosed herein.

When provided therapeutically, hematopoietic progenitor cells are provided at (or after) the onset of a symptom or indication of a hemoglobinopathy, e.g., upon the onset of sickle cell disease.

In some embodiments of the aspects described herein, the hematopoietic progenitor cell population being administered according to the methods described herein comprises allogeneic hematopoietic progenitor cells obtained from one or more donors. As used herein, "allogeneic" refers to a hematopoietic progenitor cell or biological samples comprising hematopoietic progenitor cells obtained from one or more different donors of the same species, where the genes at one or more loci are not identical. For example, a hematopoietic progenitor cell population being administered to a subject can be derived from umbilical cord blood obtained from one more unrelated donor subjects, or from one or more non-identical siblings. In some embodiments, syngeneic hematopoietic progenitor cell populations can be used, such as those obtained from genetically identical animals, or from identical twins. In other embodiments of this aspect, the hematopoietic progenitor cells are autologous cells; that is, the hematopoietic progenitor cells are obtained or isolated from a subject and administered to the same subject, i.e., the donor and recipient are the same.

For use in the various aspects described herein, an effective amount of hematopoietic progenitor cells, comprises at least $10^2$ hematopoietic progenitor cells, at least $5 \times 10^2$ hematopoietic progenitor cells, at least $10^3$ hematopoietic progenitor cells, at least $5 \times 10^3$ hematopoietic progenitor cells, at least $10^4$ hematopoietic progenitor cells, at least $5 \times 10^4$ hematopoietic progenitor cells, at least $10^5$ hematopoietic progenitor cells, at least $2 \times 10^5$ hematopoietic progenitor cells, at least $3 \times 10^5$ hematopoietic progenitor cells, at least $4 \times 10^5$ hematopoietic progenitor cells, at least $5 \times 10^5$ hematopoietic progenitor cells, at least $6 \times 10^5$ hematopoietic progenitor cells, at least $7 \times 10^5$ hematopoietic progenitor cells, at least $8 \times 10^5$ hematopoietic progenitor cells, at least $9 \times 10^5$ hematopoietic progenitor cells, at least $1 \times 10^6$ hematopoietic progenitor cells, at least $2 \times 10^6$ hematopoietic progenitor cells, at least $3 \times 10^6$ hematopoietic progenitor cells, at least $4 \times 10^6$ hematopoietic progenitor cells, at least $5 \times 10^6$ hematopoietic progenitor cells, at least $6 \times 10^6$ hematopoietic progenitor cells, at least $7 \times 10^6$ hematopoietic progenitor cells, at least $8 \times 10^6$ hematopoietic progenitor cells, at least $9 \times 10^6$ hematopoietic progenitor cells, or multiples thereof. The hematopoietic progenitor cells can be derived from one or more donors, or can be obtained from an autologous source. In some embodiments of the aspects described herein, the hematopoietic progenitor cells are expanded in culture prior to administration to a subject in need thereof.

In one embodiment, the term "effective amount" as used herein refers to the amount of a population of human hematopoietic progenitor cells or their progeny needed to alleviate at least one or more symptom of a hemoglobinopathy, and relates to a sufficient amount of a composition to provide the desired effect, e.g., treat a subject having a hemoglobinopathy. The term "therapeutically effective amount" therefore refers to an amount of hematopoietic progenitor cells or a composition comprising hematopoietic progenitor cells that is sufficient to promote a particular effect when administered to a typical subject, such as one who has or is at risk for a hemoglobinopathy. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

As used herein, "administered" refers to the delivery of a hematopoietic stem cell composition as described herein into a subject by a method or route which results in at least partial localization of the cell composition at a desired site. A cell composition can be administered by any appropriate route which results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. For the delivery of cells, administration by injection or infusion is generally preferred.

In one embodiment, the cells as described herein are administered systemically. The phrases "systemic administration," "administered systemically", "peripheral administration" and "administered peripherally" as used herein refer to the administration of a population of hematopoietic progenitor cells other than directly into a target site, tissue, or organ, such that it enters, instead, the subject's circulatory system and, thus, is subject to metabolism and other like processes.

The efficacy of a treatment comprising a composition as described herein for the treatment of a hemoglobinopathy can be determined by the skilled clinician. However, a treatment is considered "effective treatment," as the term is used herein, if any one or all of the signs or symptoms of, as but one example, levels of fetal β-globin are altered in a beneficial manner, other clinically accepted symptoms or markers of disease are improved or ameliorated, e.g., by at least 10% following treatment with an inhibitor. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of sepsis; or (2) relieving the disease, e.g., causing regression of symptoms; and (3) preventing or reducing the likelihood of the development of infection or sepsis.

The treatment according to the present invention ameliorates one or more symptoms associated with a β-globin disorder by increasing the amount of fetal hemoglobin in the individual. Symptoms typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In one embodiment, the hematopoietic progenitor cell is contacted ex vivo or in vitro with a composition comprising a fusion protein comprising at least two DNA-targeting endonucleases, or a composition comprising a vector carrying the coding sequence of a fusion protein comprising at least two DNA-targeting endonucleases, and the cell or its progeny is administered to the mammal (e.g., human). In a further embodiment, the hematopoietic progenitor cell is a cell of the erythroid lineage. In one embodiment, a composition comprising a hematopoietic progenitor cell that was previously contacted with a composition comprising a fusion protein comprising at least two DNA-targeting endonucleases, or a composition comprising a vector carrying the coding sequence of a fusion protein comprising at least two DNA-targeting endonucleases and a pharmaceutically acceptable carrier and is administered to a mammal.

In one embodiment, any method known in the art can be used to measure an increase in fetal hemoglobin expression, e.g., Western Blot analysis of fetal hemoglobin protein and quantifying mRNA of fetal γ-globin.

In one embodiment, the hematopoietic progenitor cell is contacted with a composition comprising a fusion protein comprising at least two DNA-targeting endonucleases, or a composition comprising a vector carrying the coding sequence of a fusion protein comprising at least two DNA-targeting endonucleases in vitro, or ex vivo. In one embodiment, the cell is of human origin (e.g., an autologous or heterologous cell). In one embodiment, the composition causes an increase in fetal hemoglobin expression.

The present invention can be defined in any of the following numbered paragraphs:

1. A method for producing a progenitor cell having decreased BCL11A mRNA or protein expression, the method comprising;
    a. contacting an isolated progenitor cell with an agent that deletes the GATA1 binding element in the functional core of the BCL11A enhancer +58 kb,
    b. wherein the agent is a composition comprising a fusion protein comprising at least two DNA-targeting endonucleases, or the agent is a composition comprising a vector carrying the coding sequence of a fusion protein comprising at least two DNA-targeting endonucleases whereby the DNA-targeting endonuclease fusion protein makes precise cleavages near the targeted GATA1 binding element to delete it, thereby reducing the mRNA or protein expression of BCL11A.
2. A method for producing an isolated genetic engineered human cell having at least one genetic modification comprising; contacting an isolated cell with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element to delete it, thereby causing at least one genetic modification therein.
3. A method of increasing fetal hemoglobin levels in a cell, the method comprising; contacting an isolated cell with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element to delete it, thereby causing at least one genetic modification therein, whereby fetal hemoglobin expression is increased in said cell, or its progeny, relative to said cell prior to said contacting.
4. A method for increasing fetal hemoglobin levels in a mammal in need thereof, the method comprising; contacting an isolated hematopoietic progenitor cell in said mammal with an effective amount of a composition comprising a fusion protein comprising at least two DNA-targeting endonucleases or a composition comprising a vector carrying the coding sequence of a fusion protein comprising at least two DNA-targeting endonucleases, whereby the DNA-targeting endonuclease fusion protein makes precise cleavages near the targeted GATA1 binding element, thereby causing at least one genetic modification therein, whereby fetal hemoglobin expression is increased in said mammal, relative to expression prior to said contacting.
5. The method of any preceding paragraph, wherein the isolated progenitor cell or isolated cell is a hematopoietic progenitor cell.
6. The method of any preceding paragraph, wherein the isolated progenitor cell or isolated cell is a human cell.
7. The method of any preceding paragraph, wherein the isolated progenitor cell or isolated cell is a CD34+ cell.
8. The method of paragraph 4, wherein the hematopoietic progenitor is a cell of the erythroid lineage.
9. The method of any preceding paragraph, wherein the isolated progenitor cell or isolated cell is an induced pluripotent stem cell.
10. The method of paragraph 5, wherein the hematopoietic progenitor cell is contacted ex vivo or in vitro.
11. The method of any preceding paragraph, wherein the at least one genetic modification is a deletion.
12. The method of paragraph any preceding paragraph, wherein the deletion removes the entire region or a portion of the targeted GATA1 binding element.
13. The method of paragraph any preceding paragraph, wherein the agent composition further comprises guideRNA.
14. The method of paragraph 13, wherein the guideRNA comprising a sequence selected from SEQ ID NOs 2-9.
15. An isolated genetic engineered human cell having at least one genetic modification on chromosome 2 location 60,716,189-60,728,612, near the GATA1 binding element in the functional core of the BCL11A enhancer +58 kb.
16. A composition comprising isolated genetic engineered human cells of paragraph 15.

17. A method for increasing fetal hemoglobin levels in a mammal in need thereof, the method comprising transplanting an isolated genetic engineered human cell of paragraph 15 or a composition of paragraph 16 into the mammal.
18. The method of any preceding paragraph, wherein said mammal has been diagnosed with a hemoglobinopathy.
19. The method of paragraph 18, wherein said hemoglobinopathy is a β-hemoglobinopathy.
20. The method of paragraph 18, wherein the hemoglobinopathy is sickle cell disease.
21. The method of paragraph 18, wherein the hemoglobinopathy is β-thalassemia.
22. A method of treatment of a hemoglobinopathy in a subject comprising; administering an effective amount of a composition comprising isolated genetic engineered human cells of paragraph 15, and whereby fetal hemoglobin expression is increased in the subject relative to prior treatment.
23. The method of paragraph 22, wherein the subject has been diagnosed with a hemoglobinopathy.
24. The method of paragraph 22, further comprising selecting a subject who has been diagnosed with a hemoglobinopathy.
25. The method of any of paragraphs 22-24, wherein the hemoglobinopathy is a β-hemoglobinopathy.
26. The method of any of paragraphs 22-24, wherein the hemoglobinopathy is sickle cell disease.
27. The method of any of paragraphs 22-24, wherein the hemoglobinopathy is β-thalassemia.
28. A method of treatment of a hemoglobinopathy in a subject comprising; administering an effective amount of a composition comprising hematopoietic progenitor cells to the subject, wherein the hematopoietic progenitor cells have been contacted ex vivo or in vitro with an effective amount of a composition comprising a fusion protein comprising at least two DNA-targeting endonucleases, or a composition comprising a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, and whereby fetal hemoglobin expression is increased in the subject relative to prior treatment.
29. The method of any preceding paragraph, wherein the at least one genetic modification is a deletion.
30. The method of paragraph any preceding paragraph, wherein the deletion removes the entire region or a portion of the targeted GATA1 binding element.
31. The method of paragraph any preceding paragraph, wherein the agent composition further comprises guideRNA.
32. The method of paragraph 31, wherein the guideRNA comprising a sequence selected from SEQ ID NOs 2-9.
33. The method of any of paragraphs 28-32, wherein the subject has been diagnosed with a hemoglobinopathy.
34. The method of any of paragraphs 28-32, further comprising selecting a subject who has been diagnosed with a hemoglobinopathy.
35. The method of any of paragraphs 28-32, wherein the hemoglobinopathy is a β-hemoglobinopathy.
36. The method of any of paragraphs 28-32, wherein the hemoglobinopathy is sickle cell disease.
37. The method of any of paragraphs 28-32, wherein the hemoglobinopathy is β-thalassemia.
38. The method of any preceding paragraph, wherein the composition further comprising a pharmaceutically acceptable carrier or diluent.
39. The method of any preceding paragraph, wherein the composition is administered by injection, infusion, instillation, or ingestion.
40. The method of any preceding paragraph, wherein the composition is administered by injection, infusion, instillation, or ingestion.
41. The method of any preceding paragraph, wherein the mammal or subject is further administered an epigenetic modifier.
42. The method of any preceding paragraph, wherein the mammal or subject or isolated cells are human or derived from a human.
43. The method of any of paragraphs 28-32, wherein the isolated progenitor cell or isolated cell is a hematopoietic progenitor cell.
44. The method of any of paragraphs 28-32, wherein the isolated progenitor cell or isolated cell is a human cell.
45. The method of any of paragraphs 28-32, wherein the isolated progenitor cell is a CD34+ cell.
46. A composition comprising a CD34+ hematopoietic progenitor cell that comprises a fusion protein comprising at least two DNA-targeting endonucleases, or the CD34+ hematopoietic progenitor cell comprises a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, and thereby reduces the mRNA or protein expression of BCL11A in the cell.
47. The composition of paragraph 46, wherein the at least one genetic modification is a deletion.
48. The composition of paragraph 47, wherein the deletion removes the entire region or a portion of the targeted GATA1 binding element.
49. The method of paragraph any preceding paragraph, wherein the agent composition further comprises guideRNA.
50. The method of paragraph 49, wherein the guideRNA comprising a sequence selected from SEQ ID NOs 2-9.
51. The composition of any preceding paragraph, wherein the composition further comprises a pharmaceutically acceptable carrier or diluent, and/or an epigenetic modifier.
52. The composition of any preceding paragraph, wherein the CD 34+ hematopoietic progenitor cell is expanded ex vivo.
53. The composition of any preceding paragraph, wherein the CD 34+ hematopoietic progenitor cell is formulated for injection or infusion.
54. A population of CD34+ hematopoietic progenitor cells, wherein the CD34+ hematopoietic progenitor cells comprise a fusion protein comprising at least two DNA-targeting endonucleases, or the CD34+ hematopoietic progenitor cells comprise a vector carrying the coding sequence of a fusion protein comprising at least two DNA-targeting endonucleases whereby the DNA-targeting endonuclease fusion protein makes precise cleavages near the targeted GATA1 binding element, thereby causing at least one genetic modification therein, thereby reducing the mRNA or protein expression of BCL11A in the cells.

55. The population of CD34+ hematopoietic progenitor cells of paragraph 54 further comprises a pharmaceutically acceptable carrier or diluent.
56. The population of CD34+ hematopoietic progenitor cells of paragraph 54 or 55, further comprises an epigenetic modifier.
57. The population of CD34+ hematopoietic progenitor cells of any preceding paragraph, wherein the CD 34+ hematopoietic progenitor cell is expanded ex vivo.
58. The population of CD34+ hematopoietic progenitor cells of any preceding paragraph, wherein the CD 34+ hematopoietic progenitor cell is formulated for injection or infusion.
59. The composition or method of any preceding paragraph, further comprising an epigenetic modifier.
60. In any of the preceding paragraphs, the fusion protein comprising at least two DNA-targeting endonucleases comprising a first Cas9 or Cas12a nuclease, said nuclease comprising a protospacer adjacent motif recognition domain and a peptide linker, wherein said peptide linker is attached to a second Cas9 or Cas12a nuclease.
61. In any of the preceding paragraphs, the said Cas9 nuclease of the fusion protein is selected from the group consisting of SpCas9, SaCas9, NmCas9, CjCas9 and An-Cas9.
62. In any of the preceding paragraphs, the said Cas12a nuclease of the fusion protein is selected from the group consisting of FnCas12a, LbCas12a and AsCas12a.
63. In any of the preceding paragraphs, said protospacer adjacent motif recognition domain of fusion protein is selected from the group consisting of SpCas9, SpCas9$^{MT1}$ SpCas9$^{MT2}$, SpCas9$^{MT3}$NmCas9$^{SM}$ and NmCas9$^{DM}$.
64. In any of the preceding paragraphs, the said protospacer adjacent motif recognition domain of fusion protein is mutated or non-mutated.
65. In any of the preceding paragraphs, said peptide linker of fusion protein is a peptide linker.
66. In any of the preceding paragraphs, wherein said peptide linker is between twenty-five and eighty amino acids.
67. In any of the preceding paragraphs, wherein said fusion protein further comprises a guide RNA which is attached to a guide sequence element.
68. In any of the preceding paragraphs, wherein said mutated protospacer adjacent motif recognition domain of the fusion protein comprises mutated DNA phosphodiester recognition amino acid residues.
69. In any of the preceding paragraphs, wherein said guide RNA of said fusion protein is selected from the group consisting of an sgRNA sequence, a crRNA sequence and a tracrRNA sequence.
70. In any of the preceding paragraphs, wherein said guide sequence element of said guide RNA of said fusion protein is truncated.
71. In any of the preceding paragraphs, wherein said truncated guide sequence element is less than twenty nucleotides.

This invention is further illustrated by the following example which should not be construed as limiting. The contents of all references cited throughout this application, as well as the figures and table are incorporated herein by reference.

EXAMPLES

The following provides non-limiting Examples demonstrating and supporting the technology as described herein.

The methods and compositions described herein detail fetal hemoglobin reinduction using Cas9 fusion proteins. The invention methods and compositions described herein represent an extension of previously described Cas9-fusion proteins with applications for human hematopoietic stem and progenitor cells (CD34+ HSPCs). The methods and compositions provided herein are a therapeutic treatment for beta-hemoglobinopathies, such as sickle cell disease and beta-thalassemia. The methods and compositions described herein detail the reactivating gamma-globin expression to complement the loss of beta-globin function.

Example 1: Fetal Hemoglobin Re-Induction Using Cas9 Fusion Proteins

As previously described, the majority of transformed HEK293T cells treated with this dual nuclease system have segmental deletions of a critical regulatory element at a therapeutically relevant locus (BCL11A) for beta-hemoglobinopathies such as sickle cell[1]. The data described herein shows the use of Cas9-Cas9 fusion proteins in human CD34+ HSCs to successfully generate targeted deletions within the BCL11A locus. These deletions successfully reactivate HbF in erythrocytes that are differentiated from these CD34+ HSCs.

Furthermore, as previously described, the combinations of orthogonal Cas9 nucleases that can function in tandem (*S. pyogenes*[2] and *N. meningiditis*[3,4], SpCas9 and NmCas9 respectively) or (*S. pyogenes*[2] and *S. aureus*[5], SpCas9 and SaCas9 respectively). These Cas9 modules can function cooperatively to generate targeted breaks within the genome. In this system, one Cas9 module (Cas9$^A$) and its corresponding sgRNA (sgRNA$^A$) serve as the wild-type or attenuated nuclease domain, and the other Cas9 module with or without nuclease activity (Cas9$^B$) and its corresponding sgRNA (sgRNA$^B$) serve as the DTU (FIG. 1). This creates a system where targeting of the Cas9-Cas9 system is programmed entirely by RNA-encoded species. The evidence described herein shows that like the Cas9-ZFPs previously described, the Cas9$^A$-Cas9$^B$ fusions improve the precision of the associated nucleases.

Evaluation of the Precise Deletion Rate in the BCL11A Erythroid-Specific Enhancer.

A critical regulatory element that is responsible for repressing fetal hemoglobin (HbF) expression in erythrocytes has been defined within the BCL11A locus, which is responsible for the expression of this negative regulatory factor in proerythrocytes[6]. Deletion or mutation of the GATA1 binding site (within the gray box in FIG. 2) leads to decreased BCL11A expression and increased HbF, which can complement for the loss of function of adult beta-globin (HbA) or the presence of the sickle cell mutation (HbS). A screen was performed on a variety of different target sites for SpCas9-SaCas9 or SpCas9-NmCas9 target sites within this locus in HEK293T cells and identified a number of target sites that produced efficient deletion of the target sequence (FIG. 2). These fusion nucleases were more effective than the SpCas9 and SaCas9 or NmCas9 nucleases employed in combination as independent nucleases.

The activity of the purified SpCas9-SaCas9 fusion protein targeting of Target Site 9 was examined (TS9, FIG. 2) in human CD34+ HSPCs in collaboration with the Bauer laboratory. The Cas9-Cas9 fusion protein was produced as previously described and target sites were prioritized and electroporations were performed in CD34+ HSPCs as well as the downstream analyses on gamma-globin expression levels.

Figure 4:
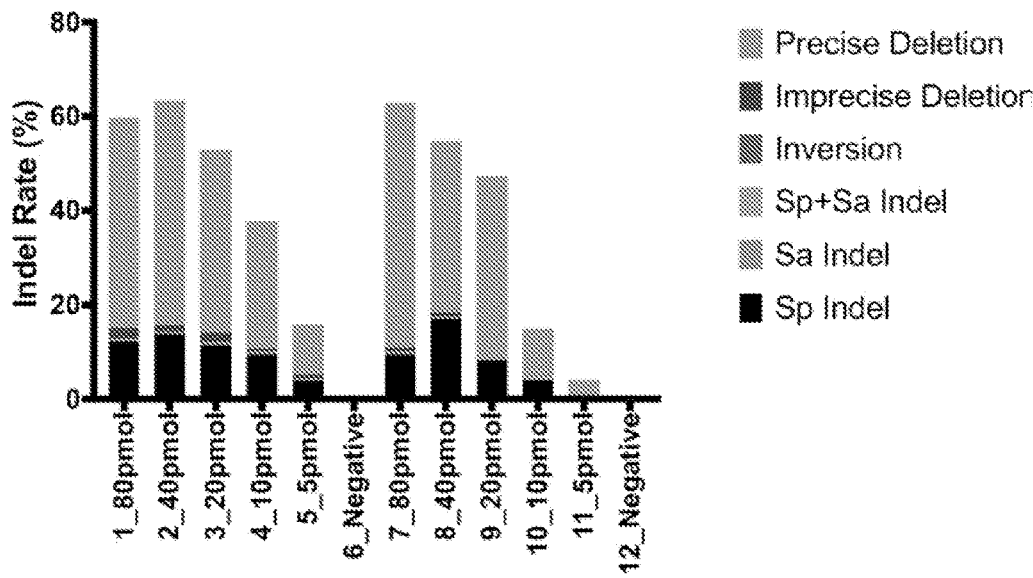
FIG. 4 shows the editing rates for SpCas9-SaCas9 fusion proteins in CD34+ HSCs at target site 9 (TS9). Two different complex formation approaches between the Cas9-Cas9 protein and the sgRNAs were examined (Samples 1 through 5 & 7 through 11) with a titration of different concentrations of each complex delivered to CD34+ HSCs via nucleofection. The majority of the deletion products that are observed are precise deletions (green bars) that will delete the critical GATA1 binding site from the BCL11A erythroid enhancer element. Sequence data are determined by deep sequencing PCR products spanning the target site in the treated genomic DNAs.

A range of doses of the SpCas9-SaCas9 fusion protein were tested with an excess of synthetic sgRNAs designed to target TS9. For these experiments the SpCas9 nuclease was not attenuated by mutation. SpCas9-SaCas9 protein-sgRNA complexes (Cas9-Cas9 RNPs) were generated using two different approaches of combining the guides and Cas9-Cas9 protein, and then these complexes were titrated from 80 pmol/L to 5 pmol/L for nucleofection into CD34+ HSCs (FIG. 3). The editing efficiency for the SpCas9-SaCas9 RNPs in CD34+ HSCs as assayed by deep sequencing was good, with precise deletion rates on the order of 50% at the highest doses of Cas9-Cas9 RNP complex (FIG. 4).

Figure 5:
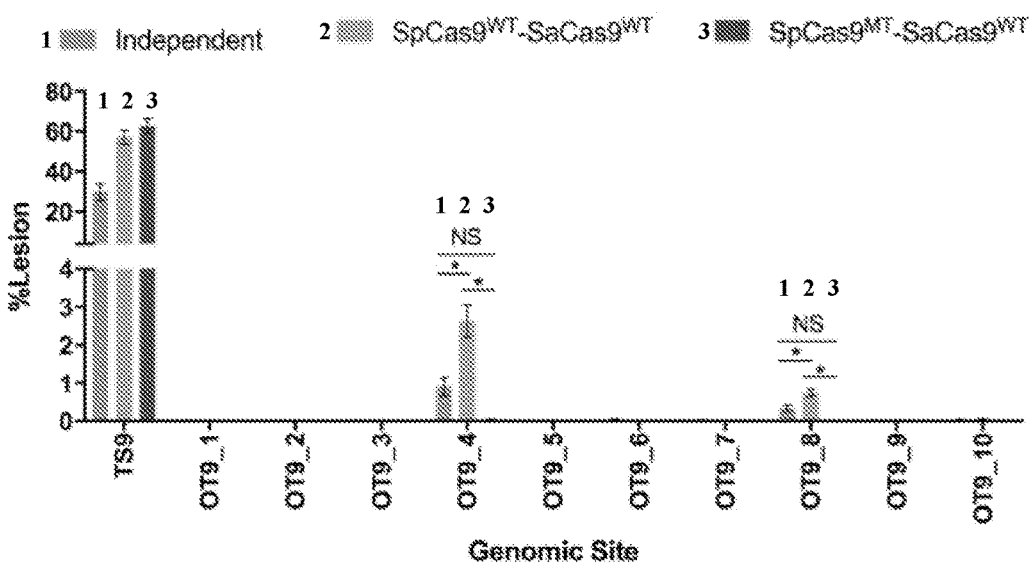
FIG. 5 shows that Cas9-Cas9 fusions achieve robust and specific genome editing. Deep sequencing determined lesion rates for these nucleases at a subset of off-target sites discovered by the GUIDE-seq data or predicted by CasOFFinder. The deep sequencing data are from three independent biological replicates performed on different days in HEK293T cells. Error bars indicate ±s.e.m. Statistical significance is determined by one-way analysis of variance (ANOVA), "*" and "NS" denote BH-adjusted P-values of <0.05 and "not significant" respectively

The editing rates at the only two off-target sites in the genome that were previously defined were examined by GUIDE-seq7 for this SpCas9-SaCas9 fusion protein targeting BCL11A TS9 in HEK293T cells. In these prior editing experiments to examine nuclease precision, a plasmid based expression system was used in HEK293T cells to determine the off-target editing rates for both $SpCas9^{WT}$-$SaCas9^{WT}$ fusions and $SpCas9^{MT}$-$SaCas9^{WT}$ (where MT indicates attenuated SpCas9). Deep sequencing at 10 potential off-target sites revealed weak editing at two of these sites for the wild-type nucleases (9_4 and 9_8; FIG. 5), but no appreciable editing using the attenuated $SpCas9^{MT}$-$SaCas9^{WT}$ in HEK293T cells.

Figure 6:
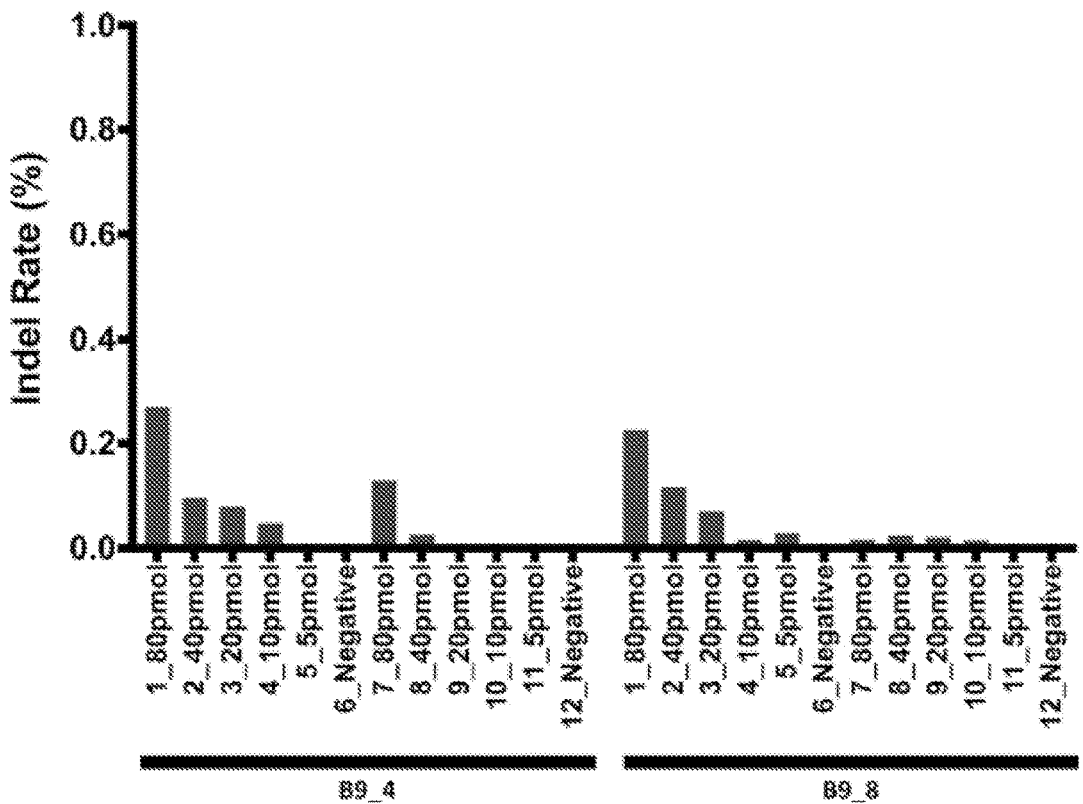
FIG. 6 shows that SpCas9WT-SaCas9WT RNPs display low levels of off-target editing at two genomic target sites. Editing rates are <0.3% at the highest doses. In addition, dose-dependent activity was observed at these target sites. The deep sequencing data are from one experiment.

It has been previously described that the delivery of Cas9 RNPs produces dramatically reduced levels of off-target editing relative to Cas9 plasmid expression systems in mammalian cells due to the shorter time window of Cas9 expression(1). Consequently, it was contemplated that the use of $SpCas9^{WT}$-$SaCas9^{WT}$ RNPs would have lower off target activity than observed in HEK293T cells. Very low editing was observed in a dose dependent manner at these two off-target sites in CD34+ HSCs with $SpCas9^{WT}$-$SaCas9^{WT}$ RNP delivery (FIG. 6). It was contemplated that that using $SpCas9^{MT}$-$SaCas9^{WT}$ RNPs instead of the $SpCas9^{WT}$-$SaCas9^{WT}$ RNP that there will be negligible editing at these sequences.

Figure 7:
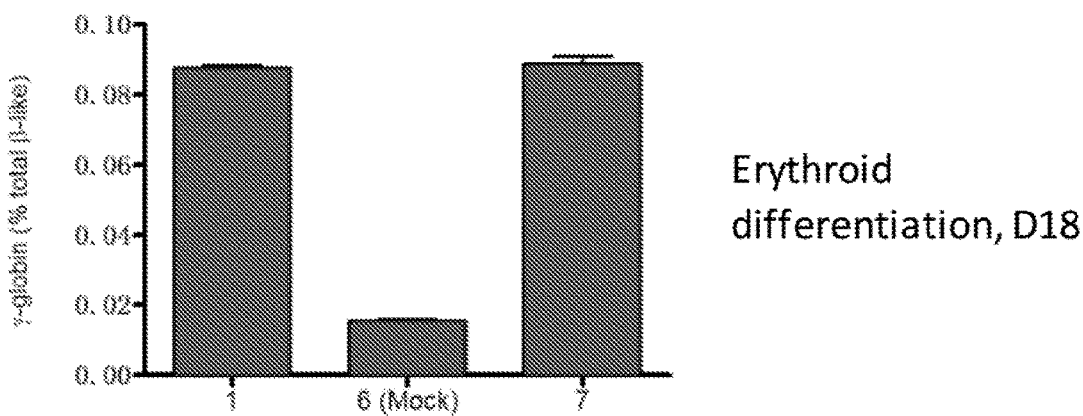
FIG. 7 shows the qRT-PCR analysis of gamma-globin expression levels in CD34+ HSCs differentiated to erythrocytes, where these are represented as the fraction relative to beta-globin expression levels. X-axis corresponds to the sample #s in FIGS. 3 and 4.

These edited CD34+ HSCs were differentiated into erythrocytes to determine the level of gamma-globin RNA expression that was induced within this cell population. To achieve high levels of gamma-globin induction biallelic modification of the genome at the BCL11A erythroid enhancer is required. Even though the bulk precise deletion rates for alleles is on the order of 50%, the frequency of biallele deletions will plausibly be the square of this frequency if the events are independent. Consequently, the modest induction of gamma-globin RNA levels is encouraging, and indicates that a higher rate of biallelic editing effects would result in therapeutically relevant levels of gamma-globin (FIG. 7).

The ability to precisely and efficiently excise genomic segments could have broad clinical utility in gene therapy applications where the removal of a regulatory element (either transcriptional or mRNA splicing) would compensate for a specific genetic dysfunction. The Cas9-Cas9 nucleases can be utilized for a number of different therapeutic applications, where local deletions will enforce a regulatory change that will result in a phenotypic change in cell behavior. The experiments described herein have demonstrated that Cas9-Cas9 fusion proteins delivered to human CD34+ HSPCs can efficiently delete regulatory segments from the genome. Current efforts to target this locus had previously been focused on the use of a nuclease (e.g. Cas9 or zinc finger nucleases) targeting a single site within the locus. The use of Cas9-Cas9 nucleases has the potential to produce more profound effects due to the precise deletion of segments within the genome as opposed to simple mutagenesis. Deletions within a genomic locus are the next focus of this technology, where BCL11A can be used as a treatment for beta-hemoglobinopathies.

Furthermore, the dual Cas9 system described herein will provide improvements in activity, precision, and sequence targeting range much like the previously described Cas9-DTU. Importantly, this system can efficiently generate precise deletions within cells, where one of the Cas9s (attenuated by mutation) is dependent on its fused partner for activity and improves the precision of the system. The composition and methods described herein indicates that these nucleases are highly precise, and can deliver purified Cas9-Cas9 fusion proteins into human CD34+ HSCs for genome modification by nucleofection. This nuclease produces high rates of precise deletions and measurable phenotypic changes within differentiated cells from this treated population.

REFERENCE (1) Kim, S., Kim, D., Cho, S. W., Kim, J. & Kim, J.-S. Highly efficient RNA-guided genome editing in human cells via delivery of purified Cas9 ribonucleoproteins. Genome Research 24, 1012-1019 (2014).

Example 2: sgRNA Sequences for the Active Bcl11A Guides

Provided herein in Example 2 are sgRNA sequences for the active Bcl11A guides using the Cas9-Cas9 fusions (either SpCas9-SaCas9 or SpCas9-NmCas9 fusions).

In SEQ ID NO: 2-9, the underlined text denotes the SpCas9 guide region sequences of the sgRNAs.

In SEQ ID NO: 2-9, the zigzag underlined text denotes the NmCas9 guide region sequence of the sgRNAs. For the NmCas9 target site it is also listed as a crRNA/tracrRNA combination, as this was used for Cas9 RNP efforts as opposed to the sgRNA.

In SEQ ID NO: 2-9, the bolded and italicized text denote the constant crRNA-tracrRNA fusion sequence within the sgRNA for SpCas9.

In SEQ ID NO: 2-9, the *double-underlined, bolded and italicized text* denote the constant crRNA-tracrRNA fusion sequence within the sgRNA for SpCas9, or the constant crRNA and tracrRNA sequence when used separately for NmCas9.

```
SpCas9_BCL11A-TS7,10,11_sgRNA:                                                (SEQ ID NO: 2)

GCUAGUCUAGUGCAAGCUAAGUUUUAGAGCUAGAAAUAGCAAGUUAAAAUAAGGCUAGUC

CGUUAUCAACUUGAAAAAGUGGCACCGAGUCGGUGCUUUU

SpCas9_BCL11A-TS9_sgRNA:                                                      (SEQ ID NO: 3)

CCAGGGUCAAUACAACUUUGGUUUUAGAGCUAGAAAUAGCAAGUUAAAAUAAGGCUAGUC

CGUUAUCAACUUGAAAAAGUGGCACCGAGUCGGUGCUUUU

SaCas9_BCL11A-TS9_sgRNA:                                                      (SEQ ID NO: 4)

GCUUUUAUCACAGGCUCCAGGGUUUUAGUACUCUGGAAACAGAAUCUACUAAAACAAGGC

AAAAUGCCGUGUUUAUCUCGUCAACUUGUUGGCGAGAUUUU

SaCas9_BCL11A-TS10_sgRNA:                                                     (SEQ ID NO: 5)

GGUUUGGCCUCUGAUUAGGGUGUUUUAGUACUCUGGAAACAGAAUCUACUAAAACAAGGC

AAAAUGCCGUGUUUAUCUCGUCAACUUGUUGGCGAGAUUUU

Sa_TS11_sgRNA:                                                                (SEQ ID NO: 6)

GCCUCUGAUUAGGGUGGGGGCGUUUUAGUACUCUGGAAACAGAAUCUACUAAAACAAGGC

AAAAUGCCGUGUUUAUCUCGUCAACUUGUUGGCGAGAUUUU

Nm_TS7_sgRNA:                                                                 (SEQ ID NO: 7)

CAGGCUCCAGGAAGGGUUUGGCGUUGUAGCUCCCUUUCUCAUUUCGGAAACGAAAUGAGA

ACCGUUGCUACAAUAAGGCCGUCUGAAAAGAUGUGCCGCAACGCUCUGCCCCUUAAAGCUU

CUGCUUUAAGGGGCAUCGUUUAUUUU

Nm_TS7_crRNA:                                                                 (SEQ ID NO: 8)

CAGGCUCCAGGAAGGGUUUGGCGUUGUAGCUCCCUUUCUCAUUUCG

Nm_TS7_tracrRNA:                                                              (SEQ ID NO: 9)

CGAAAUGAGAACCGUUGCUACAAUAAGGCCGUCUGAAAAGAUGUGCCGCAACGCUCUGCCC

CUUAAAGCUUCUGCUUUAAGGGGCAUCGUUUAUUUU
```

Example 3: Orthogonal Cas9-Cas9 Fusions Provide a Versatile Platform for Precise Genome Editing As previously reported, a chimeric fusion of an attenuated *S. pyogenes* Cas9 nuclease (SpCas9$^{MT}$) to a DNA-binding-domain (DBD) that displays enhanced targeting range and improved specificity[1]. Cas9-Cas9 chimeras based on this platform were created by replacing the DBD with an orthogonal Cas9 from *N. meningiditis* (NmCas9) or *S. aureus* (SaCas9), which generates a system that is entirely RNA-programmable. Within this system, the number of targetable PAMs for SpCas9 is expanded.

In the single nuclease format, SpCas9 is fused to nuclease dead NmCas9 or SaCas9. The attenuated SpCas9$^{MT}$ nuclease activity is restored when delivered to its target site as a SpCas9$^{MT}$-dNmCas9 or SpCas9$^{MT}$-dSaCas9 fusion due to its increased effective concentration. GUIDE-seq analysis and targeted deep sequencing of potential off-target sites indicates that the SpCas9$^{MT}$-dNmCas9 or SpCas9$^{MT}$-dSaCas9 fusions display excellent accuracy.

In the dual nuclease format, where both Cas9 nucleases are active, it was determined that synchronous cleavage of the target genome at two neighboring positions produces primarily precise segmental deletions (as high as 95% of all lesions). Analysis of >40 genomic target sites revealed that total level of editing and the fraction of precise segmental deletions are higher for Cas9-Cas9 nucleases than a pair of independent Cas9 monomers. For the ex vivo disruption of therapeutically relevant genes or regulatory elements, ribonucleoproteins (RNPs) of the Cas9-Cas9 fusions have been produced by utilizing a split-intein system. These Cas9-Cas9 RNPs have robust activity when nucleofected into human cells.

These Cas9-Cas9 systems should provide a versatile platform for the development of nuclease-based cell replacement therapeutics.

REFERENCE

1. Bolukbasi, M. F. et al. DNA-binding-domain fusions enhance the targeting range and precision of Cas9. Nat Methods 12, 1150-1156 (2015).

Example 4: Bcl11A SpCas9-SaCas9 with 1617 sgRNA+SaCas9 sgRNAs

PCR amplification of the BCL11A enhancer region from genomic DNA treated with SpCas9-SaCas9 RNP loaded with the indicated guides is shown in FIG. 8. The rate of deletion appears to be nearly uniform within the treated population.

The BCL11A target site PCR amplicon sequence is show in FIG. 9 with the underlined SpCas9 1617 target site underlined. The SaCas9 TS13 target site is show in italics and the TS14 target site is squiggle underlined. It is important to note that the TS13 and TS14 target sites overlap.

The SpCas9 1617 target site and sgRNA sequences are shown in FIG. 10. Furthermore, the TS13 and TS14 target sites and sgRNA are also shown in FIG. 10.

Example 5: Cas9-Cas9 Fusions Provide a Versatile Genome Editing Platform

Figure 11:
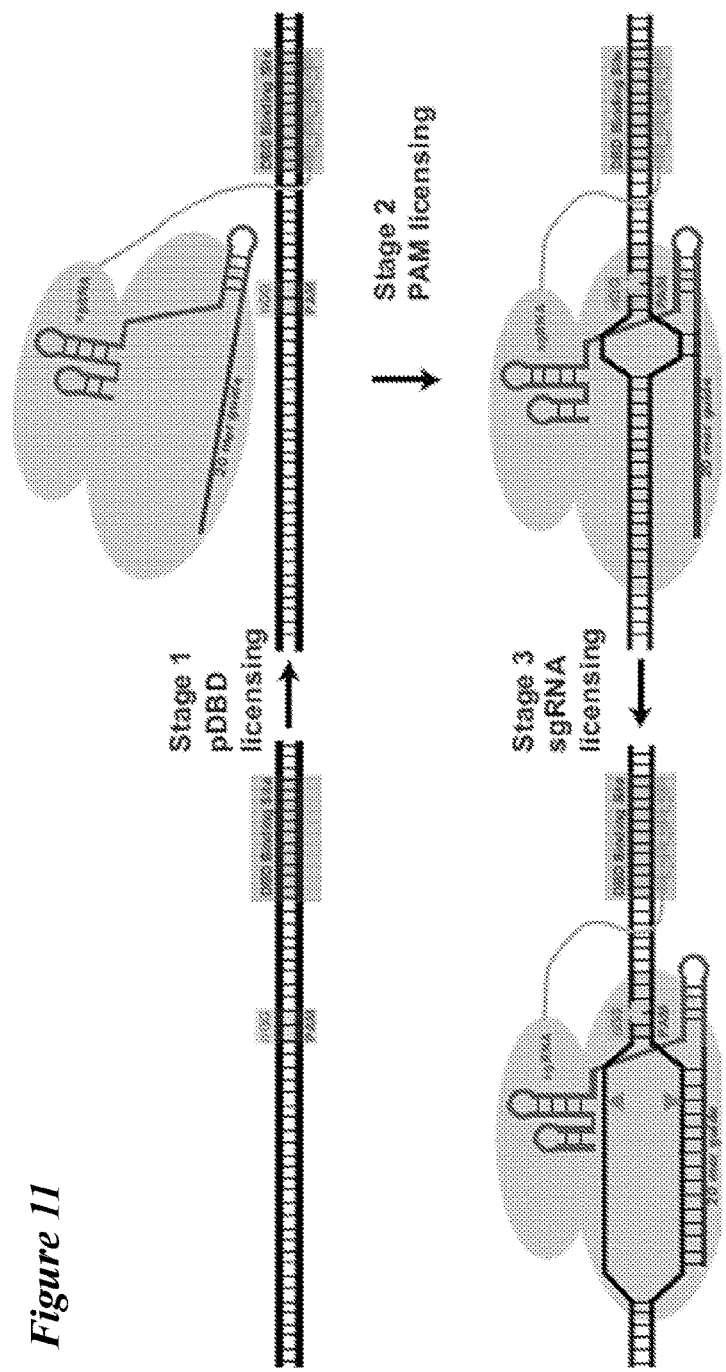
FIG. 11 shows three-stages of target site licensing of Cas9-DBD chimera.

It has been recently reported that a chimeric Cas9 platform with enhanced targeting range and improved specificity[1]. In this system, the DNA-binding affinity of the Cas9 protein from *S. pyogenes* is attenuated (SpCas9$^{MT}$) such that target site binding and subsequent cleavage is dependent on a fused DNA-binding-domain (DBD) that recognizes a neighboring DNA-sequence. (FIG. 11).

Figure 12:
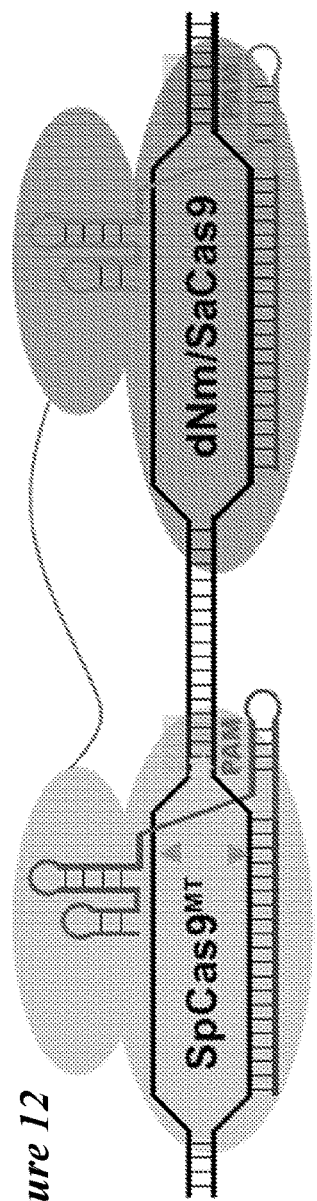
FIG. 12 shows a schematic of Cas9-Cas9 fusions.

The DBD has been replaced with an orthogonal Cas9 from either *N. meningiditis* (NmCas9) or *S. aureus* (SaCas9) to make the system entirely RNA-programmable (FIG. 12). The Cas9-Cas9 chimeras have been constructed in both single and dual nuclease formats.

Figure 14:
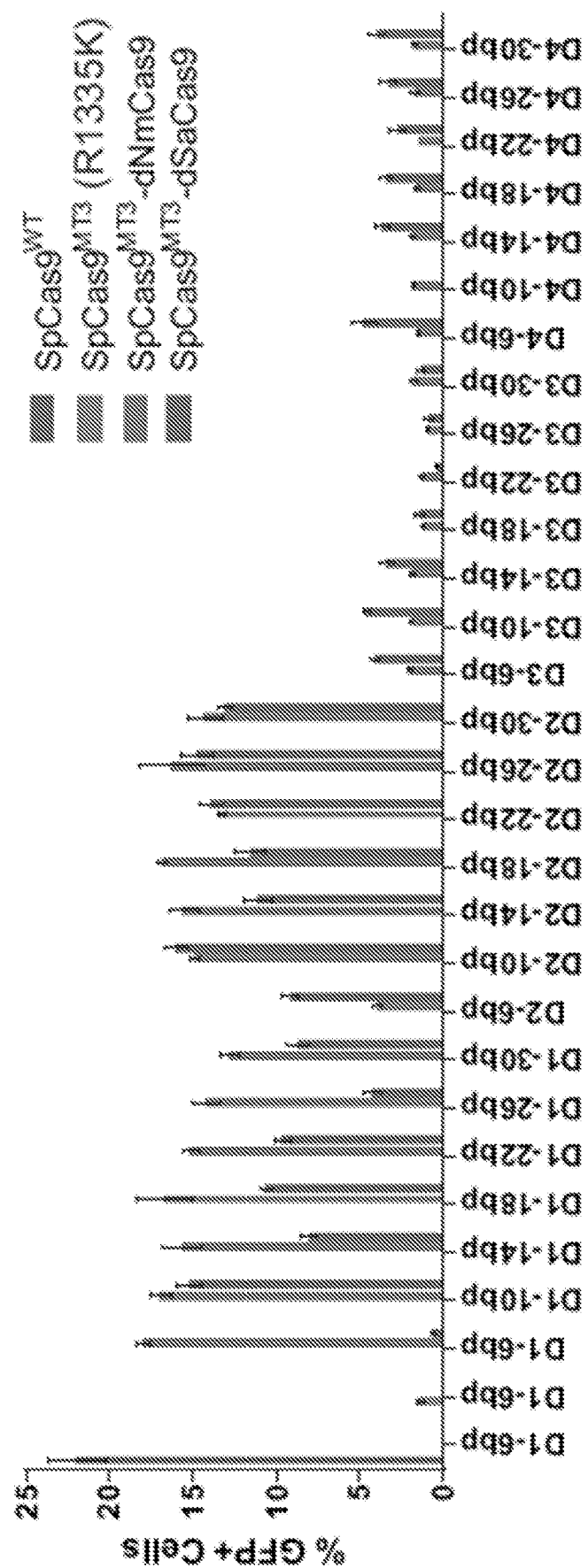
FIG. 14 shows identification of functional parameters of the Cas9-dCas9 fusions.

In the single nuclease format, the SpCas9 is fused to a nuclease dead NmCas9 or SaCas9, whose orthogonal guide is programmed to target a neighboring DNA sequence. The loss of nuclease activity of the SpCas9$^{MT}$ is restored when delivered to its target site by a nuclease dead NmCas9 or SaCas9 (SpCas9$^{MT}$-dNmCas9 or SpCas9$^{MT}$-dSaCas9) due to its increased effective concentration (FIGS. 13 and 14). To identify functional parameters, nuclease activity was tested in a plasmid reporter assay, which contains target sites in four different configurations (FIG. 13) with various spacing. In two of the four orientations, restoration of nuclease activity is observed (FIG. 14).

Figure 15:
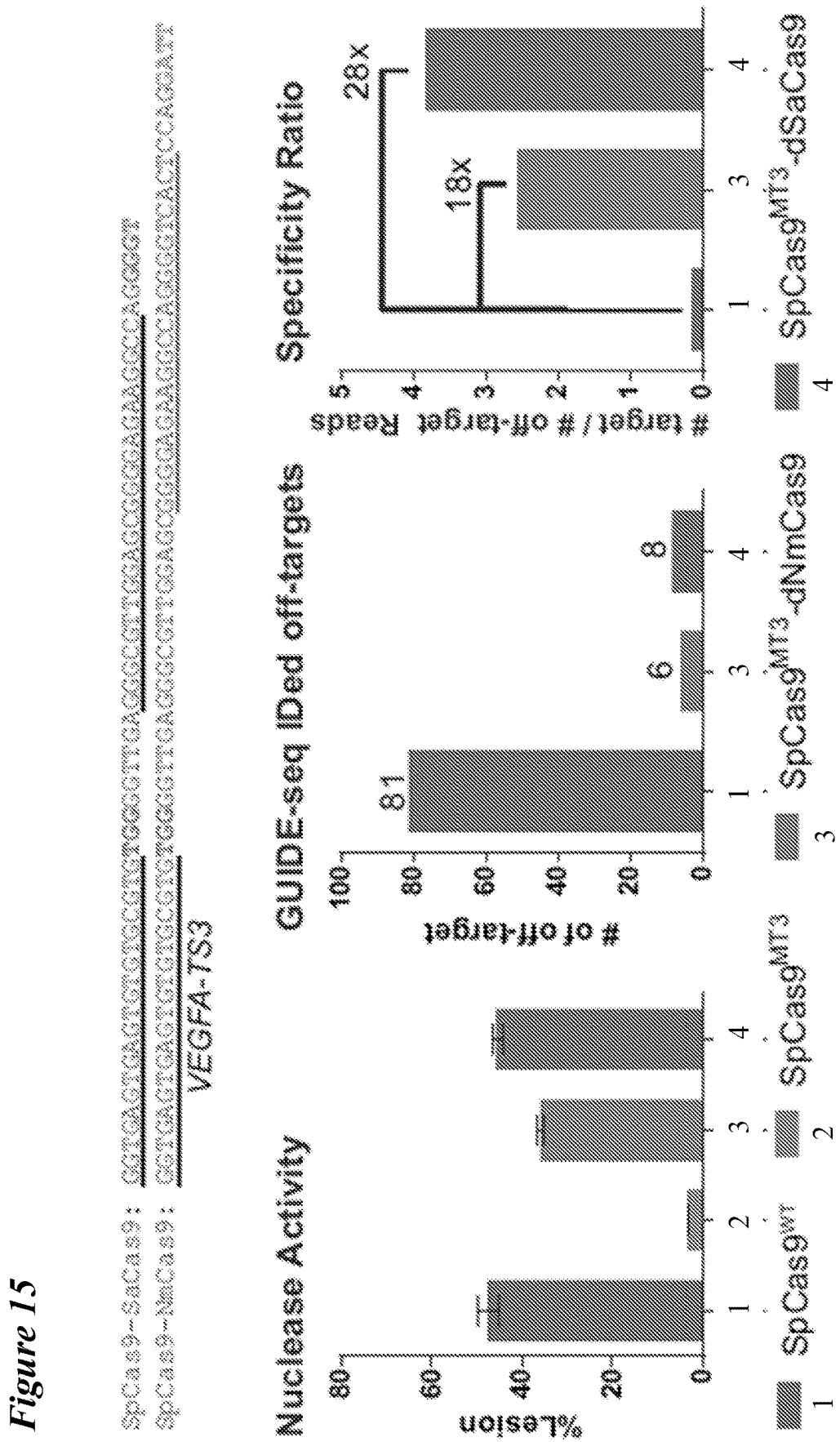
FIG. 15 shows Cas9-dCas9 nucleases display improved specificity.

GUIDE-seq-based genome-wide specificity analysis[2] indicates that the SpCas9$^{MT}$-dNmCas9 or SpCas9$^{MT}$-dSaCas9 fusions display higher accuracy than wild-type SpCas9 (FIG. 15). This improved specificity of the nuclease activity is similar to SpCas9$^{MT}$-DBD chimera, which also requires three-stages of target site licensing.

Figure 16:
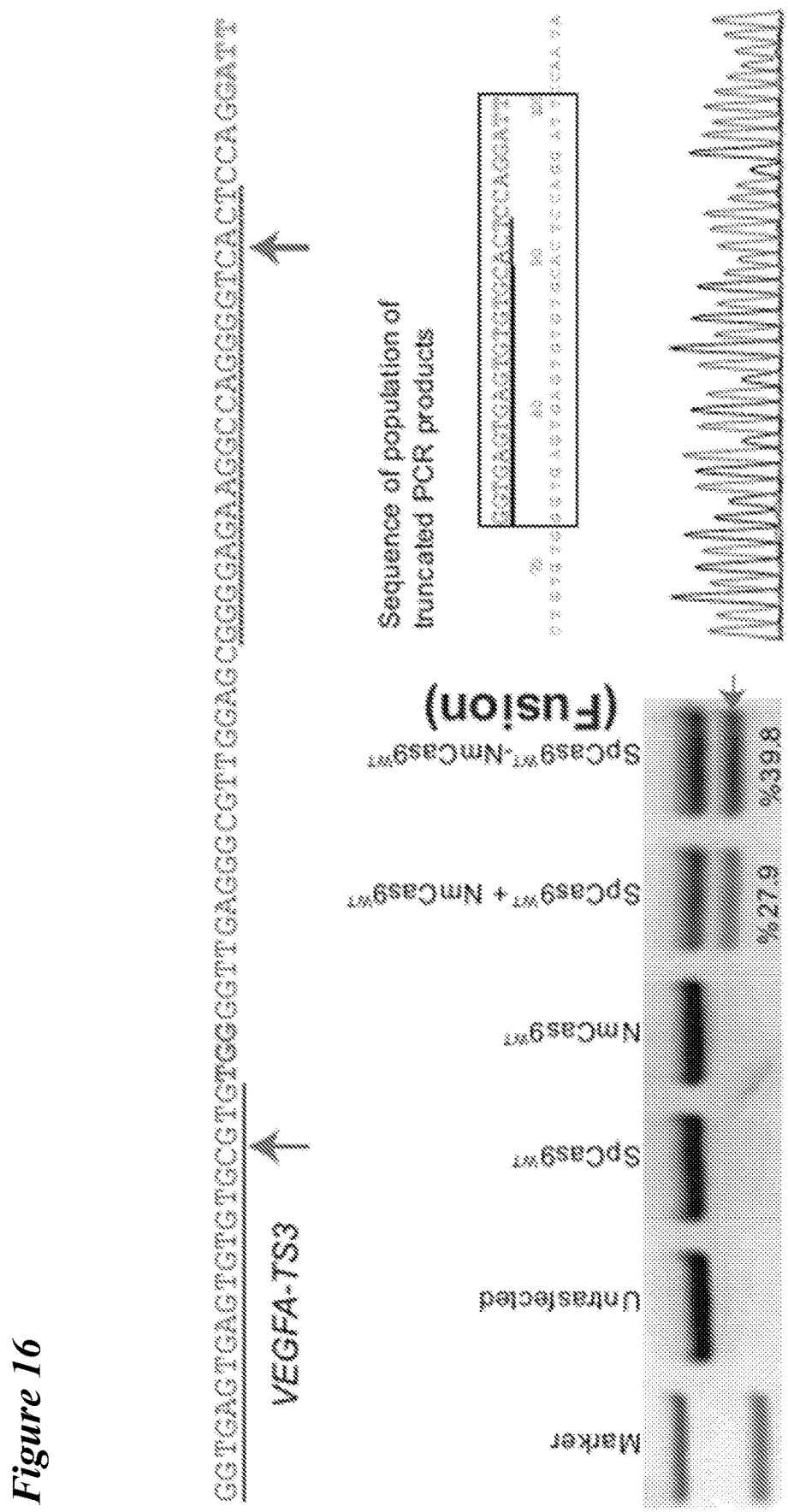
FIG. 16 shows Cas9-Cas9 dual nuclease fusions primarily generate precise segmental deletions.
Figure 17:
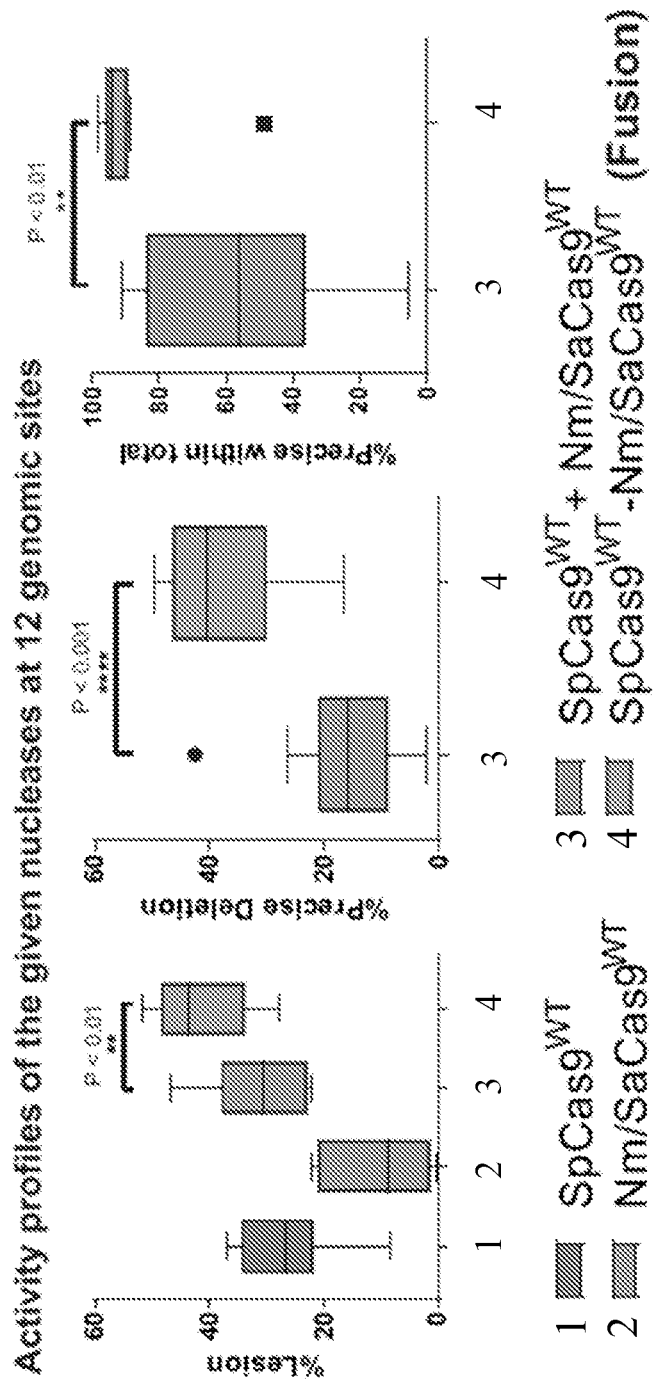
FIG. 17 shows activity profiles of the given nucleases at 12 genomic sites.

In the dual nuclease format, both nucleases of the orthogonal Cas9-Cas9 fusions are active. It is contemplated that synchronous cleavage of the target genome at two neighboring positions will primarily produce precise segmental deletions. Analysis of nuclease activity at 12 genomic sites revealed that the total level of editing and the fraction of precise segmental deletions are higher for Cas9-Cas9 nucleases than a pair of Cas9 monomers used simultaneously. Notably, Cas9-Cas9 nucleases generated precise segmental deletions as high as 95% of all lesions (FIGS. 16 and 17).

Figure 18:
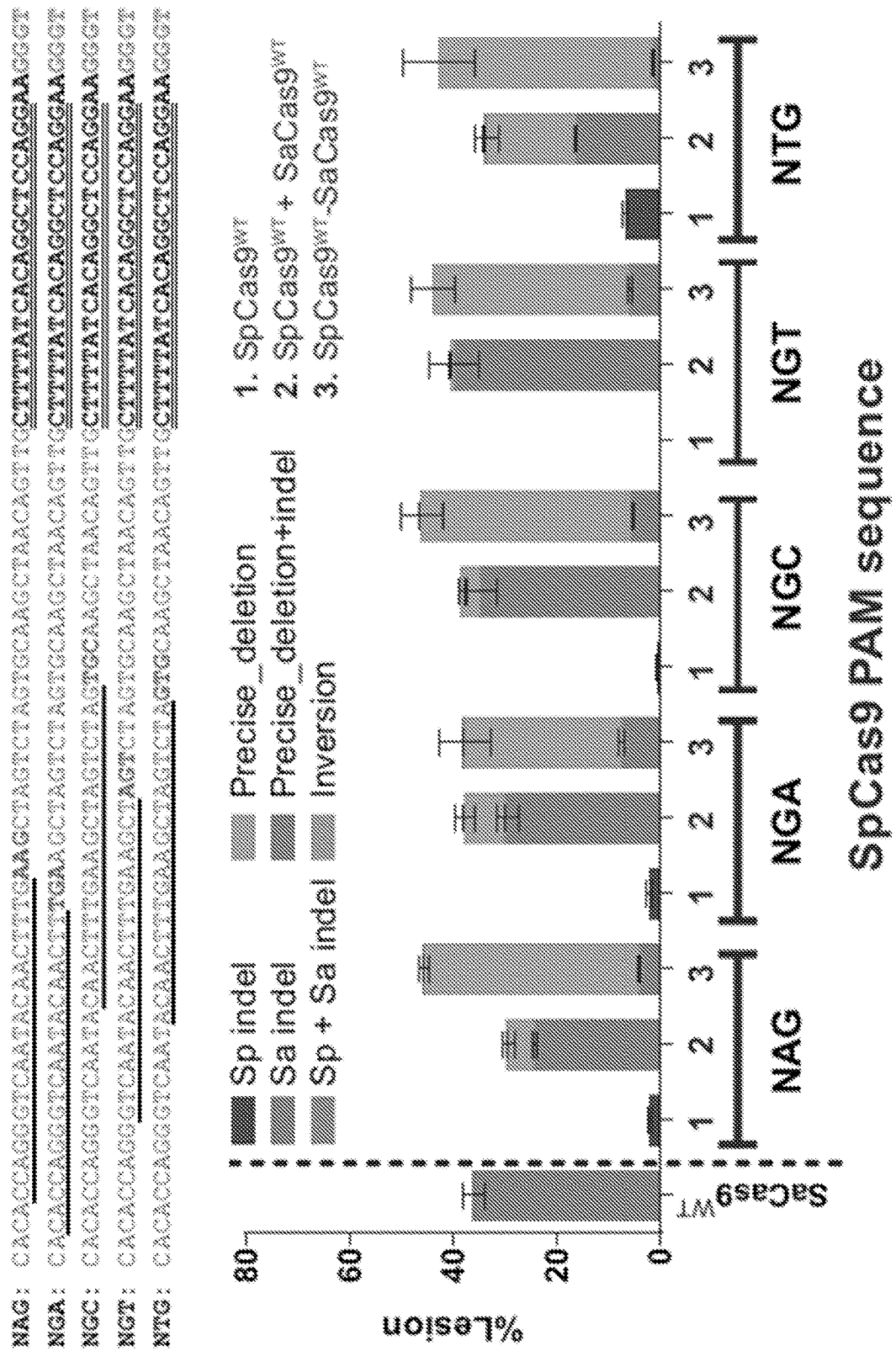
FIG. 18 shows that Cas9-Cas9 fusions expand the targeting range of SpCas9.

SpCas9-DBD chimera has increased targeting range due to the expansion of number of functional PAM sequences[1]. Similarly, Cas9-Cas9 fusions extends the targeting repertoire of SpCas9 (FIG. 18).

Figure 19:
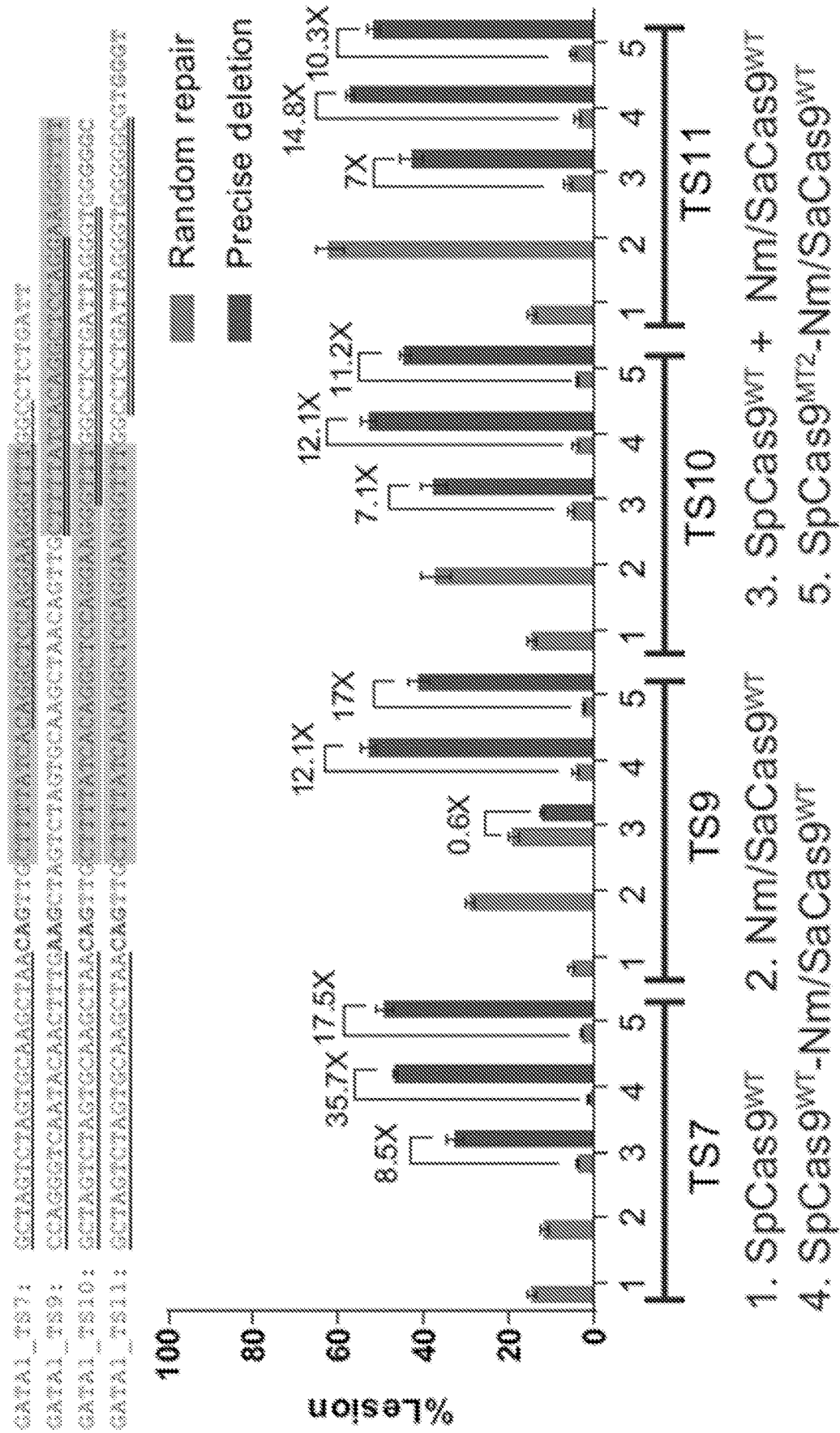
FIG. 19 shows Cas9-Cas9 fusions effectively delete the GATA1 binding site within BCL11A enhancer +58 kb in HEK293T.

One of the proposed therapeutic approaches of sickle cell anemia is to induce the expression of fetal γ-globin gene, which is silenced shortly after birth[3]. BCL11A is the negative regulator of the fetal γ-globin gene expression in erythrocytes. Previous studies identified an erythroid-lineage specific enhancer element of BCL11A (enhancer +58 kb)[4,5]. The GATA1 binding motif within this enhancer is considered one of primary regulatory sequence elements. Cas9-Cas9 fusions were engineered to effectively delete the GATA1 binding motif within BCL11A enhancer +58 kb (FIG. 19).

Figure 20:
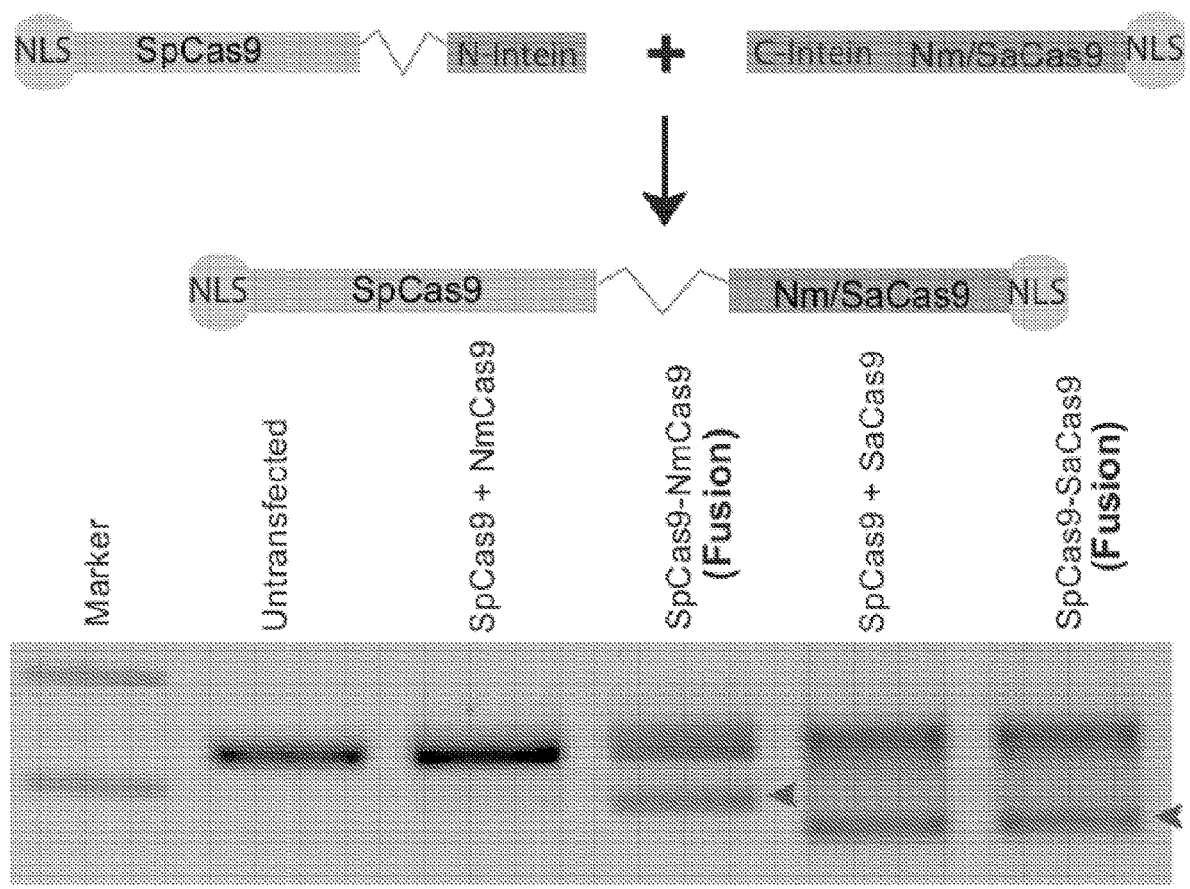
FIG. 20 describes the production of functional Cas9-Cas9 fusion protein.

In preparation for the ex vivo disruption of therapeutically relevant genes or regulatory elements, ribonucleoproteins (RNPs) of the Cas9-Cas9 fusions were produced by utilizing a split-intein system[6]. These Cas9-Cas9 RNPs efficiently produce segmental deletions when electroporated into human cells (FIG. 20).

In summary, the Cas9-dCas9 fusion protein provides accurate genome editing with an expanded targeting range. Furthermore, Cas9-Cas9 dual nuclease fusions generate efficient, precise, segmental deletions. Cas9-Cas9 dual nucleases effectively deletes functional regulatory elements in a complex genome. Split-intein approach can be utilized to produce functional Cas9-Cas9 fusion proteins.

REFERENCES

1. Bolukbasi, M. F. et al. DNA-binding-domain fusions enhance the targeting range and precision of Cas9. Nature Methods 12, 1150-1156 (2015).
2. Tsai, S. Q. et al. GUIDE-seq enables genome-wide profiling of off-target cleavage by CRISPR-Cas nucleases. Nature Biotechnology 33, 187-197 (2015).
3. Lettre, G & Bauer, D. E. Fetal haemoglobin in sickle-cell disease: from genetic epidemiology to new therapeutic strategies. Lancet 387, 2554-2564 (2016).
4. Vierstra, J. et al. Functional footprinting of regulatory DNA. Nature Methods 12, 927-930 (2015).
5. Canver, M. C. et al. BCL11A enhancer dissection by Cas9-mediated in situ saturating mutagenesis. Nature 527, 192-197 (2015).
6. Zettler, J., Schutz, V. & Mootz, H. D. The naturally split Npu DnaE intein exhibits an extraordinarily high rate in the protein trans-splicing reaction. FEBS Lett 583, 909-914 (2009).

TABLE 1

Association analysis of common SNPs in BCL11A DHSs +62, +58, or +55

| DHS | Marker | MAF | β | P | Conditional on rs1427407 β | Conditional on rs1427407 P | Conditional on rs1427407 and rs7606173 β | Conditional on rs1427407 and rs7606173 P |
|---|---|---|---|---|---|---|---|---|
| +62 | rs111575474 | 0.0153 | −0.2624 | 0.09762 | −0.0851 | 0.5584 | 0.0486 | 0.7368 |
| +62 | rs112105713 | 0.0115 | −0.3285 | 0.07755 | −0.2137 | 0.2097 | −0.0859 | 0.6107 |
| +62 | rs74958177 | 0.0646 | −0.3614 | $2.79 \times 10^{-6}$ | −0.1838 | 0.01041 | −0.0832 | 0.2518 |

TABLE 1-continued

Association analysis of common SNPs in BCL11A DHSs +62, +58, or +55

| DHS | Marker | MAF | β | P | Conditional on rs1427407 β | Conditional on rs1427407 P | Conditional on rs1427407 and rs7606173 β | Conditional on rs1427407 and rs7606173 P |
|---|---|---|---|---|---|---|---|---|
| +62 | rs1427407 | 0.2460 | 0.6634 | $7.23 \times 10^{-50}$ | — | — | — | — |
| +62 | rs7599488 | 0.3148 | −0.0047 | 0.9116 | 0.2622 | $2.43 \times 10^{-10}$ | 0.0915 | 0.3547 |
| +62 | rs1896293 | 0.1089 | −0.2623 | $2.52 \times 10^{-5}$ | −0.1248 | 0.03098 | 0.0241 | 0.6952 |
| +58 | rs6738440 | 0.2734 | −0.3820 | $1.25 \times 10^{-18}$ | −0.1935 | $5.64 \times 10^{-6}$ | −0.0223 | 0.6887 |
| +55 | rs147910897 | 0.0132 | −0.3656 | 0.03294 | −0.2586 | 0.09945 | −0.1575 | 0.3101 |
| +55 | rs148529953 | 0.0140 | −0.3521 | 0.04034 | −0.1423 | 0.3668 | −0.0098 | 0.9501 |
| +55 | rs7606173 | 0.4238 | −0.4691 | $2.86 \times 10^{-34}$ | −0.2632 | $9.66 \times 10^{-11}$ | — | — |

Association analysis of common (MAF > 1%) SNPs in BCL11A DHSs +62, +58, or +55 from 1178 individuals from CSSCD available for analysis.
DHS, DNase I hypersensitive site.
MAF, minor allele frequency.

TABLE 2

SNPs within BCL11A DHSs +62, +58, or +55

| Marker | CHR | POS | Major Allele | Minor Allele | DHS | Genotyped | MAF |
|---|---|---|---|---|---|---|---|
| rs149113684 | 2 | 60,717,544 | C | A | +62 | Monomorphic | 0.0000 |
| rs111575474 | 2 | 60,717,559 | C | T | +62 | YES | 0.0157 |
| rs148272134 | 2 | 60,717,643 | C | A | +62 | Failed Assay Design | — |
| rs182773253 | 2 | 60,717,676 | A | G | +62 | Monomorphic | 0.0000 |
| rs188706265 | 2 | 60,717,769 | C | T | +62 | Monomorphic | 0.0000 |
| rs74958177 | 2 | 60,717,776 | A | G | +62 | YES | 0.0645 |
| rs1427407 | 2 | 60,718,043 | G | T | +62 | YES | 0.2460 |
| rs35262352 | 2 | 60,718,076 | A | — | +62 | Failed Assay Design | — |
| rs79781583 | 2 | 60,718,077 | A | T | +62 | Failed Assay Design | — |
| rs201428515 | 2 | 60,718,088 | G | A | +62 | Monomorphic | 0.0000 |
| rs112105713 | 2 | 60,718,278 | G | A | +62 | YES | 0.1145 |
| rs7599488 | 2 | 60,718,347 | C | T | +62 | YES | 0.3149 |
| rs113636744 | 2 | 60,718,540 | C | T | +62 | YES | 0.0042 |
| rs35259900 | 2 | 60,718,555 | C | T | +62 | Failed Assay Design | — |
| rs111911554 | 2 | 60,718,569 | A | G | +62 | Failed Assay Design | — |
| rs137943695 | 2 | 60,718,574 | G | A | +62 | Monomorphic | 0.0000 |
| rs45579333 | 2 | 60,718,599 | G | A | +62 | Monomorphic | 0.0000 |
| rs77876582 | 2 | 60,718,639 | C | T | +62 | Failed Assay Design | — |
| rs112634025 | 2 | 60,718,708 | G | A | +62 | Failed Assay Design | — |
| rs45439602 | 2 | 60,718,721 | G | A | +62 | Failed Assay Design | — |
| rs112387548 | 2 | 60,718,762 | C | T | +62 | Failed Assay Design | — |
| rs191369155 | 2 | 60,718,781 | G | A | +62 | Failed Assay Design | — |
| rs6723022 | 2 | 60,718,807 | A | C | +62 | Monomorphic | 0.0000 |
| rs11422901 | 2 | 60,718,819 | G | A | +62 | Failed Assay Design | — |
| rs200632291 | 2 | 60,718,824 | A | G | +62 | Failed Assay Design | — |
| rs11387709 | 2 | 60,718,826 | A | — | +62 | Failed Assay Design | — |
| rs1896293 | 2 | 60,718,848 | G | T | +62 | YES | 0.1088 |
| rs71526487 | 2 | 60,721,587 | T | C | +58 | Failed Assay Design | — |
| rs185151573 | 2 | 60,721,639 | G | C | +58 | Monomorphic | 0.0000 |
| rs6721788 | 2 | 60,721,846 | T | C | +58 | YES | 0.0025 |
| rs76033449 | 2 | 60,721,900 | G | A | +58 | YES | 0.0004 |
| rs6706648 | 2 | 60,722,040 | T | C | +58 | Failed Genotyping | — |
| rs62142615 | 2 | 60,722,120 | T | C | +58 | YES | 0.0081 |
| rs35923541 | 2 | 60,722,197 | T | — | +58 | Monomorphic | 0.0000 |
| rs35815093 | 2 | 60,722,208 | G | — | +58 | Failed Assay Design | — |

TABLE 2-continued

SNPs within BCL11A DHSs +62, +58, or +55

| Marker | CHR | POS | Major Allele | Minor Allele | DHS | Genotyped | MAF |
|---|---|---|---|---|---|---|---|
| rs147659683 | 2 | 60,722,219 | G | A | +58 | Failed Assay Design | — |
| rs6738440 | 2 | 60,722,241 | A | G | +58 | YES | 0.2732 |
| rs189178945 | 2 | 60,722,449 | G | A | +58 | Monomorphic | 0.0000 |
| rs140819321 | 2 | 60,722,465 | G | A | +58 | YES | 0.0064 |
| rs181895125 | 2 | 60,722,609 | A | G | +58 | Monomorphic | 0.0000 |
| rs144676401 | 2 | 60,722,634 | C | T | +58 | Monomorphic | 0.0000 |
| rs147910897 | 2 | 60,724,818 | T | C | +55 | YES | 0.0132 |
| rs34322220 | 2 | 60,724,831 | T | — | +55 | Monomorphic | 0.0000 |
| rs148529953 | 2 | 60,724,967 | A | G | +55 | YES | 0.0140 |
| rs188426060 | 2 | 60,724,989 | T | G | +55 | Failed Assay Design | — |
| rs191734859 | 2 | 60,724,994 | A | G | +55 | Failed Assay Design | — |
| rs45442493 | 2 | 60,725,043 | G | C | +55 | Monomorphic | 0.0000 |
| rs59444712 | 2 | 60,725,047 | T | C | +55 | Failed Assay Design | — |
| rs35173197 | 2 | 60,725,052 | G | — | +55 | Failed Assay Design | — |
| rs188151753 | 2 | 60,725,071 | G | A | +55 | Failed Assay Design | — |
| rs181041409 | 2 | 60,725,143 | C | A | +55 | Failed Assay Design | — |
| rs142174420 | 2 | 60,725,169 | C | A | +55 | Monomorphic | 0.0000 |
| rs187333125 | 2 | 60,725,342 | C | G | +55 | Monomorphic | 0.0000 |
| rs45566439 | 2 | 60,725,384 | C | T | +55 | Failed Assay Design | — |
| rs7606173 | 2 | 60,725,451 | G | C | +55 | YES | 0.4235 |
| rs190502487 | 2 | 60,725,499 | C | T | +55 | Failed Assay Design | — |
| rs151187913 | 2 | 60,725,714 | G | T | +55 | Monomorphic | 0.0000 |
| rs113798461 | 2 | 60,725,727 | T | C | +55 | Monomorphic | 0.0000 |
| rs181699714 | 2 | 60,726,054 | G | A | +55 | Failed Genotyping | — |

SNPs falling within BCL11A DHSs +62, +58, or +55 and present in either dbSNP or the 1000 Genomes data for YRI, CEU and ASW reference populations.
Genotyped SNPs are identified and MAF within the CSSCD listed.
Genomic coordinates hg19.

TABLE 3

Additional markers found by Sanger re-sequencing

| Marker | CHR | POS | Major Allele | Minor Allele | DHS | Genotyped | MAF |
|---|---|---|---|---|---|---|---|
| ss711589103 | 2 | 60,717,561 | T | A | +62 | YES | 0.00085 |
| ss711589106 | 2 | 60,718,048 | C | G | +62 | Failed Assay Design | — |
| ss711589108 | 2 | 60,722,056 | G | A | +58 | YES | 0.00424 |
| ss711589109 | 2 | 60,722,355 | C | T | +58 | YES | 0.00085 |
| ss711589110 | 2 | 60,722,358 | C | T | +58 | Failed Assay Design | — |
| ss711589111 | 2 | 60,725,211 | G | T | +55 | YES | 0.00509 |
| ss711589113 | 2 | 60,725,564 | C | A | +55 | YES | 0.00127 |

88 individuals from CSSCD with extreme HbF phenotype underwent Sanger re-sequencing of the three DHSs within BCL11A.
Identified novel markers listed.
Genotyped SNPs are identified and MAF within the CSSCD listed.
Genomic coordinates hg19.

TABLE 4

Conditional analyses of four sentinel SNPs

| Marker | MAF | β | P | Conditional on rs1427407 β | Conditional on rs1427407 P | Conditional on rs766432 β | Conditional on rs766432 P | Conditional on rs11886868 β | Conditional on rs11886868 P | Conditional on rs4671393 β | Conditional on rs4671393 P |
|---|---|---|---|---|---|---|---|---|---|---|---|
| rs1427407 | 0.245 | 0.659 | $4.56 \times 10^{-29}$ | — | — | 0.656 | $3.38 \times 10^{-6}$ | 0.651 | $2.77 \times 10^{-10}$ | 0.666 | $1.86 \times 10^{-6}$ |
| rs766432 | 0.275 | 0.579 | $2.48 \times 10^{-24}$ | 0.0036 | 0.979 | — | — | 0.479 | $1.07 \times 10^{-5}$ | NA | NA |
| rs11886868 | 0.302 | 0.509 | $2.51 \times 10^{-21}$ | 0.0097 | 0.918 | 0.112 | 0.284 | — | — | 0.123 | 0.234 |
| rs4671393 | 0.274 | 0.576 | $4.41 \times 10^{-24}$ | −0.0065 | 0.961 | NA | NA | 0.466 | $1.7 \times 10^{-5}$ | — | — |

Conditional analyses of four common sentinel SNPs previously associated with HbF levels {{44; 20; 19; 36; 37; 515}}.
All four were genotyped in 728 individuals from the CSSCD.
It was not possible to calculate P for rs766432 when conditioning on rs4671393 (and vice versa) because these two markers are so strongly correlated ($r^2 = 0.997$).
$r^2 = 0.848$ between rs1427407 and rs766432; $r^2 = 0.709$ between rs1427407 and rs11886868; $r^2 = 0.850$ between rs1427407 and rs4671393; $r^2 = 0.761$ between rs766432 and rs11886868; $r^2 = 0.758$ between rs11886868 and rs4671393.

TABLE 5

Rare and low-frequency variant analysis

| DHS | Markers (n) | P | Conditional on rs1427407 P | Conditional on rs1427407 and rs7606173 P |
|---|---|---|---|---|
| +62 | 4 | 0.001488515 | 0.06092413 | 0.59352715 |
| +58 | 6 | 0.065057555 | 0.03668287 | 0.07145516 |
| +55 | 4 | 0.006806853 | 0.35021761 | 0.75880018 |
| all | 14 | 0.000631176 | 0.1503518 | 0.6908852 |

Rare and low-frequency variant analysis results (MAF < 5%).
The analysis was performed using the set-based SKAT-O algorithm using the individual DHSs +62, +58, and +55 as three different sets. The bottom row "all" shows the results of the tests when the three regions were collapsed together.

TABLE 6

Emulsion fusion haplotyping PCR sequencing

| Donor no. | G—G | A—T | G—T | A—G | Likelihood ratio G—G/A—T phase |
|---|---|---|---|---|---|
| 1 | 19 | 22 | 4 | 2 | $1.63 \times 10^{29}$ |
| 2 | 22 | 14 | 2 | 3 | $3.78 \times 10^{26}$ |
| 3 | 25 | 23 | 9 | 10 | $4.69 \times 10^{11}$ |

Emulsion fusion PCR analysis of rs7569946-rs1427407 haplotype.
Fusion PCR conducted in emulsion from three individual donors doubly heterozygous for rs7569946 and rs1427407, generating a fusion amplicon encompassing both SNPs. The fusion amplicon was cloned, and individual clones were Sanger sequenced. The number of clones of each genotype is listed. The likelihood ratio for the G—G/A—T as compared to G—T/A—G phase was calculated.

TABLE 7

Coordinates of fragments for reporter assays

| Reporter | Name | hg19, chr2 Start | hg19, chr2 End | Distance from BCL11A TSS (kb) Start | Distance from BCL11A TSS (kb) End | Length (bp) |
|---|---|---|---|---|---|---|
| LacZ | 52.0-64.4 | 60,716,189 | 60,728,612 | 64,444 | 52,021 | 12,423 |
| | 56.8-64.4 | 60,716,189 | 60,723,870 | 64,444 | 56,763 | 7,681 |
| | 52.0-57.6 | 60,722,992 | 60,728,612 | 57,641 | 52,021 | 5,620 |
| | +62 | 60,717,236 | 60,719,036 | 63,397 | 61,597 | 1,800 |
| | +58 | 60,722,006 | 60,723,058 | 58,627 | 57,575 | 1,052 |
| | +55 | 60,724,917 | 60,726,282 | 55,716 | 54,351 | 1,365 |
| GFP | +164 | 60,616,396 | 60,618,032 | 164,237 | 162,601 | 1,636 |
| | +156 | 60,623,536 | 60,624,989 | 157,097 | 155,644 | 1,453 |
| | +153 | 60,626,565 | 60,628,177 | 154,068 | 152,456 | 1,612 |
| | +62 | 60,717,236 | 60,719,036 | 63,397 | 61,597 | 1,800 |
| | +58 | 60,721,212 | 60,722,958 | 59,421 | 57,675 | 1,746 |
| | +55 | 60,724,780 | 60,726,471 | 55,853 | 54,162 | 1,691 |
| | +41 | 60,739,075 | 60,740,154 | 41,558 | 40,479 | 1,079 |
| | +32 | 60,748,003 | 60,749,009 | 32,630 | 31,624 | 1,006 |
| | −46 | 60,826,438 | 60,827,601 | −45,805 | −46,968 | 1,163 |
| | −52 | 60,831,589 | 60,833,556 | −50,956 | −52,923 | 1,967 |

Coordinates of the putative enhancer fragments cloned in the enhancer reporter assays.
Chromosome 2 coordinates listed in hg19 as well as in reference to the BCL11A TSS.

TABLE 8

Oligonucleotide sequences.

| Name | Sequence | Assay |
|---|---|---|
| mBcl11a-5'-F | AAAGAGCTGTCCGAAGTCCA | TALEN deletion PCR (SEQ ID NO: 10) |
| mBcl11a-5'-R | GGGCACTTCCTAGTCCCTCT | TALEN deletion PCR (SEQ ID NO: 11) |
| mBcl11a-del1-F | TTTGAGCAGGAGGGAATTTG | TALEN deletion PCR (SEQ ID NO: 12) |

TABLE 8-continued

Oligonucleotide sequences.

| Name | Sequence | Assay |
| --- | --- | --- |
| mBcl11a-del1-R | ATGTTGTGGTCCCTGTGGTT | TALEN deletion PCR (SEQ ID NO: 13) |
| mBcl11a-del2-F | GCAAGGCAGGTACCAAACAT | TALEN deletion PCR (SEQ ID NO: 14) |
| mBcl11a-del2-R | TAGAGATTCCAGGCCCCTTT | TALEN deletion PCR (SEQ ID NO: 15) |
| mBcl11a-3'-F | AGCAAGGAAAGGTGAAGCAG | TALEN deletion PCR (SEQ ID NO: 16) |
| mBcl11a-3'-R | CCCAATGTCTTCCGAACTGT | TALEN deletion PCR (SEQ ID NO: 17) |
| mBcl11a-downstreamTALEN-F | AGGCTGGTCTTGGGATTTTT | TALEN deletion PCR (SEQ ID NO: 18) |
| mBcl11a-downstreamTALEN-R | GCCTTTAACAAGGGTGTCCA | TALEN deletion PCR (SEQ ID NO: 19) |
| mBcl11a-5'probe-F | CATAGACCTGGGTCCTGGAA | 5'-probe for Southern blot (SEQ ID NO: 20) |
| mBcl11a-5'probe-R | TTGCAGAGTGACTCCTGTGG | 5'-probe for Southern blot (SEQ ID NO: 21) |
| hBCL11A-52.0-F | CCAGCCATACCCAAAACAAA | lacZ reporter cloning (SEQ ID NO: 22) |
| hBCL11A-64.4-R | CTTTCCCTCTTGCCACTCAG | lacZ reporter cloning (SEQ ID NO: 23) |
| hBCL11A-56.8-F | GGCAGAGAAGGCACAGTGA | lacZ reporter cloning (SEQ ID NO: 24) |
| hBCL11A-57.6-R | GGCTGTCCTGGCATGTAAGT | lacZ reporter cloning (SEQ ID NO: 25) |
| hBCL11A-63.4-F | AACAGACCCATGTGCTAGGC | lacZ/GFP reporter cloning (SEQ ID NO: 26) |
| hBCL11A-61.6-R | TGTGTGGACTGCCTTTTCTG | lacZ/GFP reporter cloning (SEQ ID NO: 27) |
| hBCL11A-58.6-F | GGGAAAGGGAGAGGAAAAA | lacZ reporter cloning (SEQ ID NO: 28) |
| hBCL11A-57.6-R | CTCAGAAAAATGACAGCACCA | lacZ reporter cloning (SEQ ID NO: 29) |
| hBCL11A-55.7-F | GGACTCAGTGGCCTCTTTTG | lacZ reporter cloning (SEQ ID NO: 30) |
| hBCL11A-54.4-R | GAAAGATAATGGCAGCCCAGA | lacZ reporter cloning (SEQ ID NO: 31) |
| hBCL11A-164.2-F | TGTGTGGCCAACCTGTAAAA | GFP reporter cloning (SEQ ID NO: 32) |
| hBCL11A-162.6-R | CTCGCTCTGTTTCCCAGTTC | GFP reporter cloning (SEQ ID NO: 33) |
| hBCL11A-157.1-F | CTCTCCGACGACCTCTTTTG | GFP reporter cloning (SEQ ID NO: 34) |
| hBCL11A-155.6-R | GTAGGGAAGGGGCTACTTGG | GFP reporter cloning (SEQ ID NO: 35) |
| hBCL11A-154.1-F | AGAGCCAAACTCCGTCTCAA | GFP reporter cloning (SEQ ID NO: 36) |
| hBCL11A-152.5-R | AAATACCACAGCCCAACAGC | GFP reporter cloning (SEQ ID NO: 37) |
| hBCL11A-59.4-F | GAACAGAGACCACTACTGGCAAT | GFP reporter cloning (SEQ ID NO: 38) |
| hBCL11A-57.7-R | GGGGAAGGGGTATTGAATTG | GFP reporter cloning (SEQ ID NO: 39) |
| hBCL11A-55.9-F | CTTCCACTGGATGGCACTTT | GFP reporter cloning (SEQ ID NO: 40) |
| hBCL11A-54.2-R | ACTTCAGCCTCCAGCACTGT | GFP reporter cloning (SEQ ID NO: 41) |
| hBCL11A-41.6-F | CCTCCCAGCAATGTAGGTGT | GFP reporter cloning (SEQ ID NO: 42) |
| hBCL11A-40.5-R | TGGTGTGGTCCACTGTGACT | GFP reporter cloning (SEQ ID NO: 43) |
| hBCL11A-32.6-F | GCAAGCTTAGCCCCTTCTTT | GFP reporter cloning (SEQ ID NO: 44) |
| hBCL11A-31.6-R | TGAGGCAGAGTCAGATGTGG | GFP reporter cloning (SEQ ID NO: 45) |
| hBCL11A-n45.8-F | CCCCGCTCAGAGTAAGTGAG | GFP reporter cloning (SEQ ID NO: 46) |
| hBCL11A-n47.0-R | GGAAACTGCCTATCCCATGA | GFP reporter cloning (SEQ ID NO: 47) |
| hBCL11A-n51.0-F | CAACACCCCGATTTCAGACT | GFP reporter cloning (SEQ ID NO: 48) |
| hBCL11A-n52.9-R | GAATGGTCCCGATCTCTTGA | GFP reporter cloning (SEQ ID NO: 49) |

TABLE 8-continued

Oligonucleotide sequences.

| Name | Sequence | Assay |
|---|---|---|
| mGapdh-RT-F | TGGTGAAGGTCGGTGTGAAC | RT-qPCR (Gapdh) (SEQ ID NO: 50) |
| mGapdh-RT-R | CCATGTAGTTGAGGTCAATGAAGG | RT-qPCR (Gapdh) (SEQ ID NO: 51) |
| mBcl11a-RT-e1e2-F | AACCCCAGCACTTAAGCAAA | RT-qPCR (Bcl11a exon-1/2) (SEQ ID NO: 52) |
| mBcl11a-RT-e1e2-R | ACAGGTGAGAAGGTCGTGGT | RT-qPCR (Bcl11a exon-1/2) (SEQ ID NO: 53) |
| mBcl11a-RT-e2e3-F | GCCCCAAACAGGAACACATA | RT-qPCR (Bcl11a exon-2/3) (SEQ ID NO: 54) |
| mBcl11a-RT-e2e3-R | GGGGCATATTCTGCACTCAT | RT-qPCR (Bcl11a exon-2/3) (SEQ ID NO: 55) |
| mBcl11a-RT-e4e4-F | ATGCGAGCTGTGCAACTATG | RT-qPCR (Bcl11a exon-4/4, XLisoform) (SEQ ID NO: 56) |
| mBcl11a-RT-e4e4-R | GTAAACGTCCTTCCCCACCT | RT-qPCR (Bcl11a exon-4/4, XLisoform (SEQ ID NO: 57) |
| mBcl11a-RT-e4e5-F | CAGCTCAAAAGAGGGCAGAC | RT-qPCR (Bcl11a exon-4/5, Lisoform (SEQ ID NO: 58) |
| mBcl11a-RT-e4e5-R | GAGCTTCCATCCGAAAACTG | RT-qPCR (Bcl11a exon-4/5, Lisoform) (SEQ ID NO: 59) |
| mHbby-RT-F | TGGCCTGTGGAGTAAGGTCAA | RT-qPCR (eY) (SEQ ID NO: 60) |
| mHbby-RT-R | GAAGCAGAGGACAAGTTCCCA | RT-qPCR (eY) (SEQ ID NO: 61) |
| mHbb-bh1-RT-F | TGGACAACCTCAAGGAGACC | RT-qPCR (bH1) (SEQ ID NO: 62) |
| mHbb-bh1-RT-R | ACCTCTGGGGTGAATTCCTT | RT-qPCR (bH1) (SEQ ID NO: 63) |
| mHbb-b1-RT-F | TTTAACGATGGCCTGAATCACTT | RT-qPCR (b1/b2) (SEQ ID NO: 64) |
| mHbb-b1-RT-R | CAGCACAATCACGATCATATTGC | RT-qPCR (b1/b2) (SEQ ID NO: 65) |
| lacZ-RT-F | GCCAACATTGAGACACATGG | RT-qPCR (lacZ) (SEQ ID NO: 66) |
| lacZ-RT-R | TGTCTCTCTGCACCATCCTG | RT-qPCR (lacZ) (SEQ ID NO: 67) |
| lacZ-F | TTCAATGCTGTCAGGTGCTC | PCR genotyping (lacZ) (SEQ ID NO: 68) |
| lacZ-R | GCCATGTGTCTCAATGTTGG | PCR genotyping (lacZ) (SEQ ID NO: 69) |
| rs7569946-F | GTCTGCCCTCTTTTGAGCTG | haplotyping fusion PCR (SEQ ID NO: 70) |
| rs7569946-R | GACTCCAGACAATCGCCTTT | haplotyping fusion PCR (SEQ ID NO: 71) |
| rs7569946-R-rc- | AAAGGCGATTGTCTGGAGTCAACCTT | bridging primer, haplotyping fusion (SEQ ID NO: 72) |
| rs1427407-F | CTTAGCACCCACAAAC | PCR (SEQ ID NO: 73) |
| rs1427407-R | CATGTTACTGCAACTTGCTTTTT | haplotyping fusion PCR (SEQ ID NO: 74) |
| rs7569946-nested-F | AGATCCCTCCGTCCAGCTC | haplotyping fusion PCR (SEQ ID NO: 75) |
| rs1427407-nested-R | TGAAAGTTCAAGTAGATATCAGAAGG | haplotyping fusion PCR (SEQ ID NO: 76) |
| 3C-hBCL11A-150.6-F | AGCAAACCACACAGACTGAAGA | 3C (SEQ ID NO: 77) |
| 3C-hBCL11A-140.9-F | CCAGAGCCATTTACGTCACA | 3C (SEQ ID NO: 78) |
| 3C-hBCL11A-114.1-F | CAGAAGGGAATAAGGTACTCTGGA | 3C (SEQ ID NO: 79) |
| 3C-hBCL11A-111.5-F | GTTTGGGCCTCAAGGTCTTT | 3C (SEQ ID NO: 80) |
| 3C-hBCL11A-109.1-F | GAGGTTGGGAGTAAGCATTCTG | 3C (SEQ ID NO: 81) |
| 3C-hBCL11A-100.7-F | ACGCATCAGAATGCCCATAG | 3C (SEQ ID NO: 82) |
| 3C-hBCL11A-92.3-F | TTTTGAAAGAAAACGCTGACA | 3C (SEQ ID NO: 83) |
| 3C-hBCL11A-80.2-F | TTCCAGCTGGTTAAATTTAGGG | 3C (SEQ ID NO: 84) |
| 3C-hBCL11A-77.2-F | AGAAGGGGCCAGAAGAACAG | 3C (SEQ ID NO: 85) |
| 3C-hBCL11A-72.5-F | CCTTCTTTTTCTTTCTTGGTTGC | 3C (SEQ ID NO: 86) |
| 3C-hBCL11A-66.8-F | CCCTGCGTGCCATTAAAATA | 3C (SEQ ID NO: 87) |

TABLE 8-continued

Oligonucleotide sequences.

| Name | Sequence | Assay |
|---|---|---|
| 3C-hBCL11A-61.2-F | AAAGGCCTTGGGAAGAAAGA | 3C (SEQ ID NO: 88) |
| 3C-hBCL11A-59.1-F | GCAAGTCAGTTGGGAACACA | 3C (SEQ ID NO: 89) |
| 3C-hBCL11A-57.1-F | GGACTCAGTGGCCTCTTTTG | 3C (SEQ ID NO: 90) |
| 3C-hBCL11A-52.2-F | CTGTCTCTGTCTCCCCCAAG | 3C (SEQ ID NO: 91) |
| 3C-hBCL11A-47-F | CCAATGCTCCTGTAACAAAGG | 3C (SEQ ID NO: 92) |
| 3C-hBCL11A-43.5-F | AATGCAGTAGGCAAAGAAGCA | 3C (SEQ ID NO: 93) |
| 3C-hBCL11A-38.6-F | GAAATTTGGAAGGCCACAGA | 3C (SEQ ID NO: 94) |
| 3C-hBCL11A-29.3-F | GCTTGCAACAATTAAAAGATGG | 3C (SEQ ID NO: 95) |
| 3C-hBCL11A-27.1-F | GGTGACAAGGGAGAACCACT | 3C (SEQ ID NO: 96) |
| 3C-hBCL11A-20.9-F | TGATTTCCTTGCAGCCTTTT | 3C (SEQ ID NO: 97) |
| 3C-hBCL11A-8.6-F | CACACCCACAGCAACAAATG | 3C (SEQ ID NO: 98) |
| 3C-hBCL11Apromoter-R | TGCAGAGATCCCCCAAAGTA | 3C (SEQ ID NO: 99) |
| 3C-hBCL11A-n8.3-F | CTCAGGGAGCAAGGGAAATA | 3C (SEQ ID NO: 100) |
| 3C-hBCL11A-n12.6-F | CCCTCCCAACAGGGATTTAT | 3C (SEQ ID NO: 101) |
| 3C-hBCL11A-n19.5-F | CAAAATTGAACACCTATGGTCTGA | 3C (SEQ ID NO: 102) |
| 3C-hBCL11A-n29.8-F | AGGAAGACTTTGGCCTCCAT | 3C (SEQ ID NO: 103) |
| 3C-hBCL11A-n34.6-F | TTCCAAACAATTATACACCAACAAA | 3C (SEQ ID NO: 104) |
| 3C-hBCL11A-n54-F | TTTCATGGGGAATAGCCAAC | 3C (SEQ ID NO: 105) |
| 3C-hBCL11A-n78.2-F | CCCTACTTGTTATTTGCTTCTGC | 3C (SEQ ID NO: 106) |
| 3C-hBCL11A-n104.4-F | AGCTGAAGTTTCAGGGACCA | 3C (SEQ ID NO: 107) |
| 3C-LCR-HS1-F | CCACACCTGCCTTCCTTAGA | 3C (SEQ ID NO: 108) |
| 3C-LCR-HS3-F | TGCATATGATGGGGTAGCAG | 3C (SEQ ID NO: 109) |
| ChIP-hBCL11A-68.7-F | AAGAGAAGGGGGAATTTGGA | ChIP-qPCR (SEQ ID NO: 110) |
| ChIP-hBCL11A-68.7-R | TGGTGATAAGGGCAGGAAAC | ChIP-qPCR (SEQ ID NO: 111) |
| ChIP-hBCL11A-65.5-F | AGGAAGCTGCAGAAAGGTGA | ChIP-qPCR (SEQ ID NO: 112) |
| ChIP-hBCL11A-65.5-R | TGCTTCCCCAGGTTTAGATG | ChIP-qPCR (SEQ ID NO: 113) |
| ChIP-hBCL11A-64.7-F | CCACTGCTACCCAAAACGAT | ChIP-qPCR (SEQ ID NO: 114) |
| ChIP-hBCL11A-64.7-R | CAAGAGCGAAACTCCACCTC | ChIP-qPCR (SEQ ID NO: 115) |
| ChIP-hBCL11A-63.9-F | ACTGTGTGCCAAGTGACCAG | ChIP-qPCR (SEQ ID NO: 116) |
| ChIP-hBCL11A-63.9-R | CAGCTTCCTTCAGGTGCTTC | ChIP-qPCR (SEQ ID NO: 117) |
| ChIP-hBCL11A-63.1-F | CATGCTGCCTTTGTCTTCTG | ChIP-qPCR (SEQ ID NO: 118) |
| ChIP-hBCL11A-63.1-R | TGTGGAGCTCTGGAATGATG | ChIP-qPCR (SEQ ID NO: 119) |
| ChIP-hBCL11A-63.0-F | GAGCTCCACAATCCAACTCC | ChIP-qPCR (SEQ ID NO: 120) |
| ChIP-hBCL11A-63.0-R | CCAGGAAGGAAATGAGAACG | ChIP-qPCR (SEQ ID NO: 121) |
| ChIP-hBCL11A-62.5-F | ACCCACAAACATTTCCCTTCT | ChIP-qPCR (SEQ ID NO: 122) |
| ChIP-hBCL11A-62.5-R | TTTGCTCTTCTCCAGGGTGT | ChIP-qPCR (SEQ ID NO: 123) |
| ChIP-hBCL11A-62.4-F | TTTAAACAGCCACCCCACAC | ChIP-qPCR (SEQ ID NO: 124) |
| ChIP-hBCL11A-62.4-R | ACCACGTAGTTGGGCTTCAC | ChIP-qPCR (SEQ ID NO: 125) |

TABLE 8-continued

Oligonucleotide sequences.

| Name | Sequence | Assay |
|---|---|---|
| ChIP-hBCL11A-62.2-F | TTTCAACCATGGTCATCTGC | ChIP-qPCR (SEQ ID NO: 126) |
| ChIP-hBCL11A-62.2-R | CCCTCTGGCATCAAAATGAG | ChIP-qPCR (SEQ ID NO: 127) |
| ChIP-hBCL11A-61.8-F | GAACCTGGGAGGCAGAAGAT | ChIP-qPCR (SEQ ID NO: 128) |
| ChIP-hBCL11A-61.8-R | TTTTTGGTGAGACGGAGATTT | ChIP-qPCR (SEQ ID NO: 129) |
| ChIP-hBCL11A-61.7-F | CCGGGCAACAAGAGTAAATC | ChIP-qPCR (SEQ ID NO: 130) |
| ChIP-hBCL11A-61.7-R | ATGCCTAGGGTGTTTTGACG | ChIP-qPCR (SEQ ID NO: 131) |
| ChIP-hBCL11A-61.5-F | CTCCGTGTTGAGAGCCAAGT | ChIP-qPCR (SEQ ID NO: 132) |
| ChIP-hBCL11A-61.5-R | TGTGTGGACTGCCTTTTCTG | ChIP-qPCR (SEQ ID NO: 133) |
| ChIP-hBCL11A-61.3-F | CAGAAAAGGCAGTCCACACA | ChIP-qPCR (SEQ ID NO: 134) |
| ChIP-hBCL11A-61.3-R | CCTCTCCAGATTCCCTCTCA | ChIP-qPCR (SEQ ID NO: 135) |
| ChIP-hBCL11A-61.0-F | AGCGAGACCCTGTCTCAAAA | ChIP-qPCR (SEQ ID NO: 136) |
| ChIP-hBCL11A-61.0-R | TCCAGCAGGCTTCAAAAAGT | ChIP-qPCR (SEQ ID NO: 137) |
| ChIP-hBCL11A-60.8-F | GGTGGATAACCCCATCTCAG | ChIP-qPCR (SEQ ID NO: 138) |
| ChIP-hBCL11A-60.8-R | GGAAATGAGAATGCCCTTTG | ChIP-qPCR (SEQ ID NO: 139) |
| ChIP-hBCL11A-60.5-F | CAGTCTAGAAAGCCCCCTCA | ChIP-qPCR (SEQ ID NO: 140) |
| ChIP-hBCL11A-60.5-R | GTGGGGGTTCAGTGGTTAGA | ChIP-qPCR (SEQ ID NO: 141) |
| ChIP-hBCL11A-60.3-F | TCCATGGTGTGGAGTGTGTT | ChIP-qPCR (SEQ ID NO: 142) |
| ChIP-hBCL11A-60.3-R | ACCCACATGGCAACCAATAG | ChIP-qPCR (SEQ ID NO: 143) |
| ChIP-hBCL11A-60.0-F | CCATTCCCTGGAGAGTTCAA | ChIP-qPCR (SEQ ID NO: 144) |
| ChIP-hBCL11A-60.0-R | GGGGTCTCTTCCCATCATTT | ChIP-qPCR (SEQ ID NO: 145) |
| ChIP-hBCL11A-59.9-F | ATGGGAAGAGACCCCAAAAC | ChIP-qPCR (SEQ ID NO: 146) |
| ChIP-hBCL11A-59.9-R | GGACTCCGAACACCACACTT | ChIP-qPCR (SEQ ID NO: 147) |
| ChIP-hBCL11A-59.5-F | GGGATCAGAGGTGAACAGGA | ChIP-qPCR (SEQ ID NO: 148) |
| ChIP-hBCL11A-59.5-R | TTTAATCAGCTTCCGCCACT | ChIP-qPCR (SEQ ID NO: 149) |
| ChIP-hBCL11A-59.0-F | TGGGGAGAGAAGAGTGGAAA | ChIP-qPCR (SEQ ID NO: 150) |
| ChIP-hBCL11A-59.0-R | TTGCCAATTGGAGATTAGGG | ChIP-qPCR (SEQ ID NO: 151) |
| ChIP-hBCL11A-58.7-F | TGCTCCGAGCTTGTGAACTA | ChIP-qPCR (SEQ ID NO: 152) |
| ChIP-hBCL11A-58.7-R | GGGAAAGGGCCTGATAACTT | ChIP-qPCR (SEQ ID NO: 153) |
| ChIP-hBCL11A-58.3-F | GAGAGTGCAGACAGGGGAAG | ChIP-qPCR (SEQ ID NO: 154) |
| ChIP-hBCL11A-58.3-R | CCTCTTTCGGAAGGCTCTCT | ChIP-qPCR (SEQ ID NO: 155) |
| ChIP-hBCL11A-58.0-F | TGGACTTTGCACTGGAATCA | ChIP-qPCR (SEQ ID NO: 156) |
| ChIP-hBCL11A-58.0-R | GATGGCTGAAAAGCGATACA | ChIP-qPCR (SEQ ID NO: 157) |
| ChIP-hBCL11A-57.3-F | GGGGAGATGATTGAAAGCAA | ChIP-qPCR (SEQ ID NO: 158) |
| ChIP-hBCL11A-57.3-R | AGAACTTTCCCGGTTCTGGT | ChIP-qPCR (SEQ ID NO: 159) |
| ChIP-hBCL11A-57.0-F | GCTCTGGACACACAGCAAAA | ChIP-qPCR (SEQ ID NO: 160) |
| ChIP-hBCL11A-57.0-R | TCAAATCCTTGCCTTGAACC | ChIP-qPCR (SEQ ID NO: 161) |
| ChIP-hBCL11A-56.6-F | CCTCAAATCTCCCTCACTGG | ChIP-qPCR (SEQ ID NO: 162) |
| ChIP-hBCL11A-56.6-R | GGGAAATGGGTCCTGCTTTA | ChIP-qPCR (SEQ ID NO: 163) |

TABLE 8-continued

Oligonucleotide sequences.

| Name | Sequence | Assay |
|---|---|---|
| ChIP-hBCL11A-56.3-F | AGGGAGTACACCGCAGACAC | ChIP-qPCR (SEQ ID NO: 164) |
| ChIP-hBCL11A-56.3-R | AAGGAAGGCTGCAAGGAAAT | ChIP-qPCR (SEQ ID NO: 165) |
| ChIP-hBCL11A-55.9-F | GACTTAAACTGCCGCTCCTG | ChIP-qPCR (SEQ ID NO: 166) |
| ChIP-hBCL11A-55.9-R | TGACTGGTAAGAGCCGATTG | ChIP-qPCR (SEQ ID NO: 167) |
| ChIP-hBCL11A-55.3-F | GCTGGGGTGAGTCAAAAGTC | ChIP-qPCR (SEQ ID NO: 168) |
| ChIP-hBCL11A-55.3-R | GGTCACCTTAAGGAGCCACA | ChIP-qPCR (SEQ ID NO: 169) |
| ChIP-hBCL11A-54.8-F | GCACCTGCATTTGTTTTTCA | ChIP-qPCR (SEQ ID NO: 170) |
| ChIP-hBCL11A-54.8-R | GGGTCAGATCACCTCTGCTC | ChIP-qPCR (SEQ ID NO: 171) |
| ChIP-hBCL11A-54.4-F | AGGCATCCAAAGGGAAGAAT | ChIP-qPCR (SEQ ID NO: 172) |
| ChIP-hBCL11A-54.4-R | GAAGATAATGGCAGCCCAGA | ChIP-qPCR (SEQ ID NO: 173) |
| ChIP-hBCL11A-54.0-F | TGGGAAAGGTTGCACATTCT | ChIP-qPCR (SEQ ID NO: 174) |
| ChIP-hBCL11A-54.0-R | GGGCCTCAGGCTCTTTATCT | ChIP-qPCR (SEQ ID NO: 175) |
| ChIP-hBCL11A-53.4-F | CCACTGCCAGGCTGTTTACT | ChIP-qPCR (SEQ ID NO: 176) |
| ChIP-hBCL11A-53.4-R | GACCGAAAGGAGGAGAGGAG | ChIP-qPCR (SEQ ID NO: 177) |
| ChIP-hBCL11A-53.1-F | CAGTTCCCCCATTATGCACT | ChIP-qPCR (SEQ ID NO: 178) |
| ChIP-hBCL11A-53.1-R | CCCTTCTCTGAAGGCACATC | ChIP-qPCR (SEQ ID NO: 179) |
| ChIP-hBCL11A-52.7-F | TTCAAGCCTTGGTGGATAGG | ChIP-qPCR (SEQ ID NO: 180) |
| ChIP-hBCL11A-52.7-R | GCCAGGAAATTGGTGGTAGA | ChIP-qPCR (SEQ ID NO: 181) |
| ChIP-hBCL11A-52.3-F | TGCCCACATGAGACATCTTT | ChIP-qPCR (SEQ ID NO: 182) |
| ChIP-hBCL11A-52.3-R | AAATTGGCTGCCATTGAATC | ChIP-qPCR (SEQ ID NO: 183) |
| ChIP-hBCL11A-51.3-F | CCACCAGAAGTCCTGGAAAA | ChIP-qPCR (SEQ ID NO: 184) |
| ChIP-hBCL11A-51.3-R | TTGGAGGGACCTGATCTCTG | ChIP-qPCR (SEQ ID NO: 185) |
| ChIP-hBCL11A-50.2-F | CCAAGATGGAGAAGCCACAT | ChIP-qPCR (SEQ ID NO: 186) |
| ChIP-hBCL11A-50.2-R | TCTGTCTTGGGTCTCCTGGT | ChIP-qPCR (SEQ ID NO: 187) |
| ChIP-hBCL11A-49.8-F | GAGAAGCCCTCAGCAAACAC | ChIP-qPCR (SEQ ID NO: 188) |
| ChIP-hBCL11A-49.8-R | GGTTGCATCTTGGCTCCTAA | ChIP-qPCR (SEQ ID NO: 189) |
| ChIP-hBCL11A-49.5-F | GAAATGCAGGAAAGGAACGA | ChIP-qPCR (SEQ ID NO: 190) |
| ChIP-hBCL11A-49.5-R | TCTAGCAGATGGGGTTTTGG | ChIP-qPCR (SEQ ID NO: 191) |
| ChIP-hOct4-prom-F | AGTCTGGGCAACAAAGTGAGA | ChIP-qPCR (SEQ ID NO: 192) |
| ChIP-hOct4-prom-R | AGAAACTGAGGAGAAGGATG | ChIP-qPCR (SEQ ID NO: 193) |
| ChIP-hHS3-F | ATAGACCATGAGTAGAGGGCAGAC | ChIP-qPCR (SEQ ID NO: 194) |
| ChIP-hHS3-R | TGATCCTGAAAACATAGGAGTCAA | ChIP-qPCR (SEQ ID NO: 195) |
| ChIP-hHS-40-F | CAGATAACTGGGCCAACCAT | ChIP-qPCR (SEQ ID NO: 196) |
| ChIP-hHS-40-R | ATTCACCCCTTTCCCTTGTC | ChIP-qPCR (SEQ ID NO: 197) |
| ChIP-hGAPDH-F | CGTAGCTCAGGCCTCAAGAC | ChIP-qPCR (SEQ ID NO: 198) |
| ChIP-hGAPDH-R | CGAACAGGAGGAGCAGAGAG | ChIP-qPCR (SEQ ID NO: 199) |

Oligonucleotides used in indicated experiments.11

What is claimed is:

1. A method for producing a cell having decreased BCL11A mRNA or protein expression, the method comprising;
   contacting an isolated cell with a guideRNA and an agent that deletes the GATA1 binding element in the functional core of the BCL11A enhancer +58 kb,
   wherein the agent is a composition comprising a fusion protein comprising at least two DNA-targeting endonucleases, or the agent is a composition comprising a vector carrying the coding sequence of a fusion protein comprising at least two DNA-targeting endonucleases whereby the DNA-targeting endonuclease fusion protein makes precise cleavages near the targeted GATA1 binding element to delete it, thereby reducing the mRNA or protein expression of BCL11A,
   wherein the guideRNA comprises the sequence selected from the group consisting of SEQ ID Nos: 2-7.

2. The method of claim 1, wherein the isolated cell is a progenitor cell, induced pluripotent stem cell, or hematopoietic progenitor cell.

3. The method of claim 1, wherein the isolated cell is a CD34+ cell.

4. The method of claim 1, wherein contacting is ex vivo or in vitro.

5. The method of claim 1, wherein the fusion protein comprising at least two DNA-targeting endonucleases comprising a first Cas9 or Cas12a nuclease, said nuclease comprising a protospacer adjacent motif recognition domain and a peptide linker, wherein said peptide linker is attached to a second Cas9 or Cas12a nuclease.

6. The method of claim 5, wherein the said Cas9 nuclease of the fusion protein is selected from the group consisting of SpCas9, SaCas9, NmCas9, CjCas9 and An-Cas9.

7. The method of claim 5, wherein the said Cas12a nuclease of the fusion protein is selected from the group consisting of FnCas12a, LbCas12a and AsCas12a.

8. The method of claim 5, said protospacer adjacent motif recognition domain of fusion protein is selected from the group consisting of SpCas9, SpCas9$^{MT1}$, SpCas9$^{MT2}$, SpCas9$^{MT3}$, NmCas9$^{SM}$ and NmCas9$^{DM}$.

9. The method of claim 1, wherein said fusion protein further comprises a guide RNA which is attached to a guide sequence element.

* * * * *

SEQUENCE LISTING

<160> NUMBER OF SEQ ID NOS: 226

<210> SEQ ID NO 1
<211> LENGTH: 7
<212> TYPE: DNA
<213> ORGANISM: Homo sapiens

<400> SEQUENCE: 1 wgataar                                                                    7

<210> SEQ ID NO 2
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 2
gcuagucuag ugcaagcuaa guuuuagagc uagaaauagc aaguuaaaau aaggcuaguc      60
cguuaucaac uugaaaaagu ggcaccgagu cggugcuuuu                            100

<210> SEQ ID NO 3
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
ccagggucaa uacaacuuug guuuuagagc uagaaauagc aaguuaaaau aaggcuaguc      60
cguuaucaac uugaaaaagu ggcaccgagu cggugcuuuu                            100

<210> SEQ ID NO 4
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
gcuuuuauca caggcuccag gguuuuagua cucuggaaac agaaucuacu aaaacaaggc      60
aaaaugccgu guuuaucucg ucaacuuguu ggcgagauuu u                          101

<210> SEQ ID NO 5
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
gguuuggccu cugauuaggg uguuuuagua cucuggaaac agaaucuacu aaaacaaggc      60
aaaaugccgu guuuaucucg ucaacuuguu ggcgagauuu u                          101

<210> SEQ ID NO 6
<211> LENGTH: 101
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 6
gccucugauu agggugggggg cguuuuagua cucuggaaac agaaucuacu aaaacaaggc    60
aaaaugccgu guuuaucucg ucaacuuguu ggcgagauuu u                        101

<210> SEQ ID NO 7
<211> LENGTH: 147
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
caggcuccag gaaggguuug gcguuguagc ucccuuucuc auuucggaaa cgaaaugaga    60
accguugcua caauaaggcc gucugaaaag augugccgca acgcucugcc ccuuaaagcu    120
ucugcuuuaa ggggcaucgu uuauuuu                                       147

<210> SEQ ID NO 8
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
caggcuccag gaaggguuug gcguuguagc ucccuuucuc auuucg                   46

<210> SEQ ID NO 9
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cgaaaugaga accguugcua caauaaggcc gucugaaaag augugccgca acgcucugcc    60
ccuuaaagcu ucugcuuuaa ggggcaucgu uuauuuu                             97

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaagagctgt ccgaagtcca                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggcacttcc tagtccctct                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttgagcagg agggaatttg                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgttgtggt ccctgtggtt                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcaaggcagg taccaaacat                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tagagattcc aggccccttt                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agcaaggaaa ggtgaagcag                                           20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cccaatgtct tccgaactgt                                           20

```
<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aggctggtct tgggattttt                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcctttaaca agggtgtcca                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
catagacctg ggtcctggaa                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttgcagagtg actcctgtgg                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccagccatac ccaaaacaaa                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctttccctct tgccactcag                                                   20

<210> SEQ ID NO 24
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggcagagaag gcacagtga                                                    19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggctgtcctg gcatgtaagt                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aacagaccca tgtgctaggc                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgtgtggact gcctttctg                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gggaaaaggg agaggaaaaa                                                   20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctcagaaaaa tgacagcacc a                                                 21

<210> SEQ ID NO 30
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggactcagtg gcctcttttg                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gaagataatg gcagcccaga                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgtgtggcca acctgtaaaa                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctcgctctgt ttcccagttc                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctctccgacg acctcttttg                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtagggaagg ggctacttgg                                                   20

<210> SEQ ID NO 36
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 36
agagccaaac tccgtctcaa                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaataccaca gcccaacagc                                                  20

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaacagagac cactactggc aat                                              23

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggggaagggg tattgaattg                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cttccactgg atggcacttt                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acttcagcct ccagcactgt                                                  20

<210> SEQ ID NO 42
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 42
cctcccagca atgtaggtgt                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tggtgtggtc cactgtgact                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcaagcttag ccccttcttt                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgaggcagag tcagatgtgg                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccccgctcag agtaagtgag                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggaaactgcc tatcccatga                                                    20

<210> SEQ ID NO 48
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 48
caacaccccg atttcagact                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gaatggtccc gatctcttga                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tggtgaaggt cggtgtgaac                                                    20

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccatgtagtt gaggtcaatg aagg                                               24

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aaccccagca cttaagcaaa                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
acaggtgaga aggtcgtggt                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 54
gccccaaaca ggaacacata                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggggcatatt ctgcactcat                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atgcgagctg tgcaactatg                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gtaaacgtcc ttccccacct                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cagctcaaaa gagggcagac                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gagcttccat ccgaaaactg                                               20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 60
tggcctgtgg agtaaggtca a                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gaagcagagg acaagttccc a                                              21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tggacaacct caaggagacc                                                20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
acctctgggg tgaattcctt                                                20

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tttaacgatg gcctgaatca ctt                                            23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cagcacaatc acgatcatat tgc                                            23

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 66
gccaacattg agacacatgg					20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tgtctctctg caccatcctg					20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttcaatgctg tcaggtgctc					20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gccatgtgtc tcaatgttgg					20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtctgccctc ttttgagctg					20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gactccagac aatcgccttt					20

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
aaaggcgatt gtctggagtc aacctt                                          26

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cttagcaccc acaaac                                                     16

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
catgttactg caacttgctt ttt                                             23

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agatccctcc gtccagctc                                                  19

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tgaaagttca agtagatatc agaagg                                          26

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agcaaaccac acagactgaa ga                                              22

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
```

```
ccagagccat ttacgtcaca                                              20
```

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
cagaagggaa taaggtactc tgga                                         24
```

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
gtttgggcct caaggtcttt                                              20
```

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81

```
gaggttggga gtaagcattc tg                                           22
```

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
acgcatcaga atgcccatag                                              20
```

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
ttttgaaaga aaacgctgac a                                            21
```

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

```
ttccagctgg ttaaatttag gg                                           22
```

```
<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agaaggggcc agaagaacag                                               20

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86 ccttctttt ctttcttggt tgc                                            23

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ccctgcgtgc cattaaaata                                               20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aaaggccttg ggaagaaaga                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcaagtcagt tgggaacaca                                               20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggactcagtg gcctcttttg                                               20
```

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctgtctctgt ctcccccaag                                           20

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ccaatgctcc tgtaacaaag g                                         21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aatgcagtag gcaaagaagc a                                         21

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaaatttgga aggccacaga                                           20

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcttgcaaca attaaaagat gg                                        22

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggtgacaagg gagaaccact                                           20

```
<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgatttcctt gcagcctttt                                                     20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cacacccaca gcaacaaatg                                                     20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgcagagatc ccccaaagta                                                     20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctcagggagc aagggaaata                                                     20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccctcccaac agggatttat                                                     20

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
caaaattgaa cacctatggt ctga                                                24

<210> SEQ ID NO 103
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aggaagactt tggcctccat                                               20

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ttccaaacaa ttatacacca acaaa                                         25

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tttcatgggg aatagccaac                                               20

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ccctacttgt tatttgcttc tgc                                           23

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agctgaagtt tcagggacca                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ccacacctgc cttccttaga                                               20

<210> SEQ ID NO 109
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tgcatatgat ggggtagcag                                              20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aagagaaggg ggaatttgga                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tggtgataag ggcaggaaac                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aggaagctgc agaaaggtga                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tgcttcccca ggtttagatg                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ccactgctac ccaaaacgat                                              20

<210> SEQ ID NO 115
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 115
caagagcgaa actccacctc                                                    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
actgtgtgcc aagtgaccag                                                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cagcttcctt caggtgcttc                                                    20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
catgctgcct ttgtcttctg                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tgtggagctc tggaatgatg                                                    20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gagctccaca atccaactcc                                                    20

<210> SEQ ID NO 121
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 121
ccaggaagga aatgagaacg                                              20

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
acccacaaac atttcccttc t                                            21

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tttgctcttc tccagggtgt                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tttaaacagc caccccacac                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
accacgtagt tgggcttcac                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tttcaaccat ggtcatctgc                                              20

<210> SEQ ID NO 127
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 127
ccctctggca tcaaaatgag                                               20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gaacctggga ggcagaagat                                               20

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tttttggtga gacggagatt t                                             21

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccgggcaaca agagtaaatc                                               20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
atgcctaggg tgttttgacg                                               20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctccgtgttg agagccaagt                                               20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 133
tgtgtggact gccttttctg                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cagaaaaggc agtccacaca                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cctctccaga ttccctctca                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
agcgagaccc tgtctcaaaa                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tccagcaggc ttcaaaaagt                                              20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ggtggataac cccatctcag                                              20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggaaatgaga atgccctttg                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cagtctagaa agcccctca                                               20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 gtggggttc agtggttaga                                               20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tccatggtgt ggagtgtgtt                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
acccacatgg caaccaatag                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ccattccctg gagagttcaa                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggggtctctt cccatcattt                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
atgggaagag accccaaaac                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggactccgaa caccacactt                                              20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gggatcagag gtgaacagga                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tttaatcagc ttccgccact                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tggggagaga agagtggaaa                                              20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ttgccaattg gagattaggg                                           20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tgctccgagc ttgtgaacta                                           20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gggaaagggc ctgataactt                                           20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gagagtgcag acaggggaag                                           20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cctctttcgg aaggctctct                                           20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tggactttgc actggaatca                                           20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gatggctgaa aagcgataca                                          20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggggagatga ttgaaagcaa                                          20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
agaactttcc cggttctggt                                          20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gctctggaca cacagcaaaa                                          20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tcaaatcctt gccttgaacc                                          20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cctcaaatct ccctcactgg                                          20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gggaaatggg tcctgcttta                                          20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
agggagtaca ccgcagacac                                                     20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
aaggaaggct gcaaggaaat                                                     20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gacttaaact gccgctcctg                                                     20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgactggtaa gagccgattg                                                     20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gctggggtga gtcaaaagtc                                                     20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggtcacctta aggagccaca                                                     20

```
<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gcacctgcat ttgtttttca                                                   20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gggtcagatc acctctgctc                                                   20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
aggcatccaa agggaagaat                                                   20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gaagataatg gcagcccaga                                                   20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tgggaaaggt tgcacattct                                                   20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gggcctcagg ctctttatct                                                   20
```

```
<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ccactgccag gctgtttact                                                    20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gaccgaaagg aggagaggag                                                    20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cagttccccc attatgcact                                                    20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cccttctctg aaggcacatc                                                    20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ttcaagcctt ggtggatagg                                                    20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gccaggaaat tggtggtaga                                                    20

<210> SEQ ID NO 182
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgcccacatg agacatcttt                                               20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aaattggctg ccattgaatc                                               20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ccaccagaag tcctggaaaa                                               20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttggagggac ctgatctctg                                               20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ccaagatgga gaagccacat                                               20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tctgtcttgg gtctcctggt                                               20

<210> SEQ ID NO 188
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gagaagccct cagcaaacac                                              20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ggttgcatct tggctcctaa                                              20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gaaatgcagg aaaggaacga                                              20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tctagcagat ggggttttgg                                              20

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agtctgggca acaaagtgag a                                            21

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
agaaactgag gagaaggatg                                              20

<210> SEQ ID NO 194
<211> LENGTH: 24
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 194
atagaccatg agtagagggc agac                                    24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
tgatcctgaa aacataggag tcaa                                    24

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
cagataactg ggccaaccat                                         20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
attcacccct ttccttgtc                                          20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 198
cgtagctcag gcctcaagac                                         20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 199
cgaacaggag gagcagagag                                         20

<210> SEQ ID NO 200
<211> LENGTH: 9
<212> TYPE: PRT
<213> ORGANISM: Unknown

<220> FEATURE:
<223> OTHER INFORMATION: Description of Unknown:
      "LAGLIDADG" family peptide motif sequence

<400> SEQUENCE: 200

Leu Ala Gly Leu Ile Asp Ala Asp Gly
1               5

<210> SEQ ID NO 201
<211> LENGTH: 66
<212> TYPE: DNA
<213> ORGANISM: Homo sapiens

<400> SEQUENCE: 201
cacgccccca ccctaatcag aggccaaacc cttcctggag cctgtgataa aagcaactgt    60
tagctt                                                               66

<210> SEQ ID NO 202
<211> LENGTH: 81
<212> TYPE: DNA
<213> ORGANISM: Homo sapiens

<400> SEQUENCE: 202
cacgccccca ccctaatcag aggccaaacc cttcctggag cctgtgataa aagcaactgt    60
tagcttgcac tagactagct t                                              81

<210> SEQ ID NO 203
<211> LENGTH: 66
<212> TYPE: DNA
<213> ORGANISM: Homo sapiens

<400> SEQUENCE: 203
atcagaggcc aaaccttcc tggagcctgt gataaaagca actgttagct tgcactagac     60
tagctt                                                               66

<210> SEQ ID NO 204
<211> LENGTH: 67
<212> TYPE: DNA
<213> ORGANISM: Homo sapiens

<400> SEQUENCE: 204
atcagaggcc aaaccttcc tggagcctgt gataaaagca actgttagct tgcactagac     60
tagcttc                                                              67

<210> SEQ ID NO 205
<211> LENGTH: 76
<212> TYPE: DNA
<213> ORGANISM: Homo sapiens

<400> SEQUENCE: 205
ccagggtcaa tacaactttg aagctagtct agtgcaagct aacagttgct tttatcacag    60
gctccaggaa gggttt                                                    76

<210> SEQ ID NO 206
<211> LENGTH: 76
<212> TYPE: DNA
<213> ORGANISM: Homo sapiens

<400> SEQUENCE: 206
cacgccccca ccctaatcag aggccaaacc cttcctggag cctgtgataa aagcaactgt    60

```
tagcttgcac tagact                                                    76

<210> SEQ ID NO 207
<211> LENGTH: 65
<212> TYPE: DNA
<213> ORGANISM: Homo sapiens

<400> SEQUENCE: 207
gctagtctag tgcaagctaa cagttgcttt tatcacaggc tccaggaagg gtttggcctc    60
tgatt                                                                65

<210> SEQ ID NO 208
<211> LENGTH: 70
<212> TYPE: DNA
<213> ORGANISM: Homo sapiens

<400> SEQUENCE: 208
gctagtctag tgcaagctaa cagttgcttt tatcacaggc tccaggaagg gtttggcctc    60
tgattagggt                                                           70

<210> SEQ ID NO 209
<211> LENGTH: 76
<212> TYPE: DNA
<213> ORGANISM: Homo sapiens

<400> SEQUENCE: 209
gctagtctag tgcaagctaa cagttgcttt tatcacaggc tccaggaagg gtttggcctc    60
tgattagggt gggggc                                                    76

<210> SEQ ID NO 210
<211> LENGTH: 82
<212> TYPE: DNA
<213> ORGANISM: Homo sapiens

<400> SEQUENCE: 210
gctagtctag tgcaagctaa cagttgcttt tatcacaggc tccaggaagg gtttggcctc    60
tgattagggt gggggcgtgg gt                                             82

<210> SEQ ID NO 211
<211> LENGTH: 230
<212> TYPE: DNA
<213> ORGANISM: Homo sapiens

<400> SEQUENCE: 211
gccagaaaag agatatggca tctactctta gacataacac accagggtca atacaacttt    60
gaagctagtc tagtgcaagc taacagttgc ttttatcaca ggctccagga agggtttggc   120
ctctgattag ggtgggggcg tgggtggggt agaagaggac tggcagacct ctccatcggt   180
ggccgtttgc caggggggc ctctttcgga aggctctctt ggtgatggag              230

<210> SEQ ID NO 212
<211> LENGTH: 20
<212> TYPE: DNA
<213> ORGANISM: Homo sapiens

<400> SEQUENCE: 212
ctaacagttg cttttatcac                                                20

<210> SEQ ID NO 213
<211> LENGTH: 100
```

<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 213
cuaacaguug cuuuuaucac guuuuagagc uagaaauagc aaguuaaaau aaggcuaguc      60
cguuaucaac uugaaaaagu ggcaccgagu cggugcuuuu                          100

<210> SEQ ID NO 214
<211> LENGTH: 21
<212> TYPE: DNA
<213> ORGANISM: Homo sapiens

<400> SEQUENCE: 214
gcctctgatt agggtggggg c                                               21

<210> SEQ ID NO 215
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 215
gccucugauu agguggggg cguuuuagua cucuggaaac agaaucuacu aaaacaaggc      60
aaaaugccgu guuuaucucg ucaacuuguu ggcgagauuu                          100

<210> SEQ ID NO 216
<211> LENGTH: 21
<212> TYPE: DNA
<213> ORGANISM: Homo sapiens

<400> SEQUENCE: 216
tgattagggt gggggcgtgg g                                               21

<210> SEQ ID NO 217
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 217
ugauuagggu gggggcgugg gguuuuagua cucuggaaac agaaucuacu aaaacaaggc     60
aaaaugccgu guuuaucucg ucaacuuguu ggcgagauuu                          100

<210> SEQ ID NO 218
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tccccggcat cctagcgcgc tgggctagca atcgcctccg cgtcccttcc aacagtacc      59

<210> SEQ ID NO 219
<211> LENGTH: 59
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 219
tccccggcat cctagcgcgc tgggctagcg gtactgttgg aagggacgcg gaggcgatt        59

<210> SEQ ID NO 220
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ggtactgttg aagggacgc ggaggcgatt gctagctccc cggcatccta gcgcgctgg         59

<210> SEQ ID NO 221
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
aatcgcctcc gcgtcccttc caacagtacc gctagctccc cggcatccta gcgcgctgg        59

<210> SEQ ID NO 222
<211> LENGTH: 59
<212> TYPE: DNA
<213> ORGANISM: Homo sapiens

<400> SEQUENCE: 222
ggtgagtgag tgtgtgcgtg tggggttgag ggcgttggag cggggagaag gccaggggt        59

<210> SEQ ID NO 223
<211> LENGTH: 71
<212> TYPE: DNA
<213> ORGANISM: Homo sapiens

<400> SEQUENCE: 223
ggtgagtgag tgtgtgcgtg tggggttgag ggcgttggag cggggagaag gccaggggtc       60
actccaggat t                                                            71

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ggtgagtgag tgtgtgcact ccaggatt                                          28

<210> SEQ ID NO 225
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 225
ctgtgtgggt gagtgagtgt gtgcactcca ggattccaat a                     41

<210> SEQ ID NO 226
<211> LENGTH: 78
<212> TYPE: DNA
<213> ORGANISM: Homo sapiens

<400> SEQUENCE: 226
cacaccaggg tcaatacaac tttgaagcta gtctagtgca agctaacagt tgcttttatc 60
acaggctcca ggaagggt                                               78
```